United States Patent
Djupesland et al.

(10) Patent No.: US 11,554,229 B2
(45) Date of Patent: Jan. 17, 2023

(54) NASAL ADMINISTRATION

(71) Applicant: OPTINOSE AS, Oslo (NO)

(72) Inventors: Per Gisle Djupesland, Oslo (NO); Ramy A. Mahmoud, Skillman, NJ (US); John Messina, Downingtown, PA (US)

(73) Assignee: OptiNose Inc., Yardley, PA (US)

( * ) Notice: Subject to any disclaimer, the term of this patent is extended or adjusted under 35 U.S.C. 154(b) by 699 days.

(21) Appl. No.: 14/315,132

(22) Filed: Jun. 25, 2014

(65) Prior Publication Data

US 2015/0144129 A1 May 28, 2015

Related U.S. Application Data

(63) Continuation-in-part of application No. 14/226,287, filed on Mar. 26, 2014, now abandoned.

(Continued)

(51) Int. Cl.
*A61M 15/08* (2006.01)
*A61M 16/00* (2006.01)
(Continued)

(52) U.S. Cl.
CPC ........ *A61M 15/08* (2013.01); *A61M 15/0098* (2014.02); *A61M 16/0057* (2013.01);
(Continued)

(58) Field of Classification Search
CPC ...... A61M 15/00; A61M 15/0003–001; A61M 15/002; A61M 15/0021; A61M 15/0028; A61M 15/0033; A61M 15/0045; A61M 15/0051; A61M 15/0065; A61M 15/0085; A61M 15/0086–0088; A61M 15/06; A61M 15/08–085; A61M 11/00–005;
(Continued)

(56) References Cited

U.S. PATENT DOCUMENTS 605,436 A 6/1898 Kellogg
642,748 A 2/1900 Manners
(Continued)

FOREIGN PATENT DOCUMENTS

CN 1805730 A 7/2006
CN 101918061 A 12/2010
(Continued)

OTHER PUBLICATIONS

Cindy H. Dubin, *Nothing to Sneeze at*, Pharmaceutical Formulation & Quality Magazine (Jan. 29, 2003).
(Continued)

*Primary Examiner* — Michael J Tsai
(74) *Attorney, Agent, or Firm* — Finnegan, Henderson, Farabow, Garrett & Dunner, LLP

(57) ABSTRACT

A method of delivering a substance, such as one or more of a triptan, a nasal steroid or carbon dioxide gas, to the nasal cavity of a subject, in particular for the treatment of headaches, for example, migraine, or rhinosinusitis, for example, chronic rhinosinusitis, optionally with polyps, the method comprising the steps of fitting a nosepiece to one nostril of the subject, delivering the substance through the nosepiece to the posterior region of the nasal cavity of the subject.

22 Claims, 42 Drawing Sheets

Related U.S. Application Data

(60) Provisional application No. 61/805,400, filed on Mar. 26, 2013.

(51) Int. Cl.
*A61M 16/14* (2006.01)
*A61M 16/20* (2006.01)
*A61M 15/00* (2006.01)
A61M 11/00 (2006.01)
A61M 16/10 (2006.01)

(52) U.S. Cl.
CPC ............ *A61M 16/14* (2013.01); *A61M 16/20* (2013.01); *A61M 11/003* (2014.02); *A61M 15/009* (2013.01); *A61M 15/0021* (2014.02); *A61M 15/0041* (2014.02); *A61M 16/0045* (2013.01); *A61M 16/107* (2014.02); *A61M 16/1055* (2013.01); *A61M 2202/0225* (2013.01); *A61M 2202/0275* (2013.01); *A61M 2202/0468* (2013.01); *A61M 2202/064* (2013.01); *A61M 2205/3324* (2013.01); *A61M 2205/3334* (2013.01)

(58) Field of Classification Search
CPC ...... A61M 2202/00; A61M 2202/0007; A61M 2202/06; A61M 2202/064; A61M 16/16; A61G 10/00; A61G 10/02; A61J 1/10; A61J 1/142; A61J 1/2006–2017
See application file for complete search history.

(56) References Cited

U.S. PATENT DOCUMENTS

| | | |
|---|---|---|
| 746,749 A | 12/1903 | Seidel |
| 4,583,524 A * | 4/1986 | Hutchins ............... G09B 23/288 128/898 |
| 4,689,223 A | 8/1987 | Arias |
| 4,919,132 A * | 4/1990 | Miser .................... A61M 16/00 116/277 |
| 5,658,549 A | 8/1997 | Akehurst et al. |
| 5,669,377 A | 9/1997 | Fenn |
| 5,797,392 A | 8/1998 | Keldmann et al. |
| 5,894,841 A * | 4/1999 | Voges .................... A24F 47/008 128/203.12 |
| 5,993,782 A * | 11/1999 | Gardner ................ A61K 9/0043 424/45 |
| 6,186,141 B1 | 2/2001 | Pike et al. |
| 6,470,882 B1 | 10/2002 | Newhouse et al. |
| 6,648,848 B1 | 11/2003 | Keldmann et al. |
| 6,715,485 B1 | 4/2004 | Djupesland |
| 6,792,947 B1 * | 9/2004 | Bowden ............ A61M 16/0078 128/203.11 |
| 6,959,708 B1 | 11/2005 | Rasor et al. |
| D530,815 S | 10/2006 | Murphy et al. |
| 7,189,753 B1 | 3/2007 | Cady et al. |
| 7,347,201 B2 | 3/2008 | Djupesland |
| 7,377,901 B2 | 5/2008 | Djupesland et al. |
| 7,481,218 B2 | 1/2009 | Djupesland |
| 7,543,581 B2 | 6/2009 | Djupesland |
| 7,740,014 B2 | 6/2010 | Djupesland |
| 7,784,460 B2 | 8/2010 | Djupesland et al. |
| 7,841,337 B2 | 11/2010 | Djupesland |
| 7,854,227 B2 | 12/2010 | Djupesland |
| 7,934,503 B2 | 5/2011 | Djupesland et al. |
| 7,975,690 B2 | 6/2011 | Djupesland |
| 8,047,202 B2 | 11/2011 | Djupesland |
| 8,146,589 B2 | 4/2012 | Djupesland |
| 8,171,929 B2 | 5/2012 | Djupesland et al. |
| 8,327,844 B2 | 12/2012 | Djupesland |
| 8,511,303 B2 | 8/2013 | Djupesland |
| 8,522,778 B2 | 9/2013 | Djupesland |
| 8,550,073 B2 | 10/2013 | Djupesland |
| 8,555,877 B2 | 10/2013 | Djupesland |
| 8,555,878 B2 | 10/2013 | Djupesland |
| 8,590,530 B2 | 11/2013 | Djupesland et al. |
| 8,596,278 B2 | 12/2013 | Djupesland |
| 8,800,555 B2 | 8/2014 | Djupesland |
| 8,875,704 B2 | 11/2014 | Djupesland et al. |
| 8,899,229 B2 | 12/2014 | Djupesland et al. |
| 8,910,629 B2 | 12/2014 | Djupesland et al. |
| D723,156 S | 2/2015 | Djupesland et al. |
| D725,769 S | 3/2015 | Djupesland et al. |
| 8,978,647 B2 | 3/2015 | Djupesland et al. |
| 9,010,325 B2 | 4/2015 | Djupesland et al. |
| 9,038,630 B2 | 5/2015 | Djupesland et al. |
| 9,067,034 B2 | 6/2015 | Djupesland et al. |
| 9,072,857 B2 | 7/2015 | Djupesland |
| 9,108,015 B2 | 8/2015 | Djupesland et al. |
| 9,119,932 B2 | 9/2015 | Djupesland |
| 9,132,249 B2 | 9/2015 | Djupesland |
| 9,144,652 B2 | 9/2015 | Djupesland et al. |
| 9,168,341 B2 | 10/2015 | Djupesland |
| 9,205,208 B2 | 12/2015 | Djupesland |
| 9,205,209 B2 | 12/2015 | Djupesland |
| 9,272,104 B2 | 3/2016 | Djupesland |
| D759,805 S | 6/2016 | Djupesland |
| D761,951 S | 7/2016 | Djupesland |
| 2002/0058009 A1 | 5/2002 | Bartus et al. |
| 2003/0015190 A1 | 1/2003 | Rabinowitz et al. |
| 2003/0133877 A1 | 7/2003 | Levin |
| 2003/0192540 A1 | 10/2003 | Myrman et al. |
| 2004/0024330 A1 | 2/2004 | Djupesland et al. |
| 2004/0037809 A1 | 2/2004 | Quay et al. |
| 2004/0112378 A1 | 6/2004 | Djupesland |
| 2004/0112379 A1 | 6/2004 | Djupesland |
| 2004/0112380 A1 | 6/2004 | Djupesland |
| 2004/0138098 A1 | 7/2004 | Fein |
| 2004/0138618 A1 | 7/2004 | Mazzoni |
| 2004/0149289 A1 | 8/2004 | Djupesland |
| 2004/0153033 A1 | 8/2004 | Mazzoni |
| 2004/0167158 A1 | 8/2004 | Edwards et al. |
| 2004/0182388 A1 | 9/2004 | Djupesland |
| 2005/0028812 A1 | 2/2005 | Djupesland |
| 2005/0034723 A1 | 2/2005 | Bennett et al. |
| 2005/0043706 A1 | 2/2005 | Eaton et al. |
| 2005/0072430 A1 | 4/2005 | Djupesland |
| 2005/0235992 A1 | 10/2005 | Djupesland |
| 2005/0240147 A1 | 10/2005 | Makower et al. |
| 2006/0002861 A1 | 1/2006 | Biggadike |
| 2006/0076011 A1 | 4/2006 | Rasor et al. |
| 2006/0096589 A1 | 5/2006 | Djupesland |
| 2006/0106227 A1 | 5/2006 | Reddy et al. |
| 2006/0107957 A1 | 5/2006 | Djupesland |
| 2006/0147389 A1 | 7/2006 | Staniforth et al. |
| 2006/0169278 A1 | 8/2006 | Djupesland et al. |
| 2006/0207596 A1 | 9/2006 | Lane |
| 2006/0219240 A1 | 10/2006 | Djupesland |
| 2006/0219241 A1 | 10/2006 | Djupesland |
| 2006/0225732 A1 | 10/2006 | Djupesland |
| 2006/0231094 A1 | 10/2006 | Djupesland |
| 2007/0031340 A1 | 2/2007 | Hale et al. |
| 2007/0039614 A1 | 2/2007 | Djupesland |
| 2007/0039615 A1 | 2/2007 | Rasor et al. |
| 2007/0125371 A1 | 6/2007 | Djupesland |
| 2007/0129665 A1 | 6/2007 | Dickens et al. |
| 2007/0169779 A1 | 7/2007 | Freeman |
| 2007/0186927 A1 | 8/2007 | Djupesland et al. |
| 2008/0156319 A1 | 7/2008 | Avni |
| 2008/0161771 A1 | 7/2008 | Djupesland |
| 2008/0163874 A1 | 7/2008 | Djupesland |
| 2008/0200848 A1 | 8/2008 | Avni |
| 2008/0221471 A1 | 9/2008 | Djupesland et al. |
| 2008/0223363 A1 | 9/2008 | Djupesland |
| 2008/0226736 A1 | 9/2008 | Caponetti et al. |
| 2008/0260848 A1 | 10/2008 | Nagata et al. |
| 2008/0289629 A1 | 11/2008 | Djupesland et al. |
| 2009/0025713 A1 | 1/2009 | Keller et al. |
| 2009/0101146 A1 | 4/2009 | Djupesland |
| 2009/0293873 A1 * | 12/2009 | Djupesland ....... A61M 15/0028 128/203.15 |
| 2009/0304802 A1 | 12/2009 | Djupesland et al. |
| 2009/0314293 A1 | 12/2009 | Djupesland |

(56) References Cited

U.S. PATENT DOCUMENTS

| | | | |
|---|---|---|---|
| 2009/0320832 | A1 | 12/2009 | Djupesland |
| 2010/0035805 | A1 | 2/2010 | Hafner |
| 2010/0037890 | A1 | 2/2010 | Surber et al. |
| 2010/0051022 | A1 | 3/2010 | Djupesland et al. |
| 2010/0057047 | A1* | 3/2010 | Djupesland ......... A61M 15/009 514/1.1 |
| 2010/0104665 | A1 | 4/2010 | Rasor et al. |
| 2010/0178331 | A1 | 7/2010 | Nagata et al. |
| 2010/0179090 | A1 | 7/2010 | Havelund et al. |
| 2010/0242959 | A1* | 9/2010 | Djupesland ....... A61M 15/0028 128/203.15 |
| 2010/0282246 | A1 | 11/2010 | Djupesland et al. |
| 2010/0288275 | A1* | 11/2010 | Djupesland ....... A61M 15/0028 128/203.15 |
| 2010/0300439 | A1 | 12/2010 | Djupesland et al. |
| 2010/0311655 | A1 | 12/2010 | Leonard et al. |
| 2011/0023869 | A1 | 2/2011 | Djupesland |
| 2011/0046546 | A1 | 2/2011 | Rasor et al. |
| 2011/0053827 | A1 | 3/2011 | Hafner |
| 2011/0088690 | A1 | 4/2011 | Djupesland et al. |
| 2011/0088691 | A1 | 4/2011 | Djupesland |
| 2011/0114087 | A1 | 5/2011 | Djupesland et al. |
| 2011/0126830 | A1 | 6/2011 | Djupesland et al. |
| 2011/0259329 | A1 | 10/2011 | Djupesland et al. |
| 2011/0318277 | A1 | 12/2011 | Dalby et al. |
| 2011/0318345 | A1 | 12/2011 | Djupesland |
| 2012/0000459 | A1 | 1/2012 | Djupesland |
| 2012/0006323 | A1 | 1/2012 | Djupesland |
| 2012/0073571 | A1 | 3/2012 | Djupesland |
| 2012/0090608 | A1 | 4/2012 | Djupesland et al. |
| 2012/0260915 | A1 | 10/2012 | Djupesland |
| 2013/0008437 | A1 | 1/2013 | Vecellio-None et al. |
| 2013/0098362 | A1 | 4/2013 | Djupesland et al. |
| 2013/0125889 | A1 | 5/2013 | Djupesland et al. |
| 2013/0327320 | A1 | 12/2013 | Djupesland |
| 2014/0018295 | A1 | 1/2014 | Djupesland |
| 2014/0041660 | A1 | 2/2014 | Djupesland et al. |
| 2014/0060536 | A1 | 3/2014 | Djupesland |
| 2014/0073562 | A1 | 3/2014 | Djupesland |
| 2014/0144442 | A1 | 5/2014 | Djupesland et al. |
| 2014/0144443 | A1 | 5/2014 | Djupesland et al. |
| 2014/0166008 | A1 | 6/2014 | Djupesland |
| 2014/0194400 | A1 | 7/2014 | Hildebrand-Cyrener et al. |
| 2014/0202456 | A1 | 7/2014 | Djupesland |
| 2014/0246022 | A1 | 9/2014 | Djupesland et al. |
| 2015/0007811 | A1 | 1/2015 | Djupesland et al. |
| 2015/0013670 | A1 | 1/2015 | Djupesland et al. |
| 2015/0013677 | A1 | 1/2015 | Djupesland et al. |
| 2015/0053201 | A1 | 2/2015 | Djupesland et al. |
| 2015/0090259 | A1 | 4/2015 | Djupesland et al. |
| 2015/0101605 | A1 | 4/2015 | Djupesland et al. |
| 2015/0144129 | A1 | 5/2015 | Djupesland et al. |
| 2015/0165139 | A1 | 6/2015 | Hafner |
| 2015/0182709 | A1 | 7/2015 | Djupesland |
| 2015/0246194 | A1 | 9/2015 | Djupesland |
| 2015/0367090 | A1 | 12/2015 | Djupesland et al. |
| 2015/0367091 | A1 | 12/2015 | Djupesland et al. |
| 2016/0001022 | A1 | 1/2016 | Djupesland et al. |
| 2016/0045687 | A1 | 2/2016 | Djupesland |
| 2016/0051778 | A1 | 2/2016 | Djupesland et al. |
| 2016/0074603 | A1 | 3/2016 | Djupesland et al. |
| 2016/0082206 | A1 | 3/2016 | Djupesland et al. |
| 2016/0082207 | A1 | 3/2016 | Djupesland et al. |
| 2016/0166788 | A1 | 6/2016 | Djupesland et al. |
| 2016/0184537 | A1 | 6/2016 | Djupesland |
| 2016/0193435 | A1 | 7/2016 | Djupesland |
| 2016/0250408 | A1 | 9/2016 | Djupesland |

FOREIGN PATENT DOCUMENTS

| | | |
|---|---|---|
| CN | 102580061 A | 7/2012 |
| CN | 103463716 A | 12/2013 |
| EP | 1 820 493 A2 | 8/2007 |
| EP | 2 653 183 A1 | 10/2013 |
| GB | 2 400 565 A | 10/2004 |
| GB | 2 448 183 A | 10/2008 |
| JP | 10-508004 | 8/1998 |
| JP | 2003-40766 A | 2/2003 |
| JP | 2003-518484 A | 6/2003 |
| JP | 2004-538027 A | 12/2004 |
| JP | 2006-523630 A | 10/2006 |
| JP | 2007-503873 A | 3/2007 |
| JP | 2008-509143 A | 3/2008 |
| JP | 2010-538081 A | 12/2010 |
| JP | 2011-510964 A | 4/2011 |
| JP | 2011-528355 A | 11/2011 |
| JP | 2016-521680 A | 7/2016 |
| RU | 2 255 736 C2 | 1/2004 |
| RU | 2 270 683 C2 | 2/2004 |
| RU | 2 373 936 C2 | 6/2006 |
| RU | 2008 136 888 A | 3/2010 |
| WO | WO 96/05810 | 2/1996 |
| WO | WO 96/22802 | 8/1996 |
| WO | WO 96/32344 | 10/1996 |
| WO | WO 97/33579 | 9/1997 |
| WO | WO 98/53869 | 12/1998 |
| WO | WO 99/49923 | 10/1999 |
| WO | WO 00/41816 | 7/2000 |
| WO | WO 00/51672 | 9/2000 |
| WO | WO 01/03645 A2 | 1/2001 |
| WO | WO 01/36018 A2 | 5/2001 |
| WO | WO 01/39772 A1 | 6/2001 |
| WO | WO 01/39789 A1 | 6/2001 |
| WO | WO 01/47493 A1 | 7/2001 |
| WO | WO 01/64280 A1 | 9/2001 |
| WO | WO 01/97689 | 12/2001 |
| WO | WO 02/068029 | 9/2002 |
| WO | WO 02/068030 | 9/2002 |
| WO | WO 02/068031 | 9/2002 |
| WO | WO 02/068032 | 9/2002 |
| WO | WO 03/000310 | 1/2003 |
| WO | WO 03/020350 | 3/2003 |
| WO | WO 03/082393 | 10/2003 |
| WO | WO 03/084591 | 10/2003 |
| WO | WO 03/090812 | 11/2003 |
| WO | WO 2004/004814 | 1/2004 |
| WO | WO 2004/004922 | 1/2004 |
| WO | WO 2004/060433 | 7/2004 |
| WO | WO 2004/091574 A1 | 10/2004 |
| WO | WO 2004/091575 A1 | 10/2004 |
| WO | WO 2004/091622 A1 | 10/2004 |
| WO | WO 2004/103447 | 12/2004 |
| WO | WO 2005/016423 | 2/2005 |
| WO | WO 2005/021059 | 3/2005 |
| WO | WO 2005/023330 A2 | 3/2005 |
| WO | WO 2006/017505 A2 | 2/2006 |
| WO | WO 2006/030210 | 3/2006 |
| WO | WO 2006/090149 | 8/2006 |
| WO | WO 2007/083073 | 7/2007 |
| WO | WO 2007/093784 | 8/2007 |
| WO | WO 2007/093791 | 8/2007 |
| WO | WO 2007/099361 | 9/2007 |
| WO | WO 2007/102089 | 9/2007 |
| WO | WO 2007/107887 | 9/2007 |
| WO | WO 2007/125318 | 11/2007 |
| WO | WO 2007/141541 | 12/2007 |
| WO | WO 2008/012531 | 1/2008 |
| WO | WO 2008/065403 | 6/2008 |
| WO | WO 2008/078730 A1 | 7/2008 |
| WO | WO 2008/081326 | 7/2008 |
| WO | WO 2008/081327 | 7/2008 |
| WO | WO 2008/122791 | 10/2008 |
| WO | WO 2008/122795 | 10/2008 |
| WO | WO 2009/032955 A1 | 3/2009 |
| WO | WO 2009/044172 | 4/2009 |
| WO | WO 2009/095684 A1 | 8/2009 |
| WO | WO 2010/009028 A1 | 1/2010 |
| WO | WO 2010/029441 | 3/2010 |
| WO | WO 2010/138884 A2 | 12/2010 |
| WO | WO 2012/035427 | 3/2012 |
| WO | WO 2012/094283 A2 | 7/2012 |
| WO | WO 2012/123819 | 9/2012 |
| WO | WO 2012/163501 A1 | 12/2012 |

(56) References Cited

FOREIGN PATENT DOCUMENTS

| WO | WO 2013/039785 A2 | 3/2013 |
| WO | WO 2013/123417 A1 | 8/2013 |
| WO | WO 2013/124491 | 8/2013 |
| WO | WO 2013/124492 | 8/2013 |
| WO | WO 2013/124493 | 8/2013 |
| WO | WO 2014/155192 | 10/2014 |

OTHER PUBLICATIONS

Per Gisle Djupesland, *Nasal Delivery of Vaccines*, EPC (Jan. 29, 2003).
Per Gisle Djupesland, *Who Nose How Far Nasal Delivery Can Go?*, EPC (Oct. 7, 2003).
Per Gisle Djupesland, *Bi-directional Nasal Drug Delivery*, Innovations in Pharmaceutical Technology (Jul. 10, 2004).
P.G. Djupesland, *Bi-Directional Nasal Delivery of Aerosols Can Prevent Lung Deposition*, Journal of Aerosol Medicine (Sep. 2004).
*Bi-Directional Nasal Device Delivers Drug on Exhalation*, Pharmaceutical Technology (Sep. 10, 2004).
Ola Dale et al., *Intranasal Midazolam: A Comparison of Two Delivery Devices in Human Volunteers*, Journal of Pharmacy and Pharmacology (Oct. 2004).
M. Kleven, *Using Computational Fluid Dynamics (CFD) to Improve the Bi-Directional Nasal Drug Delivery Concept*, Trans IChemE Part C. (Jun. 2005).
Per Gisle Djupesland, *Breath-Actuated Bi-Directional Delivery Sets the Nasal Market on a New Course*, ONdrugDelivery (Oct. 10, 2005).
Hilde Bakke et al., *Oral Spray Immunization May be an Alternative to Intranasal Vaccine Delivery to Induce Systemic Antibodies But Not Nasal Mucosal or Cellular Immunity*, Scan J. of Immunol. (Mar. 2006).
P.G. Djupesland et al., *Breath Actuated Nasal Device Improves Delivery to Target Sites Beyond the Nasal Valve*, The Laryngoscope (Mar. 2006).
R. Luthringer et al., *Rapid Absorption of Sumatriptan Powder and Effects on Glyceryl tinitrate Model of Headache Following Intranasal Delivery Using a Novel Bi-Directional Device*, Journal of Pharmacy and Pharmacology (Jan. 2009).
A. Skretting et al., *A New Method for Scintigraphic Quantification of Deposition and Clearance in Anatomical Regions of the Human Nose*, Nuclear Medicine Communications (Aug. 2009).
Vlckovia et al., *Effective Treatment of Mild-to-Moderate Nasal Polyposis with Fluticasone Delivered by a Novel Device*, Rhinology (Oct. 22, 2009).
Per Gisle Djupesland et al., *Impact of Baseline Nasal Polyp Size and Previous Surgery on Efficacy of Fluticasone Delivered With a Novel Device: A Subgroup Analysis*, Am. J. Rhinology Allergy (2010).
P.G. Djupesland et al., *Intranasal Sumatriptan Powder Delivered by a Novel Breath Actuated Bi-Directional Device for the Acute Treatment of Migraine: A Randomised Placebo-Controlled Study*, Cephalalgia (Mar. 17, 2010).
F.S. Hansen et al., *Preliminary Efficacy of Fluticasone Delivered by a Novel Device in Recalcitrant Chronic Rhinosinusitis*, Rhinology (Jun. 26, 2010).
Per Gisle Djupesland, *Nasal Drug Delivery Devices: Characteristics and Performance in Clinical Perspective—A Review*, Drug. Deliv. and Transl. Res. (Oct. 18, 2012).
Per Gisle Djupesland, *Nasal Deposition and Clearance in Man: Comparison of a Bidirectional Powder Device and a Traditional Liquid Spray Pump*, Journal of Aerosol Medicine and Pulmonary Drug Delivery (Nov. 2012).
Stewart J. Tepper, *Clinical Implications for Breath-Powered Powder Sumatriptan Intranasal Treatment*, Headache, The American Headache Society (Apr. 29, 2013).
Mohammad Obaidi et al., *Improved Pharmacokinetics of Sumatriptan With Breath Powered Nasal Delivery of Sumatriptan Powder*, Headache, The American Headache Society (May 24, 2013).
Per Gisle Djupesland, *Breath Powdered Nasal Delivery: A New Route to Rapid Headache Relief*, Headache, The American Headache Society (Jun. 4, 2013).
Per Gisle Djupesland et al., *The Nasal Approach to Delivering Treatment for Brain Diseases: An Anatomic, Physiologic, and Delivery Technology Overview*, Therapeutic Delivery (2014).
R.K. Cady et al., *A Randomized Double-Blind, Placebo Controlled Study of Breath Powered Nasal Delivery of Sumatriptan Powder (AVP-825) in the Treatment of Acute Migraine (The TARGET Study)*, Headache (Sept. 8, 2014).
S.J. Tepper et al., *AVP-825 Breath-Powdered Intranasal Delivery System Containing 22 mg Sumatriptan Powder vs. 100 mg Oral Sumatripta in the Acute Treatment of Migraines (The COMPASS Study): A Comparative Randomized Clinical Trial Across Multiple Attacks*, Headache: The Journal of Head and Face Pain (Mar. 29, 2015).
D. S. Quintana et al., *Low-dose Oxytocin Delivered Intranasally with Breath Powdered Device Affects Social-Cognitive Behavior: A Randomized Four-Way Crossover Trial with Nasal Cavity Dimension Assessment*, Transl Psychiatry (Jul. 14, 2015).
R. Mahmoud, *Breathe Out*, Innovations in Phar, Tech. (Dec. 10, 2015).
Einer-Jensen et al., *Intranasal Absorption of Sumatriptan and Naratriptan: No Evidence of Local Transfer from the Nasal Cavities to the Brain Arterial Blood in Male Rats*, 22 Biopharm, Drug Dispos. 213-219 (2001).
Fox, *Onset of Effect of 5-HT1B/1D Agonists: A Model with Pharmacokinetic Validation*, 44 Headache 142-147 (2004).
Chen et al., *Intranasal absorption of rizatriptan—in vivo pharmacokinetics and bioavailability study in humans*, 60 Pharmazie 39-41 (2005).
Edvinsson et al., *Triptan-induced contractile (5-HT1B receptor) responses in human cerebral and coronary arteries: relationship to clinical effect*, 109 Clinical Science 335-342 (2005).
Wang et al., *Uptake and biodistribution of rizatriptan to blood and brain following different routes of administration in rats*, 337 Int J Pharm 155-160 (2007).
Casale et al., "Intranasal noninhaled carbon dioxide for the symptomatic treatment of seasonal allergic rhinitis," J Allergy Clin Immunol, 121(1):105-109, (2008).
Egorova, "Intranasal glucocorticosteroid fluticasone propionate (Nazarel) in the treatment of allergic rhinitis," Seminars, www.atmophere-ph.ru, (2010).
Flonase® (fluticasone propionate), Nasal Spray, 50 mcg, pp. 1-18, accessed in Dec. 2017.
Holmberg et al., "Fluticasone propionate aqueous nasal spray in the treatment of nasal polyposis," Ann Allergy Asthma Immunol, 78(3):270-276, (1997).
Pukhalskaya et al., "Digidergot—New Opportunities for the Use of Digidroergotamine in Practice of Treatment of Migraine," Journal of Neurology, (1999).
Schusterman et al., "Real-time monitoring of nasal mucosal pH during carbon dioxide stimulation: implications for stimulus dynamics," Chem Senses, 28(7):595-601, (2003).
Tzabazis et al., "Trigeminal antihyperalgesic effect of intranasal carbon dioxide," Life Sci, 87(1-2):36-41, (2010).
English-Language Translation of JP 2003-40766 A, 5 pages.
English-Language Translation of CN 102580061 A, 15 pages.
English-Language Translation of Egorova, 4 pages.
English-Language Translation of Pukhalskaya et al., 5 pages.
G. Furness, *Nasal Drug Delivery: Rapid Onset via a Convenient Route*, ONdrugDelivery Ltd. (2005).
Travers et al., "Reference ranges for exhaled nitric oxide derived from a random community survey of adults," Am J Respir Crit Care Med, 176(3):238-242, (2007).
Shakhov et al., "Polypoid rhinosinusitis: a look at the pathogenesis and modern treatment technologies" (2014).
Casale et al., "Nasal carbon dioxide for the symptomatic treatment of perennial allergic rhinitis," Ann Allergy Asthma Immunol., 107:364-370 (2011).

\* cited by examiner

| Baseline attack grade | | Fraction | Response 30 minutes | | | | | | | Response 30 minutes | | | Pain relief (stand criteria) | | | Pain free 30 min | |
|---|---|---|---|---|---|---|---|---|---|---|---|---|---|---|---|---|---|
| | | | 1 step Episodes | 1 step Fraction | 2 steps Episodes | 2 steps Fraction | 3 steps Episodes | 3 steps Fraction | | 1-3steps | Fraction% | | Gr2/3→Gr1/0 | Fraction% | Pain free | | Fraction% |
| Mild | 197 | 45.2 | 33 | 16.8 | | | | | | 33 | 17 | | | | 33 | | 16.8 |
| Moderate | 203 | 46.6 | 87 | 42.9 | 29 | 14.3 | | | | 116 | 57 | | 116 | 57.1 | 29 | | 14 |
| Severe | 36 | 8.3 | 23 | 63.9 | 9.0 | 25.0 | 3.0 | 8.3 | | 35 | 97 | | 12 | 33.3 | 3 | | 8 |
| Total | 436 | 100 | 143 | | | | | | | 184 | 42.2 | | 128 | 53.6 | 65 | | 14.9 |

| Baseline attack grade | | Fraction | Response 120 minutes | | | | | | | Response 120 minutes | | | Pain relief (stand criteria) | | | Pain free 120min | |
|---|---|---|---|---|---|---|---|---|---|---|---|---|---|---|---|---|---|
| | | | 1 step Episodes | 1 step Fraction | 2 steps Episodes | 2 steps Fraction | 3 steps Episodes | 3 steps Fraction | | 1-3steps | Fraction% | | Gr2/3→Gr1/0 | Fraction% | Pain free (3/2/1→0) | | Fraction% |
| Mild | 146 | 45.2 | 94 | 64.0 | | | | | | 94 | 64 | | | | 94 | | 64 |
| Moderate | 151 | 46.6 | 124 | 82.0 | ? | ? | ? | ? | | 177 | 82 | | 177 | 82 | 77 | | 51.0 |
| Severe | 27 | 8.3 | ? | ? | ? | ? | ? | ? | | 27 | 100 | | 1 | 1 | 8 | | 29.9 |
| Total | 324 | 100 | | | | | | | | 298 | 91.9 | | 178 | 83.0 | 179 | | 55.2 |

FIG. 5

Sumatriptan Pharmacokinetic Results for Breath Powered Intranasal Delivery of Sumatriptan Powder Compared with 20 mg Nasal Spray, 100 mg Tablet and 6 mg Subcutaneous Injection

| PK Parameters | Sumatriptan Powder[a] Mean ± SD (n=20) | 20 mg Nasal Spray Mean ± SD (n=20) | 100 mg Oral Tablet Mean ± SD (n=20) | 6 mg S.C. Injection Mean ± SD (n=20) |
|---|---|---|---|---|
| $C_{max}$ (ng/mL) | 20.8 ± 12.2 | 16.4 ± 5.7 | 70.2 ± 25.3 | 111.6 ± 21.6 |
| $t_{max}$ (hr)[b] | 0.7 (0.2, 2.0) | 1.5 (0.2, 2.0) | 1.8 (0.5, 3.0) | 0.3 (0.2, 0.3) |
| $AUC_{0-t}$ (ng*hr/mL) | 63.0 ± 20.3 | 59.2 ± 17.7 | 292.6 ± 87.5 | 127.3 ± 17.3 |
| $AUC_{0-\infty}$ (ng*hr/mL) | 64.9 ± 20.6 | 61.1 ± 17.8 | 308.8 ± 92.4 | 128.2 ± 17.4 |
| $AUC_{0-15\,min}$ (ng*hr/mL) | 2.1 ± 1.6 | 1.2 ± 0.7 | 0.7 ± 0.7 | 16.2 ± 4.0 |
| $AUC_{0-30\,min}$ (ng*hr/mL) | 5.8 ± 4.1 | 3.6 ± 1.9 | 8.1 ± 5.0 | 39.7 ± 7.1 |
| $t_{½}$ (hr) | 3.1 ± 0.6 | 3.3 ± 0.9 | 3.8 ± 1.8 | 2.3 ± 0.4 |
| $\lambda_z$ | 0.2 ± 0.0 | 0.2 ± 0.1 | 0.2 ± 0.1 | 0.3 ± 0.0 |
| $AUC_{\%extrap}$ (%) | 3.0 ± 1.4 | 3.4 ± 2.3 | 5.2 ± 4.5 | 0.7 ± 0.3 |

[a] Sumatriptan powder delivered using the Breath Powered device, mean delivered dose 16 mg.
[b] $t_{max}$ is presented as median (minimum, maximum).
SD = standard deviation.

FIG. 8

Statistical Comparisons of Plasma Sumatriptan Pharmacokinetic Parameters a) Sumatriptan Powder vs. 20 mg Nasal Spray

| Parameter | Geometric LS Means | | % Geometric Mean Ratio | 90% Confidence Intervals | % Intra-subject CV |
|---|---|---|---|---|---|
| | Sumatriptan Powder (n=20) | 20 mg Nasal Spray (n=20) | | | |
| $C_{max}$ | 18.4 | 15.4 | 119.4 | (98.9, 144.1)* | 36.7 |
| $AUC_{0-t}$ | 60.1 | 56.5 | 106.4 | (93.8, 120.7) | 24.2 |
| $AUC_{0-30\ min}$ | 4.8 | 3.1 | 151.9 | (117.1, 197.0)* | 52.3 |
| $AUC_{0-\infty}$ | 61.9 | 58.4 | 106.0 | (93.6, 120.0) | 23.8 | b) Sumatriptan Powder vs. 100 mg Oral Tablet

| Parameter | Geometric LS Means | | % Geometric Mean Ratio | 90% Confidence Intervals | % Intra-subject CV |
|---|---|---|---|---|---|
| | Sumatriptan Powder (n=20) | 100 mg Oral Tablets (n=20) | | | |
| $C_{max}$ | 18.4 | 66.4 | 27.7 | (23.0, 33.4)* | 36.7 |
| $AUC_{0-t}$ | 60.1 | 280.9 | 21.4 | (18.9, 24.3)* | 24.2 |
| $AUC_{0-30\ min}$ | 4.8 | 6.9 | 68.5 | (52.8, 88.8)* | 52.3 |
| $AUC_{0-\infty}$ | 61.9 | 296.5 | 20.9 | (18.5, 23.7)* | 23.8 | c) Sumatriptan Powder vs 6 mg Subcutaneous Injection

| Parameter | Geometric LS Means | | % Geometric Mean Ratio | 90% Confidence Intervals | % Intra-subject CV |
|---|---|---|---|---|---|
| | Sumatriptan Powder (n=20) | 6 mg S.C. Injection (n=20) | | | |
| $C_{max}$ | 18.4 | 109.6 | 16.8 | (13.9, 20.2)* | 36.7 |
| $AUC_{0-t}$ | 60.1 | 126.2 | 47.6 | (42.0, 54.0)* | 24.2 |
| $AUC_{0-30\ min}$ | 4.8 | 39.1 | 12.2 | (9.4, 15.8)* | 52.3 |
| $AUC_{0-\infty}$ | 61.9 | 127.1 | 48.7 | (43.1, 55.2)* | 23.8 |

*Outside the boundary for bioequivalence (entire 90% CI within the range of 80-125%)
Parameters were ln-transformed prior to analysis.
Values for Sumatriptan Powder and 20 mg Nasal Spray are the exponentiated LS means from the ANOVA.
% Geometric Mean Ratio = 100*exp(LS mean test − LS mean reference).
% Intra-subject CV = 100*sqrt(exp($s^2$) − 1), where $s^2$ is the residual variance component from the ANOVA.

*FIG. 9*

| Parameter | OptiNose 7.5 mg (Nasal & mixed) GTN – side of migraine | OptiNose 15 mg (7.5 +7.5) (mixed) GTN – split between nostrils | OptiNose 6 mg sc injection GTN challenge | OptiNose 16 mg Nasal Peak | OptiNose 16 mg (mixed) | OptiNose 16 mg GI Peak | Imitrex NS 20 mg Nasal Peak | Imitrex NS 20 mg (mixed) | Imitrex NS 20 mg GI Peak | Optinose 6 mg sc injection |
|---|---|---|---|---|---|---|---|---|---|---|
| $C_{max}$ | 11.0 | 16.0 | 96.0 | 15.2 | 18.4 | 13.5 | 9.7 | 15.4 | 14.2 | 109.6 |
| | 20 min | 20 min | 10 min | 15 min | (45 min) | 120 min | 20 min | (90 min) | 120 min | 15 min |
| $AUC_{0-t}$ | | | | | 60.1 | | | 56.5 | | |
| $AUC_{0-30\ min}$ | | | | | 4.8 | | | 3.0 | | |
| $AUC_{0-\infty}$ | 37.0 | 49.0 | 106.7 | | 61.9 | | | 58.4 | | 127.1 |
| Relative BA PK1 GTN Challenge during migraine attack relative BA PK2 healthy volunteers | 27.7 | | | | 18.3 | | | 13.8 | | |
| | Migraineur | Migraineur | Migraineur | Healthy | Healthy | Healthy | Healthy | Healthy | Healthy | Healthy |

FIG. 10

| Drug (active dose)/study # in package insert | % Active | % Placebo | Therapeutic gain |
|---|---|---|---|
| Sumatripan (IMITREX, IMIGRAN Tabs) 100 mg Study 1 [18] | 62 | 27 | 35 |
| Sumatriptan (Suma) Tabs (100 mg) Study 2 [18] | 56 | 26 | 30 |
| Suma Tabs (100 mg) Study 3 [18] | 57 | 17 | 40 |
| Suma Injection (6 mg) Study 1 [19] | 70 | 21 | 49 |
| Suma Injection (6 mg) Study 2 [19] | 81 | 31 | 50 |
| Suma Injection (6 mg) Study 3 [19] | 82 | 39 | 43 |
| Suma Nasal Spray (20 mg) Study 1 [20] | 64 | 25 | 19 |
| Suma Nasal Spray (20 mg) Study 2 [20] | 55 | 25 | 30 |
| Suma Nasal Spray (20 mg) Study 3 [20] | 63 | 35 | 28 |
| Suma Nasal Spray (20 mg) Study 4 [20] | 62 | 29 | 33 |
| Suma Nasal Spray (20 mg) Study 5 [20] | 60 | 36 | 24 |
| Eletriptan (RELPAX) (40 mg) Study 1 [21] | 65 | 24 | 41 |
| Eletriptan (Ele) (40 mg) Study 2 [21] | 62 | 19 | 43 |
| Ele (40 mg) Study 3 [21] | 62 | 22 | 40 |
| Ele (40 mg) Study 4 [21] | 62 | 40 | 22 |
| Ele (40 mg) Study 5 [21] | 54 | 21 | 34 |
| Ele (40 mg) Study 6 [21] | 64 | 31 | 33 |
| Ele (40 mg) Study 7 [21] | 58 | 30 | 28 |
| Rizatriptan (MAXALT) (10 mg) Study 1 [16] | 71 | 35 | 36 |
| Rizatriptan (Riza) (10 mg) Study 2 [16] | 77 | 37 | 40 |
| Riza (10 mg) Study 4 [16] | 67 | 40 | 27 |
| Riza orally dissolvable tablet (MLT) [ODT] (10 mg) Study 5 [16] | 66 | 47 | 19 |
| Riza tab ODT 10 mg Study 6 [16] | 74 | 28 | 46 |
| Frovatriptan (FROVA) (2.5 mg) Study 1 [22] | 42 | 22 | 20 |
| Frovatriptan (FRV) (2.5 mg) Study 2 [22] | 38 | 25 | 13 |
| FRV (2.5 mg) Study 3 [22] | 39 | 21 | 18 |
| FRV (2.5 mg) Study 4 [22] | 46 | 27 | 19 |
| FRV (2.5 mg) Study 5 [22] | 37 | 23 | 14 |
| Sumatriptan Naproxen (TREXIMET) Study 1 [23] | 65 | 28 | 37 |
| Sumatriptan Naproxen (TRX) Study 2 [23] | 57 | 29 | 28 |
| Almotriptan (AXERT) (12.5 mg) Study 1 [24] | 58.5 | 33.8 | 24.7 |
| Almotriptan (Almo) (12.5 mg) Study 2 [24] | 57.1 | 40.0 | 17.1 |
| Almo 12.5 mg Study 3 [24] | 64.9 | 33.0 | 31.9 |
| Naratriptan (AMERGE, NARAMIG) 2.5 Study 1 [25] | 60 | 34 | 26 |
| Naratriptan (Nara) (2.5 mg) Study 2 [25] | 66 | 27 | 39 |
| Nara (2.5 mg) Study 3 [25] | 65 | 32 | 33 |
| Zolmitriptan (ZOMIG) Nasal Spray (5 mg) [26] | 69 | 31 | 38 |
| Zolmitriptan (Zolmi) Tabs (5 mg) Study 1 [27] | 60 | 16 | 44 |
| Zolmi Tabs (5 mg) Study 2 [27] | 66 | 19 | 47 |
| Zolmi Tabs (5 mg) Study 3 [27] | 67 | 34 | 28 |
| Zolmi Tabs (5 mg) Study 4 [27] | 59 | 44 | 15 |
| Zolmi ODT (ZMT) (2.5 mg) Study 6 [27] | 63 | 22 | 41 |
| Sumatriptan (OPTINOSE) Study 1 [9] | 80 | 44 | 36 |
| Breath-powered powder sumatriptan intranasal treatment (BPPSIT) Study 2 [10] | 68 | 45 | 23 |

FIG. 14

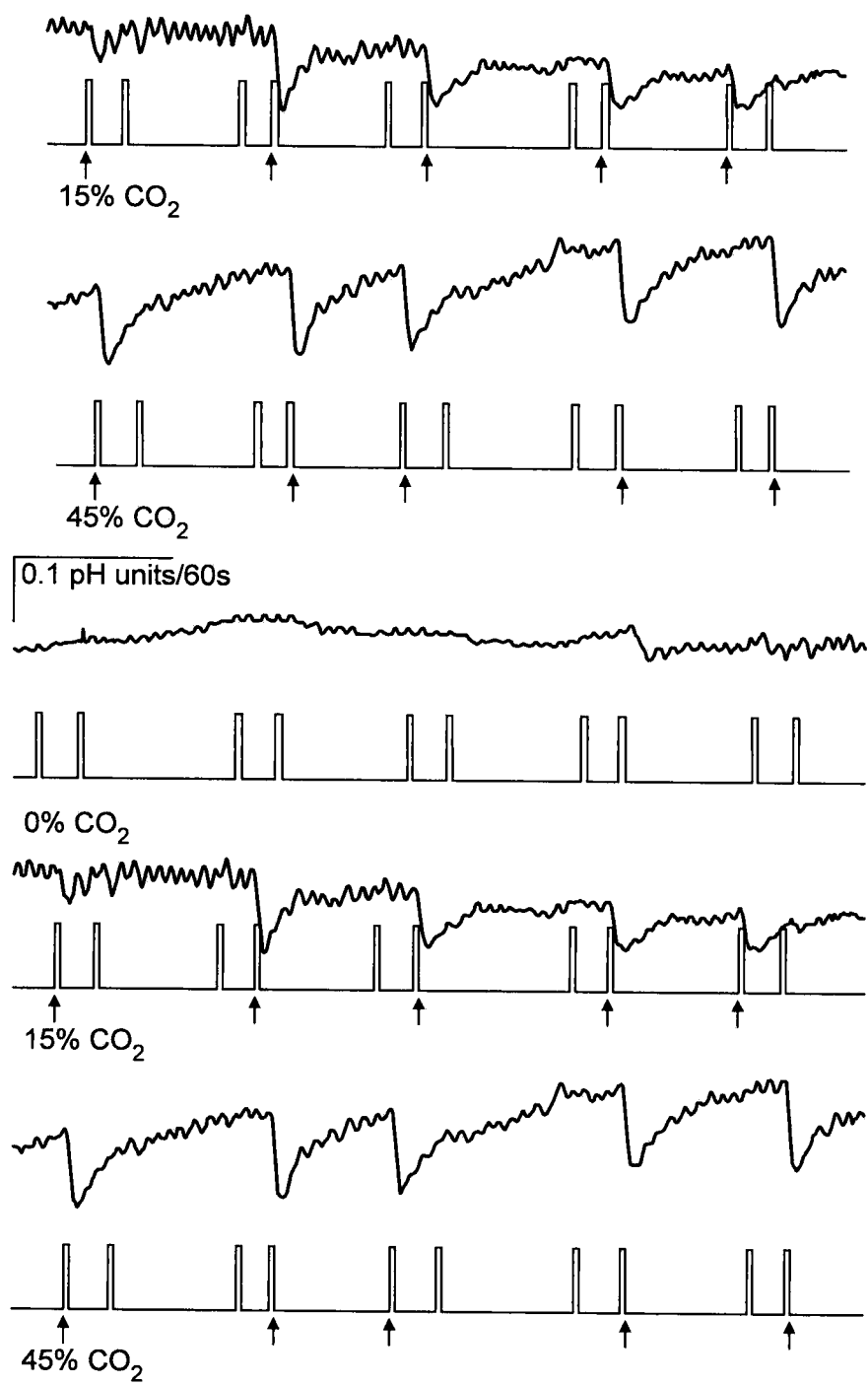

Example of real-time recording of nasal mucosal pH during pulsed stimulation with $CO_2$ (rectangular waves with arrows) and air (rectangular waves without arrows). Pulses are 5 l/min., 3.0 s duration, synchronized with inspiration, and delivered dichorhinically by nasal cannula. The first series of pulses were all control (0% $CO_2$) stimuli; vertical arrows in series 2 and 3 indicate $CO_2$ stimuli. Note baseline shift (as distinguished from phasic change) during control series (probably due to movement artifact). Subject is a 29 year old female.

FIG. 21

|  | Breath Powered Device (n=108) | Placebo device (n=104) | Total (n=212) |
|---|---|---|---|
| Patient Demographics | | | |
| Age (years), mean (SD) | 41.9 (10.3) | 42.0 (10.7) | 42.0 (10.5) |
| Sex, n (%) | | | |
|   Male | 17 (15.7) | 18 (17.3) | 35 (16.5) |
|   Female | 91 (84.3) | 86 (82.7) | 177 (83.5) |
| Caucasian race, n (%) | 90 (83.3) | 92 (88.5) | 182 (85.8) |
| Migraine History | | | |
| Attacks per month, mean (SD) | 4.3 (1.9) | 4.8 (1.9) | 4.5 (1.9) |
| Presence of (past 6 months) | | | |
|   Nausea | 90 (83.3) | 91 (87.5) | 181 (85.4) |
|   Vomiting | 42 (38.9) | 30 (28.8) | 72 (34.0) |
|   Photophobia | 106 (98.1) | 101 (97.1) | 207 (97.6) |
|   Phonophobia | 101 (93.5) | 92 (88.5) | 193 (91.0) |
| Characteristics of the Treated Headache at Baseline, n (%) | | | |
| Headache severity | | | |
|   Moderate pain | 90 (83.3) | 86 (82.7) | 176 (83.0) |
|   Severe pain | 18 (16.7) | 18 (17.3) | 36 (17.0) |
| Migraine type | | | |
|   Aura only | 1 (0.9) | 0 | 1 (0.5) |
|   With aura | 41 (38.0) | 34 (32.7) | 75 (35.4) |
|   Without aura | 85 (78.7) | 87 (83.7) | 172 (81.1) |
| Clinical disability scale | | | |
|   None | 2 (1.9) | 4 (3.8) | 6 (2.8) |
|   Daily activity mildly impaired | 44 (40.7) | 43 (41.3) | 87 (41.0) |
|   Daily activity moderately impaired | 55 (50.9) | 48 (46.2) | 103 (48.6) |
|   Daily activity severely impaired | 7 (6.5) | 9 (8.7) | 16 (7.5) |

[a]Patients may have had more than one of the listed symptoms.

FIG. 23

Demographic and Baseline Characteristics by Treatment Sequence
(Safety Analysis Set)

| | Sequence A/B (N=133) | Sequence B/A (N=129) | Total (N=262) |
|---|---|---|---|
| Age (years) | | | |
| n | 133 | 129 | 262 |
| Mean | 39.5 | 40.7 | 40.1 |
| SD | 12.55 | 11.93 | 12.24 |
| Median | 39.0 | 40.0 | 39.5 |
| Min, Max | 18, 64 | 18, 65 | 18, 65 |
| Sex, n (%) | | | |
| Male | 26 ( 19.5) | 14 ( 10.9) | 40 ( 15.3) |
| Female | 107 ( 80.5) | 115 ( 89.1) | 222 ( 84.7) |
| Race, n (%) | | | |
| American Indian/Alaskan Native | 0 | 0 | 0 |
| Asian | 3 ( 2.3) | 1 ( 0.8) | 4 ( 1.5) |
| Black/African American | 24 ( 18.0) | 26 ( 20.2) | 50 ( 19.1) |
| Native Hawaiian/Other Pacific Islander | 0 | 0 | 0 |
| White | 104 ( 78.2) | 100 ( 77.5) | 204 ( 77.9) |
| Other | 2 ( 1.5) | 2 ( 1.6) | 4 ( 1.5) |
| Ethnicity, n (%) | | | |
| Hispanic or Latino | 9 ( 6.8) | 10 ( 7.8) | 19 ( 7.3) |
| Not Hispanic or Latino | 124 ( 93.2) | 119 ( 92.2) | 243 ( 92.7) |
| Height (cm) | | | |
| n | 129 | 128 | 257 |
| Mean | 166.92 | 165.68 | 166.30 |
| SD | 8.686 | 6.992 | 7.897 |
| Median | 165.10 | 165.10 | 165.10 |
| Min, Max | 149.9, 188.5 | 149.9, 186.0 | 149.9, 188.5 |
| Weight (kg) | | | |
| n | 133 | 129 | 262 |
| Mean | 78.02 | 79.59 | 78.79 |
| SD | 20.892 | 18.531 | 19.743 |
| Median | 73.90 | 78.00 | 77.10 |
| Min, Max | 45.2, 173.7 | 43.0, 127.9 | 43.0, 173.7 |
| Average number of attacks per month [1] | | | |
| n | 133 | 129 | 262 |
| Mean | 4.8 | 4.9 | 4.9 |
| SD | 1.95 | 1.87 | 1.91 |
| Median | 4.0 | 5.0 | 4.0 |
| Min, Max | 2, 8 | 2, 8 | 2, 8 |

Note: A=20 mg OPTINOSE SUMATRIPTAN + Placebo Tablet; B=100 mg Sumatriptan Tablet + OPTINOSE Placebo.
[1] This applied to the 12 months prior to study entry.

FIG. 29

Primary Statistical Analysis of Mean SPID-30 by Treatment
(Full Analysis Set)

| | 20 mg OPTINOSE SUMATRIPTAN (N=185) | 100 mg Sumatriptan Tablets (N=185) |
|---|---|---|
| Unadjusted Mean SPID-30 | | |
| n | 185 | 185 |
| Mean (SD) | 10.71 (12.627) | 7.36 (11.224) |
| Median | 9.00 | 3.75 |
| Min, Max | -20.0, 60.0 | -20.0, 51.0 |
| Adjusted Mean SPID-30 | | |
| LS Mean (SE) | 10.80 (0.880) | 7.41 (0.880) |
| Adjusted Mean Difference (SE) | 3.39 (0.824) | |
| 95% CI | (1.76, 5.01) | |
| p-value | < 0.0001 | |

Note: Mean SPID-30 is defined as the mean area under the curve of the pain intensity differences from dosing to 30 minutes for each subject within period.
The Last Observation Carried Forward (LOCF) imputation method is used in this table.
Results are from an ANCOVA model with treatment, period, and treatment sequence as fixed effects, and subject as a random effect.

*FIG. 30*

Comparison of the Percent of Attacks with Pain Relief* between Treatments by Timepoint
(Full Analysis Set)

| Timepoint After Administration of the Study Drug | 20 mg OPTINOSE SUMATRIPTAN (N=185) | 100 mg Sumatriptan Tablets (N=185) | Odds Ratio | Estimates [1] 95% CI | P-value |
|---|---|---|---|---|---|
| Number of Attacks | 765 | 766 | | | |
| Baseline Intensity, n (%) [2] | | | | | |
| Moderate | 426 (55.7) | 435 (56.8) | | | |
| Severe | 83 (10.8) | 97 (12.7) | | | |
| Attacks With Pain Relief*, n (%) [3] | | | | | |
| At 10 minutes | 70 (13.8) | 61 (11.5) | 1.24 | [ 0.87, 1.77] | 0.2426 |
| At 15 minutes | 142 (27.9) | 111 (20.9) | 1.49 | [ 1.12, 1.99] | 0.0069 |
| At 30 minutes | 274 (53.8) | 206 (38.7) | 1.94 | [ 1.47, 2.56] | <.0001 |
| At 45 minutes | 331 (65.0) | 287 (53.9) | 1.68 | [ 1.26, 2.23] | 0.0004 |
| At 60 minutes | 367 (72.1) | 333 (62.6) | 1.60 | [ 1.22, 2.11] | 0.0008 |
| At 90 minutes | 394 (77.4) | 383 (72.0) | 1.38 | [ 1.04, 1.83] | 0.0272 |
| At 120 minutes | 405 (79.6) | 409 (76.9) | 1.21 | [ 0.90, 1.62] | 0.2085 |

Note: The Last Observation Carried Forward (LOCF) imputation method is used in this table.
Pain Relief * - defined as pain level reduced to none or mild.
[1] Odds Ratio, 95% CIs, and P-value are estimated by SAS Genmod procedure using the logit link with treatment, sequence, and period as fixed effects and a compound symmetry correlation structure within patient. Odds Ratio and 95% CI are for 20 mg OPTINOSE SUMATRIPTAN treatment versus 100 mg Sumatriptan Tablets.
[2] The percentage is based on the total number of attacks treated.
[3] The percentage is based on the total number of attacks treated when pain was moderate/severe.

FIG. 32

Comparison of the Percent of Attacks with Pain Freedom* between Treatments by Timepoint
All Attacks
(Full Analysis Set)

| Timepoint After Administration of the Study Drug | 20 mg OPTINOSE SUMATRIPTAN (N=185) | 100 mg Sumatriptan Tablets (N=185) | Estimates [1] | | |
|---|---|---|---|---|---|
| | | | Odds Ratio | 95% CI | P-Value |
| Number of Attacks | 765 | 766 | | | |
| Attacks With Pain Freedom*, n (%) | | | | | |
| At 10 minutes | 19 ( 2.5) | 10 ( 1.3) | 1.85 | [0.76, 4.54] | 0.1771 |
| At 15 minutes | 55 ( 7.2) | 28 ( 3.7) | 2.03 | [1.21, 3.42] | 0.0077 |
| At 30 minutes | 139 ( 18.2) | 83 ( 10.8) | 1.82 | [1.32, 2.50] | 0.0003 |
| At 45 minutes | 237 ( 31.0) | 163 ( 21.3) | 1.64 | [1.29, 2.09] | <.0001 |
| At 60 minutes | 315 ( 41.2) | 252 ( 32.9) | 1.41 | [1.14, 1.74] | 0.0016 |
| At 90 minutes | 404 ( 52.8) | 344 ( 44.9) | 1.36 | [1.09, 1.69] | 0.0059 |
| At 120 minutes | 462 ( 60.4) | 431 ( 56.3) | 1.14 | [0.91, 1.42] | 0.2717 |

Note: The Last Observation Carried Forward (LOCF) imputation method is used in this table.
Pain Freedom * - defined as pain level reduced to none [Grade 0].
The percentage is based on the total number of attacks.
[1] Odds Ratio, 95% CIs, and P-value are estimated by SAS Genmod procedure using the logit link with treatment, sequence, and period as fixed effects and a compound symmetry correlation structure within patient. Odds Ratio and 95% CI are for 20 mg OPTINOSE SUMATRIPTAN treatment versus 100 mg Sumatriptan Tablets.

FIG. 34

Comparison of the Percent of Attacks with Pain Reduction* between Treatments by Timepoint
All Attacks
(Full Analysis Set)

| Timepoint After Administration of the Study Drug | 20 mg OPTINOSE SUMATRIPTAN (N=185) | 100 mg Sumatriptan Tablets (N=185) | Odds Ratio | Estimates [1] 95% CI | P-Value |
|---|---|---|---|---|---|
| Number of Attacks | 765 | 766 | | | |
| Attacks With Pain Reduction*, n (%) | | | | | |
| At 10 minutes | 88 ( 11.5) | 78 ( 10.2) | 1.16 | [0.85, 1.60] | 0.3549 |
| At 15 minutes | 202 ( 26.4) | 150 ( 19.6) | 1.51 | [1.20, 1.90] | 0.0005 |
| At 30 minutes | 375 ( 49.0) | 270 ( 35.2) | 1.79 | [1.45, 2.21] | <.0001 |
| At 45 minutes | 464 ( 60.7) | 382 ( 49.9) | 1.56 | [1.24, 1.96] | 0.0002 |
| At 60 minutes | 514 ( 67.2) | 458 ( 59.8) | 1.37 | [1.10, 1.71] | 0.0057 |
| At 90 minutes | 571 ( 74.6) | 535 ( 69.8) | 1.26 | [0.99, 1.61] | 0.0654 |
| At 120 minutes | 597 ( 78.0) | 576 ( 75.2) | 1.15 | [0.89, 1.49] | 0.2894 |

Note: The Last Observation Carried Forward (LOCF) imputation method is used in this table.
Pain Reduction* - defined as a decrease in pain intensity of a least 1 point. The percentage is based on the total number of attacks.
[1] Odds Ratio, 95% CIs, and P-value are estimated by SAS Genmod procedure using the logit link with treatment, sequence, and period as fixed effects and a compound symmetry correlation structure within patient. Odds Ratio and 95% CI are for 20 mg OPTINOSE SUMATRIPTAN treatment versus 100 mg Sumatriptan Tablets.

FIG. 36

Comparison of the Percent of Attacks with Maintained Pain Free* between Treatments from 120 Minutes to 24 and 48 Hour
All Attacks
(Full Analysis Set)

| Timepoint After Administration of the Study Drug | 20 mg OPTINOSE SUMATRIPTAN (N=185) | 100 mg Sumatriptan Tablets (N=185) | Estimates [1] | | |
|---|---|---|---|---|---|
| | | | Odds Ratio | 95% CI | P-Value |
| Number of Attacks | 765 | 766 | | | |
| Attacks With Maintained Pain Free*, n (%) | | | | | |
| Over 24 Hours after the Attack | | | | | |
| Yes | 385 ( 50.3) | 369 ( 48.2) | 1.04 | [0.84, 1.27] | 0.7277 |
| No | 380 ( 49.7) | 397 ( 51.8) | | | |
| Over 48 Hours after the Attack | | | | | |
| Yes | 376 ( 49.2) | 356 ( 46.5) | 1.07 | [0.87, 1.30] | 0.5291 |
| No | 389 ( 50.8) | 410 ( 53.5) | | | |

Note: Maintained Pain Free* is defined as grade 0 from 120 mins to over 24, and 48 hours after the initial dose with no recurrence of headache, or rescue medication/second dose up to 24 hours and 48 hours.
The percentage is based on the total number of attacks.
[1] Odds Ratio, 95% CIs, and P-value are estimated by SAS Genmod procedure using the logit link with treatment, sequence, and period as fixed effects and a compound symmetry correlation structure within patient. Odds Ratio and 95% CI are for 20 mg OPTINOSE SUMATRIPTAN treatment versus 100 mg Sumatriptan Tablets.

FIG. 37

Comparison of the Percent of Attacks with Treatment Emergent Atypical Sensations within 120 Minutes between Treatments
Updated Questionnaire *
(Full Analysis Set)

|  | 20 mg OPTINOSE SUMATRIPTAN (N=185) | 100 mg Sumatriptan Tablets (N=185) | Estimates [1] | | |
| --- | --- | --- | --- | --- | --- |
|  |  |  | Odds Ratio | 95% CI | P-Value |
| Number of Attacks With Symptoms at Baseline | 105 | 107 |  |  |  |
| Number of Attacks Without Symptoms at Baseline | 512 | 512 |  |  |  |
| Attacks With Treatment Emergent Atypical Sensations, n (%) [2] Within 120 Minutes after the Attack | 10 ( 2.0%) | 27 ( 5.3%) | 0.40 | [0.19, 0.85] | 0.0176 |

Note: *Includes the symptoms in the chest, arms, hands or feet: warm/hot sensation, burning sensation, feeling of heaviness, pressure, feeling of tightness, numbness, or feeling strange.
[1] Odds Ratio, 95% CIs, and P-value are estimated by SAS Genmod procedure using the logit link with treatment, sequence, and period as fixed effects and a compound symmetry correlation structure within patient. Odds Ratio and 95% CI are for 20 mg OPTINOSE SUMATRIPTAN treatment versus 100 mg Sumatriptan Tablets.
[2] 'n' equals to the total number of attacks with atypical sensations, and the percentage (%) is based on the 'n' divided by the total number of attacks without symptoms at baseline * 100.

FIG. 38

NASAL ADMINISTRATION

This application claims the benefit of U.S. provisional application Ser. No. 61/805,400 filed Mar. 26, 2013 and U.S. utility application Ser. No. 14/226,287 filed Mar. 26, 2014, all of which is incorporated herein by reference in its entirety.

FIELD OF THE DISCLOSURE

The present disclosure, in one embodiment, relates to the nasal administration of substances, in particular drugs, and in particular substances which require a rapid onset of action, such as in the treatment of pain, including headaches, for example, cluster headaches and migraine, and neuropathic pain. The present disclosure also relates, in other embodiments, to nasal delivery of carbon dioxide gas, nasal removal of NO and/or nasal pH adjustment as a supplemental therapeutic treatment, which can, for example, provide for parasympathetic stimulation, such as for the treatment of pain.

SUMMARY OF THE DISCLOSURE

Referring to FIG. 1(a), the nasal airway 1 comprises the two nasal cavities separated by the nasal septum, which airway 1 includes numerous ostia, such as the paranasal sinus ostia 3 and the tubal ostia 5, and olfactory cells, and is lined by the nasal mucosa. The nasal airway 1 can communicate with the nasopharynx 7, the oral cavity 9 and the lower airway 11, with the nasal airway 1 being in selective communication with the anterior region of the nasopharynx 7 and the oral cavity 9 by opening and closing of the oropharyngeal velum 13. The velum 13, which is often referred to as the soft palate, is illustrated in solid line in the closed position, as achieved by providing a certain positive pressure in the oral cavity 9, such as achieved by balancing pressures in the oral cavity 9 and the nasal airway 1 on exhalation through the oral cavity 9, and in dashed line in the open position.

The present inventors have surprisingly identified that a rapid systemic uptake and a rapid response rate can be achieved, as compared, for example, to conventional delivery of an equivalent substance, by the delivery of substance and at least one gas to the posterior region of the nasal airway.

The posterior region of the nasal airway is that region which is posterior of the nasal valve NV, as illustrated in FIG. 1(b). The nasal valve comprises the anterior bony cavum which contains inferior turbinate erectile tissue and septal erectile tissue, which are supported respectively by compliant ala tissue and the rigid cartilaginous septum (Cole, P (The Respiratory Role of the Upper Airways, a selective clinical and pathophysiological review. 1993, Mosby-Year Book Inc. ISBN1.55664-390-X)). These elements combine to form a dynamic valve, which extends over several millimeters, that adjusts nasal airflow, and is stabilized by cartilage and bone, modulated by voluntary muscle and regulated by erectile tissue. The lumen of the nasal valve is the section of narrowest cross-sectional area between the posterior and anterior regions of the nasal airway, and is much longer and narrower dorsally than ventrally, and this lumen defines a triangular entrance which extends to the piriform region of the bony cavum. The nasal valve is lined in its anterior part with transitional epithelium, with a gradual transition posterior to respiratory epithelium. The nasal valve and anterior vestibule define roughly the anterior one-third of the nose.

The posterior region of the nasal airway is that region which is lined with respiratory epithelium, which is ciliated, and olfactory epithelium, which comprises nerves which extend downwards through the cribiform plate CP from the olfactory bulb, whereas the anterior region of the nasal airway is that region which is lined with squamous epithelium, which is not ciliated, and transitional epithelium. The olfactory epithelium extends on both the lateral and medial sides of the nasal airway, and typically extends downwards about 1.5 to 2.5 cm.

The upper posterior region is the region above the inferior meatus IM, as illustrated in FIG. 1(b), and encompasses the middle turbinate, the sinus ostia in infundibulum (ostia to maxillary, frontal and ethmoidal sinuses), the olfactory region, and the upper branches of the trigeminal nerve, and is that region which includes veins which drain to the venous sinuses that surround the brain.

As illustrated in FIG. 1(b), the posterior region of the nasal airway is the nasal region posterior of an imaginary vertical plane VERT1 which is located at a position corresponding to one-quarter of the distance between the anterior nasal spine AnS, which is a pointed projection at the anterior extremity of the intermaxillary suture, and the posterior nasal spine PnS, which is the sharp posterior extremity of the nasal crest of the hard palate and represents the transition between the nose and the nasopharynx, which corresponds to a distance posterior of the anterior nasal spine AnS of between about 13 mm and about 14 mm (Rosenberger, H (Growth and Development of the Naso-Respiratory Area in Childhood, PhD Thesis, Laboratory of Anatomy, School of Medicine, Western Reserve University, Presented to the Annual Meeting of the American Laryngological, Rhinological and Otological Society, Charleston, S.C., USA, 1934) defines the distance between the anterior nasal spine AnS and the posterior nasal spine PnS as being 56 mm in eighteen year old boys and 53.3 mm in eighteen year old girls). As again illustrated in FIG. 1(b), the posterior nasal region is bounded posteriorly by an imaginary vertical plane VERT2 which extends through the posterior nasal spine PnS.

As further illustrated in FIG. 1(b), the upper region of the nasal airway is an upper segment of the nasal airway which is bounded by the cribiform plate CP and a horizontal plane HORIZ which is located at a position corresponding to one-third of the distance between the nasal floor NF of the nasal airway and the cribiform plate CP, which corresponds to a height of typically between about 13 and about 19 mm above the nasal floor NF (Zacharek, M A et al (Sagittal and Coronal Dimensions of the Ethmoid Roof: A Radioanatomic Study, Am J Rhinol 2005, Vol 19, pages 348 to 352) define the distance from the nasal floor NF to the cribiform plate CP as 46+/−4 mm). The upper posterior region can thus include an upper posterior region which may be bounded by the above-defined vertical and horizontal planes VERT1, HORIZ.

Gas therapy for the treatment of headaches, allergies, asthma and other conditions as well as associated physiologies is described in the following references in the literature, including Casale et al, J Allergy Clin Immunol 121 (1): 105-109 (2008), Vause et al, Headache 47: 1385-1397 (2007), Tzabazis et al, Life Science 87: 36-41 (2010), and Casale et al, Ann Allergy Asthma Immunol 107: 364-370 (2011).

WO-A-2001/064280 discloses methods and devices for transcutaneous and transmucosal applications of carbon dioxide in the form of a gas and in the form of a capnic solution (such as carbonated water) for the relief of pain, including musculoskeletal disorders, neuralgias, rhinitis and other ailments.

US-A-2011/0046546 discloses apparatus, methods and kits for treating symptoms associated with common ailments, such as headaches, rhinitis, asthma, epilepsy, nervous disorders and the like.

The present inventors have recognized that the administration of a combination of a therapeutic substance, and control of pH, the intranasal gas pressure and/or NO concentration, such as by way of delivery of a gas through the nasal airway, can provide for an improved therapeutic treatment. In one embodiment control of pH, the intranasal gas pressure and/or NO concentration can provide for parasympathetic stimulation, which can provide for an additive effect or a synergistic effect, mediating uptake of a delivered therapeutic substance. In one example, a rapid onset of action of the therapeutic substance can be achieved.

In one aspect the present disclosure provides a method of administering a substance to a subject, comprising: delivering a substance to a posterior region of the nasal cavity of the subject, the posterior region comprising mucosa innervated by a trigeminal nerve; adjusting a pH of the mucosa, before, during or after the delivery of the substance, whereby a rate of uptake of the substance is increased.

In one embodiment the mucosa is also innervated by the sphenopalatine ganglion.

In one embodiment the substance is delivered through a nosepiece fitted to a nostril, optionally being a fluid-tight seal with a nare of the nostril.

In one embodiment the substance is delivered through a single nostril to the mucosa at one trigeminal nerve.

In one embodiment the substance is delivered successively through each of the nostrils to the mucosa at each of the trigeminal nerves.

In one embodiment the pH is adjusted by delivery of at least one gas.

In one embodiment the at least one gas is delivered in a flow, optionally having a concentration of at least 5 vol % of the at least one gas.

In one embodiment the at least one gas comprises carbon dioxide.

In one embodiment adjustment of the pH mediates activity at the V1 branch of the trigeminal nerve.

In one embodiment the pH adjustment is performed during an event in which there is a parasympathaetic influence on the autonomic nervous system, by which the trigeminal nerve is predisposed to the pH adjustment and uptake of substance is increased.

In one embodiment the pH is reduced in the pH adjustment.

In one embodiment the method further comprises: adjusting a pressure in the nasal cavity before, during or after the delivery of the substance, whereby a rate of uptake of the substance is increased.

In one embodiment the pressure is at least about 3 kPa, optionally from about 3 to about 7 kPa.

In one embodiment the pressure is adjusted by delivery of at least one gas.

In one embodiment, the at least one gas is delivered in a flow, optionally having a concentration of at least 5 vol % of the at least one gas.

In one embodiment, the at least one gas comprises carbon dioxide.

In one embodiment the pressure adjustment mediates activity at the V1 branch of the trigeminal nerve.

In one embodiment the pressure adjustment is performed during an event in which there is a parasympathaetic influence on the autonomic nervous system, by which the trigeminal nerve is predisposed to the pressure adjustment and uptake of substance is increased.

In one embodiment the pressure is increased in the pressure adjustment.

In one embodiment the method further comprises: adjusting a concentration of NO in the nasal cavity before, during or after the delivery of the substance, whereby a rate of uptake of the substance is increased.

In one embodiment the NO concentration is adjusted by delivery of at least one gas.

In one embodiment the at least one gas is delivered in a flow, optionally having a concentration of at least 5 vol % of the at least one gas.

In one embodiment the at least one gas comprises carbon dioxide.

In one embodiment adjustment of the NO concentration mediates activity at the V1 branch of the trigeminal nerve.

In one embodiment the NO concentration is decreased in the NO concentration adjustment.

In one embodiment the substance is a substance which does not pass the blood-to-brain barrier.

In one embodiment the substance is a triptan. In one embodiment the substance is sumatriptan.

In another embodiment the substance is an ergot alkaloid. In one embodiment the substance is an ergotamine or an analogue or derivative thereof, such as dihydroergotamine.

In one embodiment the method is for the treatment of a neurological or CNS disorder.

In one embodiment the method is for the treatment of headache, including cluster headache and migraine.

In one embodiment the method further comprises: closing the oropharyngeal velum of the subject during delivery of the substance and/or the at least one gas.

In one embodiment the method further comprises: the subject exhaling through a mouthpiece to cause closure of the oropharyngeal velum of the subject.

In one embodiment the mouthpiece is fluidly connected to a nosepiece, whereby exhaled air from an exhalation breath is delivered through the nosepiece.

In another aspect the present disclosure provides a method of administering a substance to a subject, comprising: delivering a substance to a posterior region of the nasal cavity of the subject, the posterior region comprising mucosa innervated by a trigeminal nerve; adjusting a pressure in the nasal cavity before, during or after the delivery of the substance, whereby a rate of uptake of the substance is increased.

In one embodiment the mucosa is also innervated by the sphenopalatine ganglion.

In one embodiment the substance is delivered through a nosepiece fitted to a nostril, optionally being a fluid-tight seal with a nare of the nostril.

In one embodiment, the substance is delivered through a single nostril to the mucosa at one trigeminal nerve.

In one embodiment the substance is delivered successively through each of the nostrils to the mucosa at each of the trigeminal nerves.

In one embodiment the pressure is adjusted by delivery of at least one gas.

In one embodiment the at least one gas is delivered in a flow, optionally having a concentration of at least 5 vol % of the at least one gas.

In one embodiment the at least one gas comprises carbon dioxide.

In one embodiment adjustment of the pressure mediates activity at the V1 branch of the trigeminal nerve.

In one embodiment the pressure adjustment is performed during an event in which there is a parasympathaetic influence on the autonomic nervous system, by which the trigeminal nerve is predisposed to the pressure adjustment and uptake of substance is increased.

In one embodiment the pressure is at least about 3 kPa, optionally from about 3 to about 7 kPa.

In one embodiment the pressure is increased in the pressure adjustment.

In one embodiment the method further comprises: adjusting a concentration of NO in the nasal cavity before, during or after the delivery of the substance, whereby a rate of uptake of the substance is increased.

In one embodiment the NO concentration is adjusted by delivery of at least one gas.

In one embodiment the at least one gas is delivered in a flow, optionally having a concentration of at least 5 vol % of the at least one gas.

In one embodiment the at least one gas comprises carbon dioxide.

In one embodiment adjustment of the NO concentration mediates activity at the V1 branch of the trigeminal nerve.

In one embodiment the NO concentration is decreased in the NO concentration adjustment.

In one embodiment the substance is a substance which does not pass the blood-to-brain barrier.

In one embodiment the substance is a triptan. In one embodiment the substance is sumatriptan.

In another embodiment the substance is an ergot alkaloid. In one embodiment the substance is an ergotamine or an analogue or derivative thereof, such as dihydroergotamine.

In one embodiment the method is used in the treatment of a neurological or CNS disorder.

In one embodiment the method is for the treatment of headache, including cluster headache and migraine.

In one embodiment the method further comprises: closing the oropharyngeal velum of the subject during delivery of the substance and/or the at least one gas.

In one embodiment the method further comprises: the subject exhaling through a mouthpiece to cause closure of the oropharyngeal velum of the subject.

In one embodiment the mouthpiece is fluidly connected to a nosepiece, whereby exhaled air from an exhalation breath is delivered through the nosepiece.

In a further aspect the present disclosure provides a method of administering a substance to a subject, comprising: delivering a substance to a posterior region of the nasal cavity of the subject, the posterior region comprising mucosa innervated by a trigeminal nerve; adjusting a concentration of NO in the nasal cavity before, during or after the delivery of the substance, whereby a rate of uptake of the substance in increased.

In one embodiment the mucosa is also innervated by the sphenopalatine ganglion.

In one embodiment the substance is delivered through a nosepiece fitted to a nostril, optionally being a fluid-tight seal with a nare of the nostril.

In one embodiment the substance is delivered through a single nostril to the mucosa at one trigeminal nerve.

In one embodiment the substance is delivered successively through each of the nostrils to the mucosa at each of the trigeminal nerves.

In one embodiment the NO concentration is adjusted by delivery of at least one gas.

In one embodiment the at least one gas is delivered in a flow, optionally having a concentration of at least 5 vol % of the at least one gas.

In one embodiment the at least one gas comprises carbon dioxide.

In one embodiment adjustment of the NO concentration mediates activity at the V1 branch of the trigeminal nerve.

In one embodiment the NO concentration is decreased in the NO concentration adjustment.

In one embodiment the method further comprises: adjusting a pH of the mucosa, before, during or after the delivery of the substance, whereby a rate of uptake of the substance is increased.

In one embodiment the pH is adjusted by delivery of at least one gas.

In one embodiment the at least one gas is delivered in a flow, optionally having a concentration of at least 5 vol % of the at least one gas.

In one embodiment the at least one gas comprises carbon dioxide.

In one embodiment adjustment of the pH mediates activity at the V1 branch of the trigeminal nerve.

In one embodiment the pH adjustment is performed during an event in which there is a parasympathaetic influence on the autonomic nervous system, by which the trigeminal nerve is predisposed to the pH adjustment and uptake of substance is increased.

In one embodiment the pH is reduced in the pH adjustment.

In one embodiment the method further comprises: adjusting a pressure in the nasal cavity before, during or after the delivery of the substance, whereby a rate of uptake of the substance is increased.

In one embodiment the pressure is at least about 3 kPa, optionally from about 3 to about 7 kPa.

In one embodiment the pressure is adjusted by delivery of at least one gas.

In one embodiment the at least one gas is delivered in a flow, optionally having a concentration of at least 5 vol % of the at least one gas.

In one embodiment the at least one gas comprises carbon dioxide.

In one embodiment the pressure adjustment mediates activity at the V1 branch of the trigeminal nerve.

In one embodiment the pressure adjustment is performed during an event in which there is a parasympathetic influence on the autonomic nervous system, by which the trigeminal nerve is predisposed to the pressure adjustment and uptake of substance is increased.

In one embodiment the pressure is increased in the pressure adjustment.

In one embodiment the substance is a substance which does not pass the blood-to-brain barrier.

In one embodiment the substance is a triptan. In one embodiment the substance is sumatriptan.

In another embodiment the substance is an ergot alkaloid. In one embodiment the substance is an ergotamine or an analogue or derivative thereof, such as dihydroergotamine.

In one embodiment the method is used in the treatment of a neurological or CNS disorder, in one embodiment in the treatment of headache, including cluster headache and migraine.

In one embodiment the method further comprises: closing the oropharyngeal velum of the subject during delivery of the substance and/or the at least one gas.

In one embodiment the method further comprises: the subject exhaling through a mouthpiece to cause closure of the oropharyngeal velum of the subject.

In one embodiment the mouthpiece is fluidly connected to a nosepiece, whereby exhaled air from an exhalation breath is delivered through the nosepiece.

In a still further aspect the present disclosure provides a method of administering a substance to a subject, comprising: delivering a substance to a posterior region of the nasal cavity of the subject, the posterior region comprising mucosa innervated by a trigeminal nerve; adjusting a pH of the mucosa before, during or after the delivery of a substance; and adjusting a pressure in the nasal cavity before, during or after the delivery of the substance, whereby a rate of uptake of the substance is increased.

In yet another aspect the present disclosure provides a method of administering a substance to a subject, comprising: delivering a substance to a posterior region of the nasal cavity of the subject, the posterior region comprising mucosa innervated by a trigeminal nerve; adjusting a pH of the mucosa before, during or after the delivery of a substance; and adjusting a concentration of NO in the nasal cavity before, during or after the delivery of the substance, whereby a rate of uptake of the substance is increased.

In still another aspect the present disclosure provides a method of administering a substance to a subject, comprising: delivering a substance to a posterior region of the nasal cavity of the subject, the posterior region comprising mucosa innervated by a trigeminal nerve; adjusting a pressure in the nasal cavity before, during or after the delivery of the substance; and adjusting a concentration of NO in the nasal cavity before, during or after the delivery of the substance, whereby a rate of uptake of the substance in increased.

In still another aspect the present disclosure provides a method of administering a substance to a subject, comprising: delivering a substance to a posterior region of the nasal cavity of the subject, the posterior region comprising mucosa innervated by a trigeminal nerve; adjusting a pH of the mucosa before, during or after the delivery of the substance; and adjusting a pressure in the nasal cavity before, during or after the delivery of the substance; and adjusting a concentration of NO in the nasal cavity before, during or after the delivery of the substance, whereby a rate of uptake of the substance is increased.

In a yet further aspect the present disclosure provides a substance for treating a neurological or CNS disorder, wherein the substance is delivered to a posterior region of the nasal cavity of a subject, the posterior region comprising mucosa innervated by a trigeminal nerve; and wherein a pH of the mucosa is adjusted before, during or after the delivery of the substance, whereby a rate of uptake of the substance is increased.

In a still yet further aspect the present disclosure provides substance for treating a neurological or CNS disorder, wherein the substance is delivered to a posterior region of the nasal cavity of a subject, the posterior region comprising mucosa innervated by a trigeminal nerve; and wherein a pressure in the nasal cavity is adjusted before, during or after the delivery of the substance, whereby a rate of uptake of the substance is increased.

In yet still another aspect the present disclosure provides a substance for treating a neurological or CNS disorder, wherein the substance is delivered to a posterior region of the nasal cavity of a subject, the posterior region comprising mucosa innervated by a trigeminal nerve; and wherein a concentration of NO in the nasal cavity is adjusted before, during or after the delivery of the substance, whereby a rate of uptake of the substance is increased.

In one embodiment the substance is a triptan. In one embodiment the substance is sumatriptan.

In another embodiment the substance is an ergot alkaloid. In one embodiment the substance is an ergotamine or an analogue or derivative thereof, such as dihydroergotamine.

In one aspect the substance is for the treatment of headache, including cluster headache and migraine.

In a further aspect the present disclosure provides a method of administering a substance to a subject, comprising: delivering a substance to a subject; adjusting a pressure in the nasal cavity before, during or after the delivery of the substance, whereby a rate of uptake of the substance is increased.

In yet another aspect the present disclosure provides a method of administering a substance to a subject, comprising: delivering a substance to a subject; adjusting a concentration of NO in the nasal cavity before, during or after the delivery of the substance, whereby a rate of uptake of the substance is increased.

In a yet further aspect the present disclosure provides a method of administering a substance to a subject, comprising: delivering a substance to a subject; adjusting a pH of the mucosa innervated by a trigeminal nerve before, during or after the delivery of the substance, whereby a rate of uptake of the substance is increased.

In one embodiment the delivery is peroral, topical, transmucosal, inhalation and/or injection, sub-cutaneous, nasal and/or oral.

In a further aspect the present disclosure provides a method of administering a substance to a subject, comprising: delivering a first substance that induces a migraine; and delivering a second substance according to any of the methods disclose above.

In accordance with the disclosure an embodiment is directed to a method of therapeutically treating a patient. The method can include administering, in a first step, a therapeutic agent, and delivering, in a second step, to a location at an interior of a nasal passage of the patient, a therapeutic amount of at least one of carbon dioxide or a pH adjusting material.

Another embodiment is directed to a method for increasing a therapeutic effect of a pharmaceutical agent delivered to a patient. The method can include delivering a fluid flow to a nasal passage of the patient to deliver about 5% to about 6% vol/vol carbon dioxide to an upper posterior region of the nasal passage. The method can also include administering a dose of the pharmaceutical agent to the patient.

Yet another embodiment is directed to a method of treating a patient that includes delivering about 5% to about 6% vol/vol carbon dioxide to a nostril of the patient to lower a pH of an upper posterior region of the nasal passage by at least about 0.1 pH units to provide a therapeutic effect.

Additional objects and advantages of the disclosure will be set forth in part in the description which follows, and in part will be obvious from the description, or may be learned by practice of the disclosure. The objects and advantages of the disclosure will be realized and attained by means of the elements and combinations particularly pointed out in the appended claims.

It is to be understood that both the foregoing general description and the following detailed description are exemplary and explanatory only and are not restrictive of the disclosure as claimed.

The accompanying drawings, which are incorporated in and constitute a part of this specification, together with the description describe various embodiments of the disclosure, which are by way of example and serve to explain the principles of the disclosure.

BRIEF DESCRIPTION OF THE DRAWINGS

FIG. 5 illustrates response rates for the study of Example #1;

Figure 6:
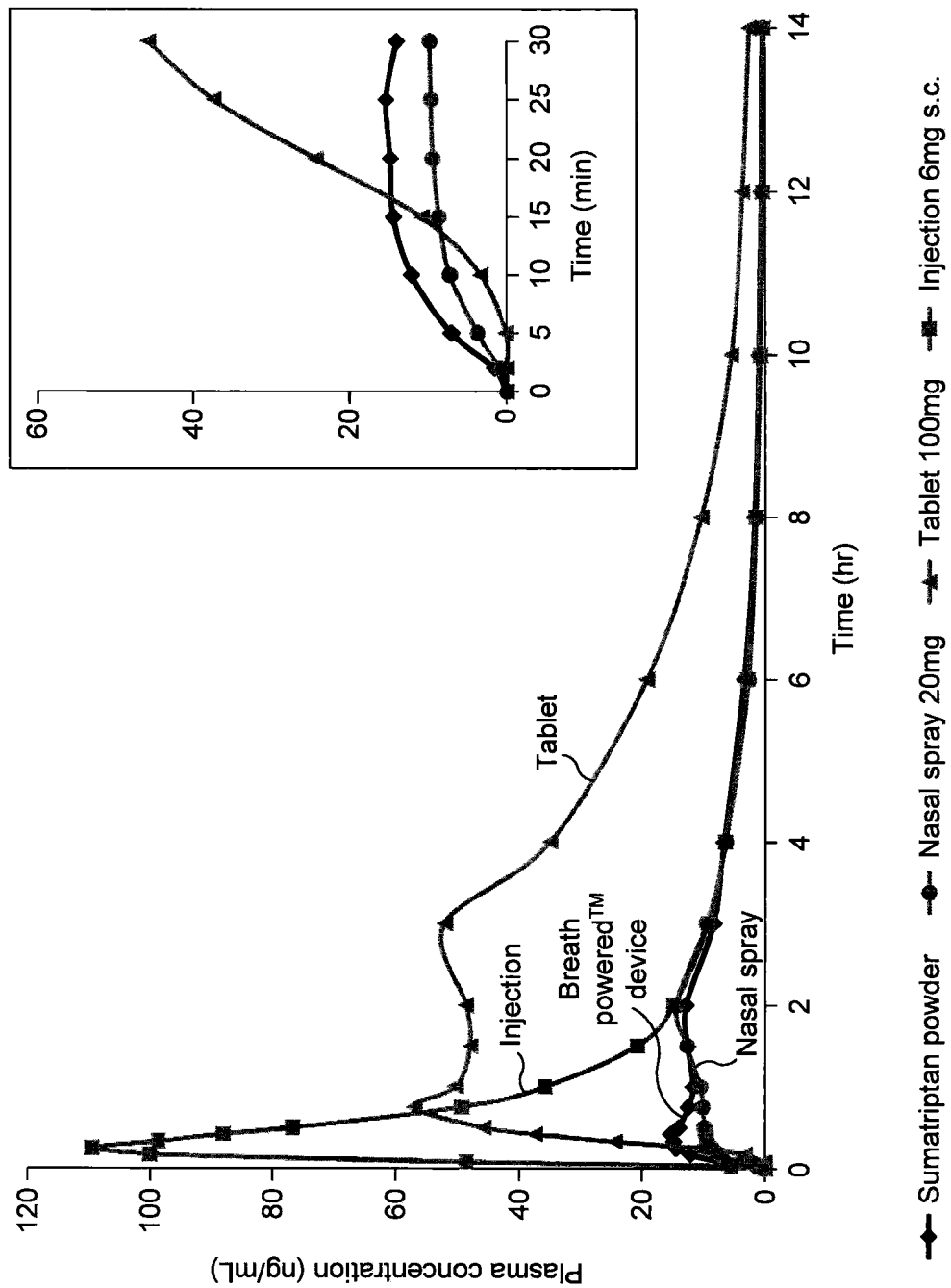
FIG. 6 illustrates sumatriptan plasma concentration-time profiles over a 14 hr sampling period for intranasal sumatriptan powder delivered using the Breath Powered™ device of FIGS. 2(a) and (b), 20 mg nasal spray, 100 mg tablet and 6 mg sub-cutaneous injection, and inset for intranasal sumatriptan powder delivered using the Breath Powered™ device of FIGS. 2(a) and (b), 20 mg nasal spray and 100 mg tablet over the first 30 mins post-dose, for the study of Example #2.

The main part of FIG. 6 shows that both methods of intranasal delivery resulted in much lower mean plasma sumatriptan concentration-time profiles than observed for the tablet and the injection. The inset in FIG. 6 illustrates, in the first 30 mins post-dose, that the rate of increase in the plasma sumatriptan concentration was faster for sumatriptan powder delivered using the Breath Powered™ device of FIGS. 2(a) and (b) than either the 20 mg nasal spray or the 100 mg tablet.

Figure 1A:
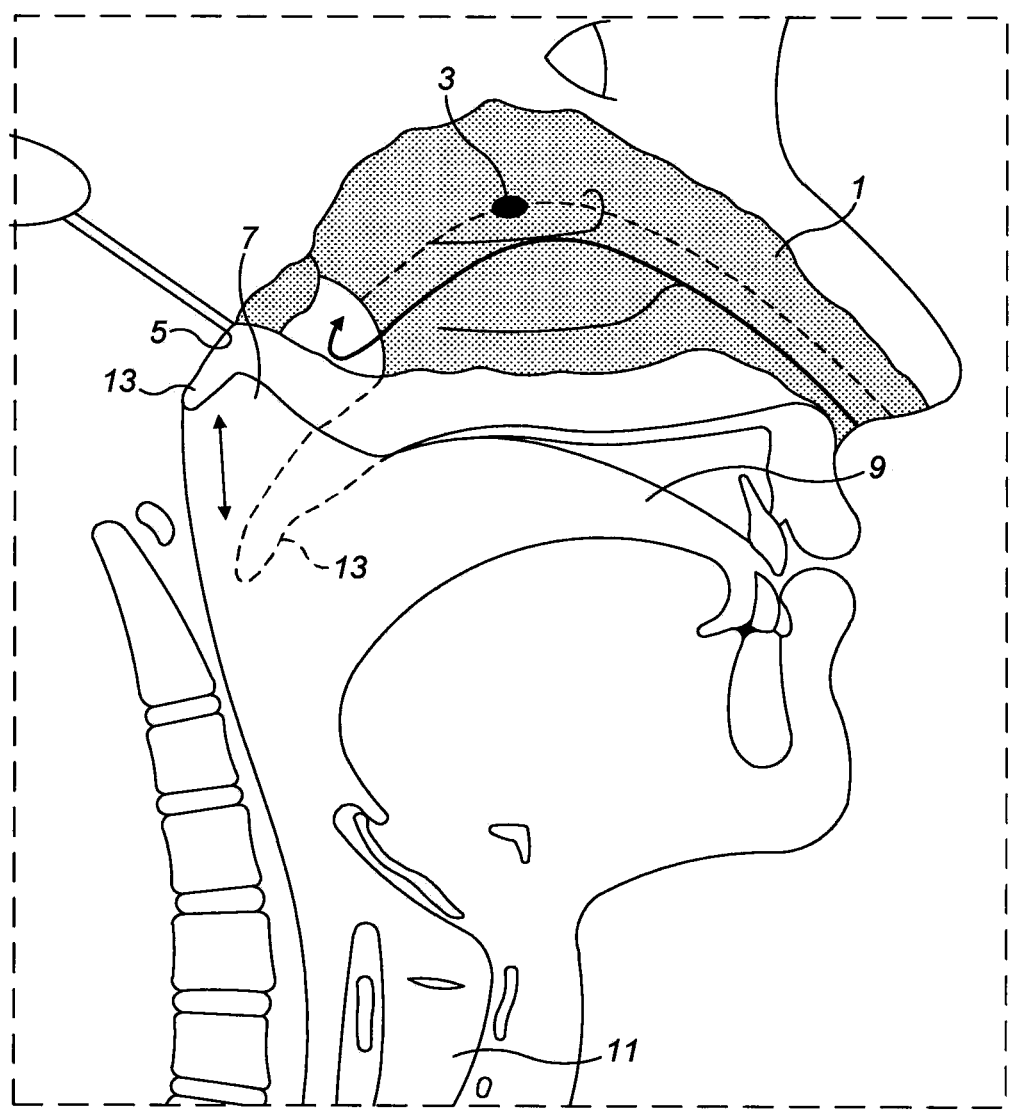
FIG. 1(a) schematically illustrates the anatomy of the upper respiratory tract of a human subject.
Figure 1B:
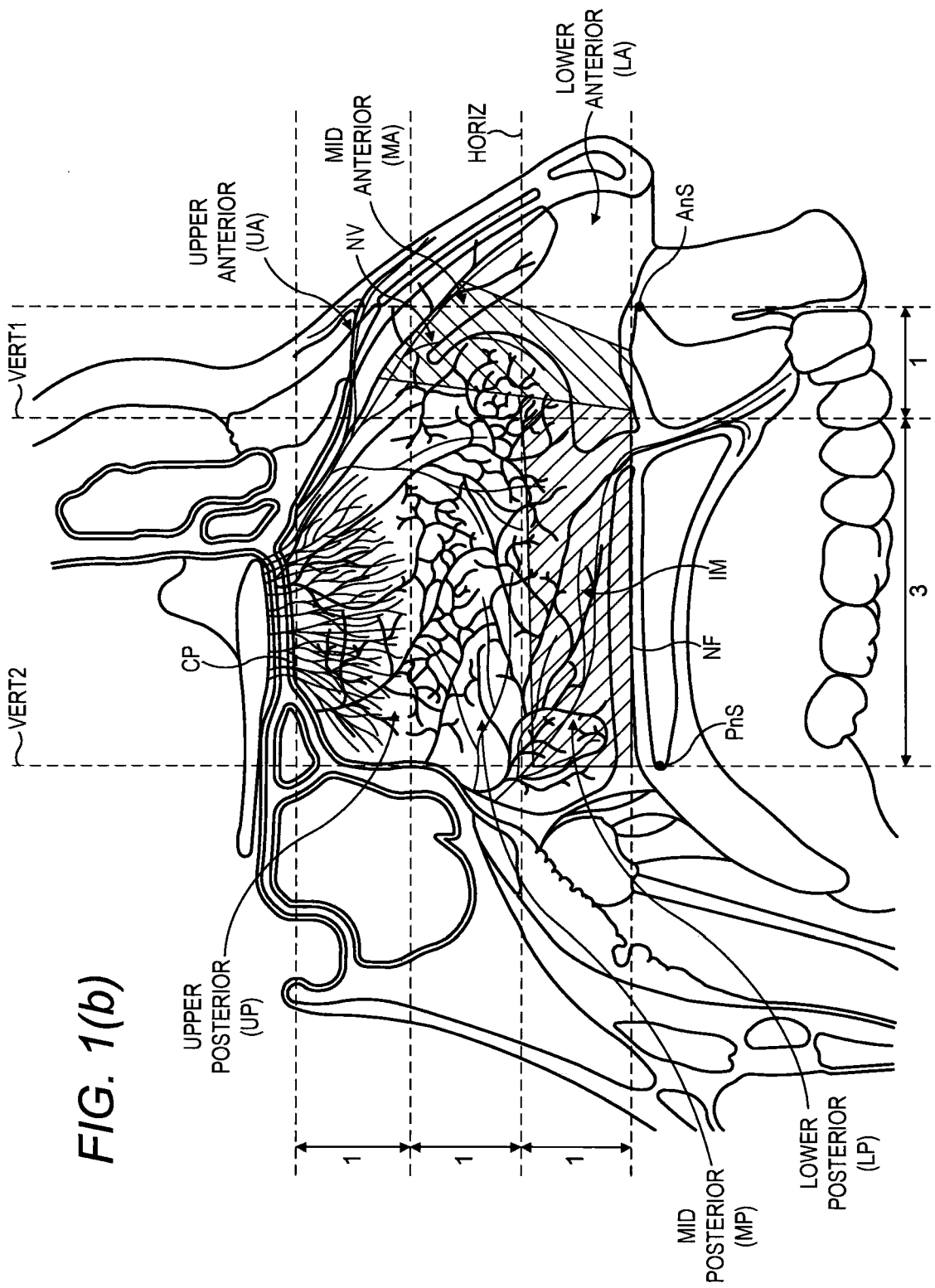
FIG. 1(b) illustrates the segmentation of a nasal cavity in accordance with an embodiment of the present disclosure.
Figure 2A:
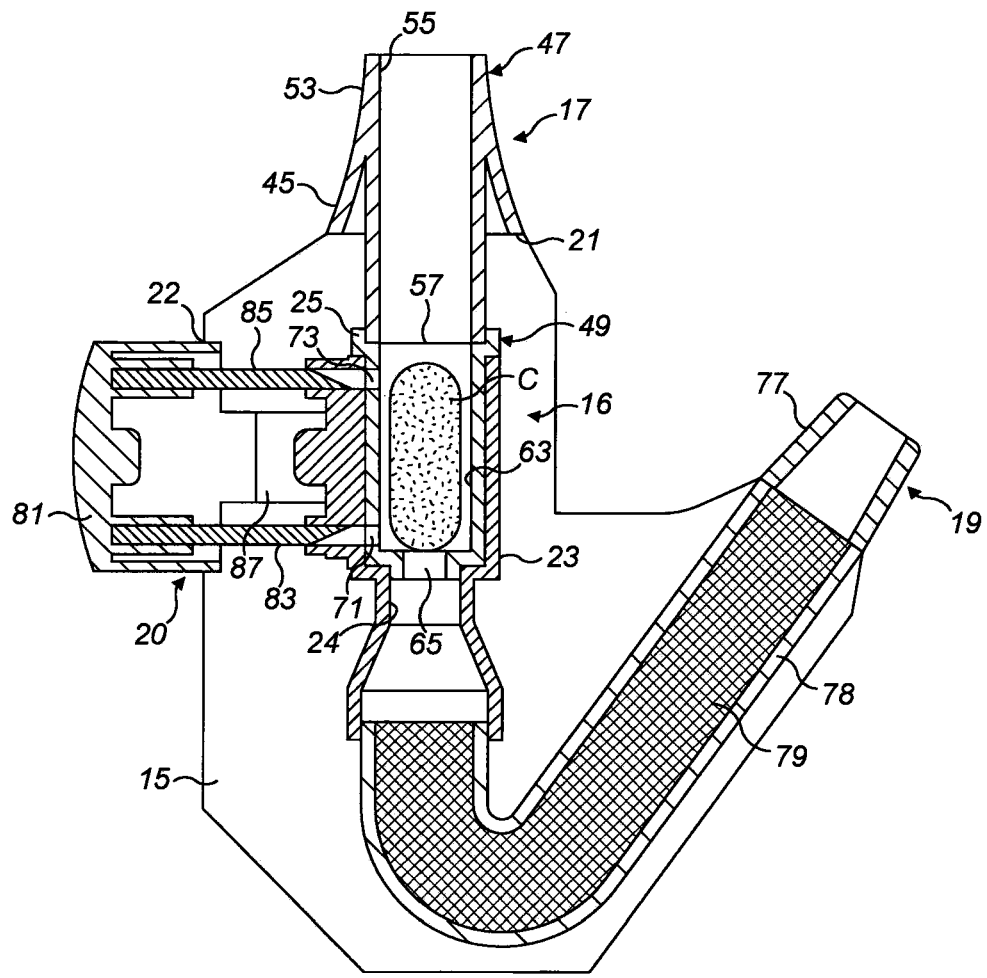
FIGS. 2(a) and (b) illustrate a Breath Powered™ Bi-Directional™ nasal delivery device in accordance with one embodiment of the present disclosure.
Figure 3A:
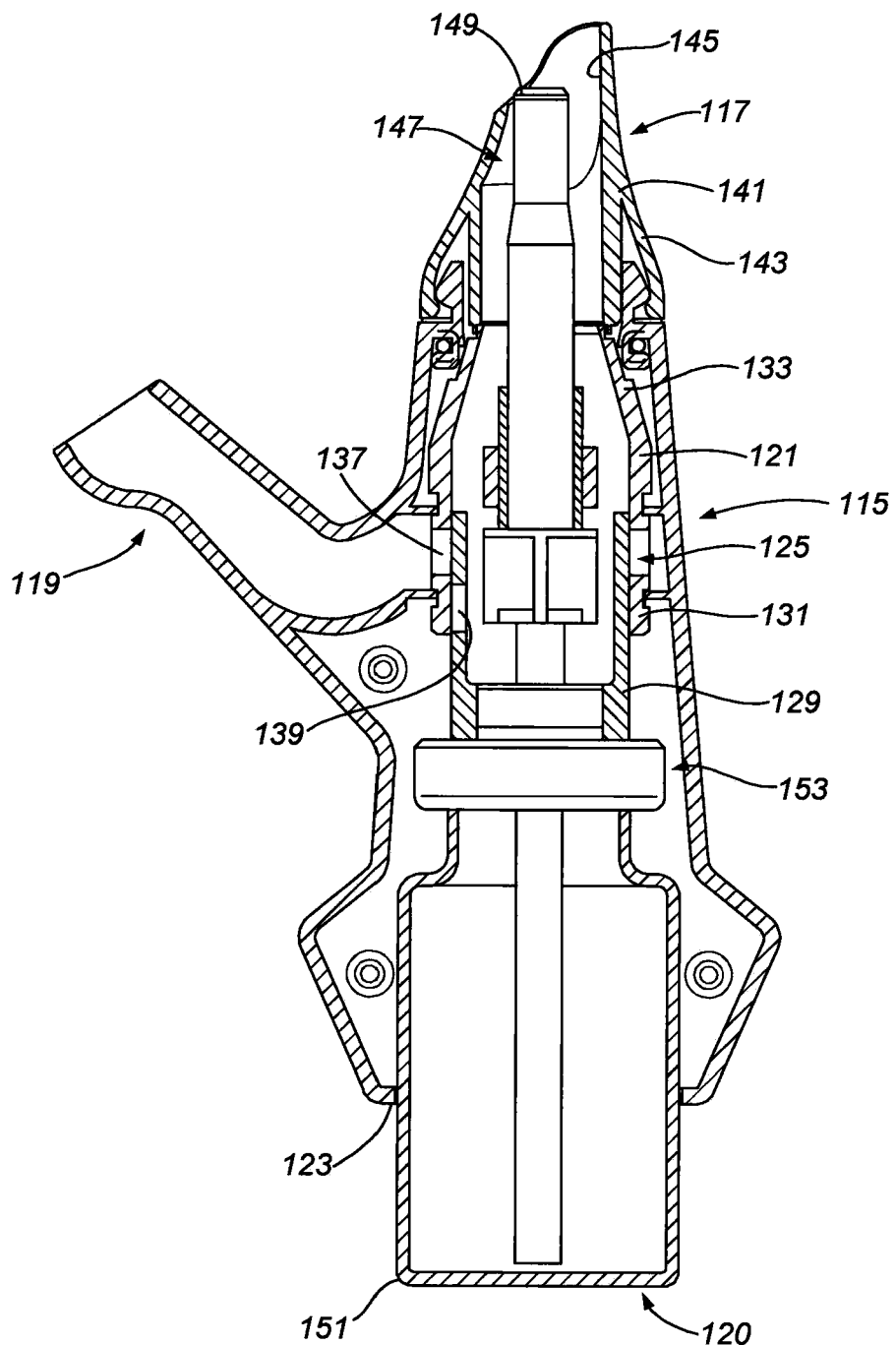
FIGS. 3(a) and (b) illustrate a Breath Powered™ Bi-Directional™ nasal delivery device in accordance with another embodiment of the present disclosure.
Figure 3B:
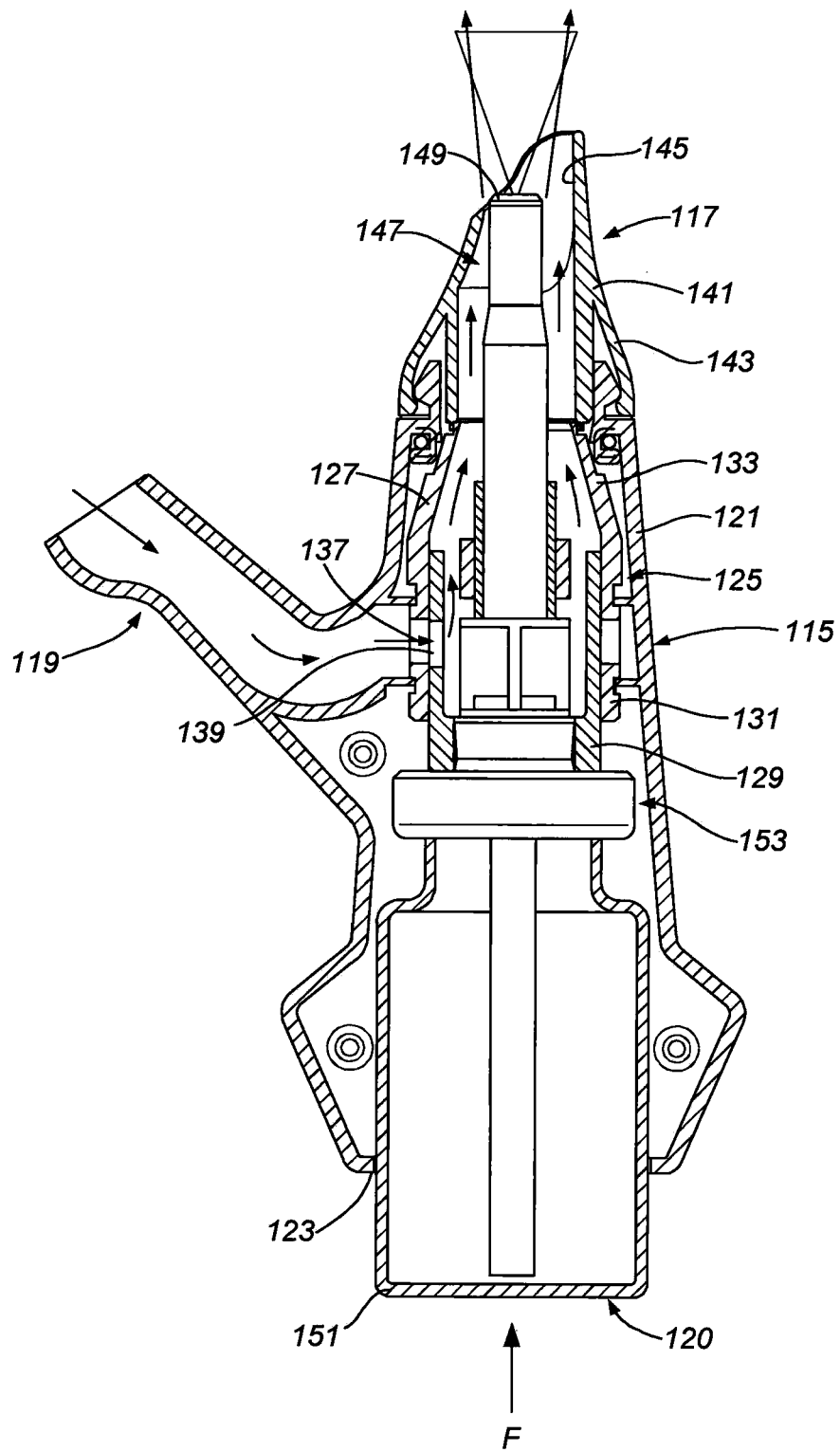
Figure 4A:
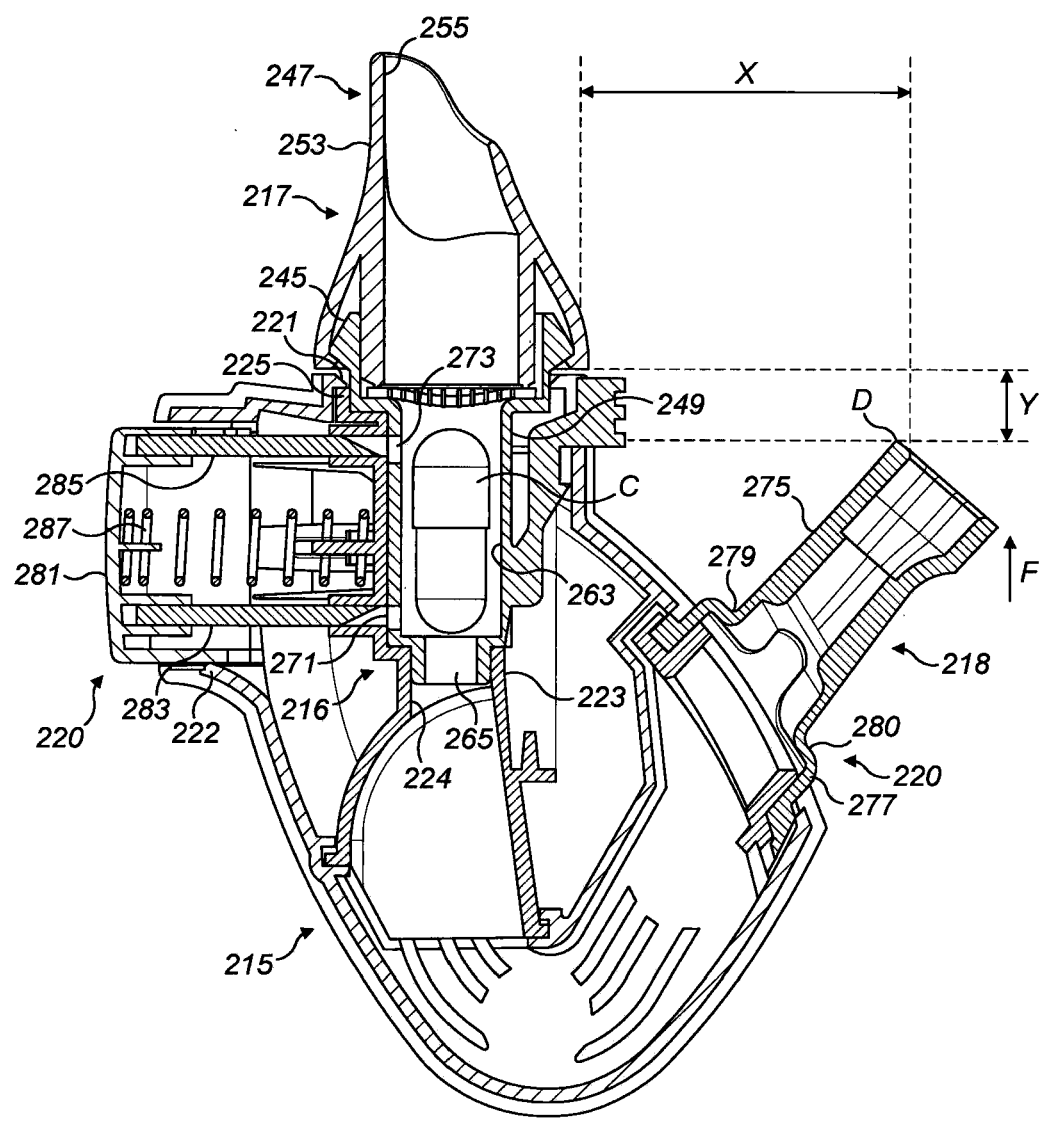
FIGS. 4(a) and (b) illustrate a Breath Powered™ Bi-Directional™ nasal delivery device in accordance with a further embodiment of the present disclosure.
Figure 7:
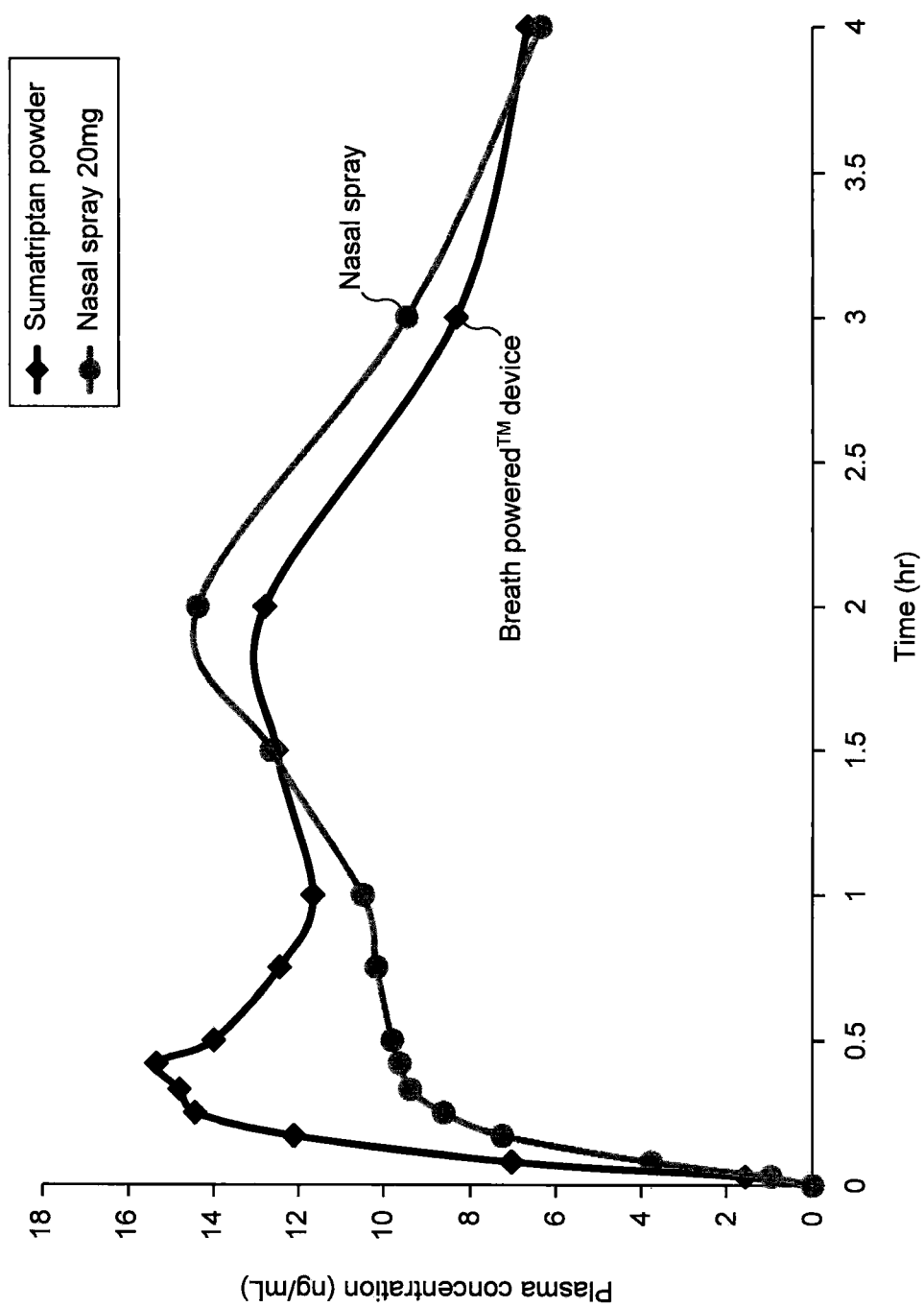
Figure 12:
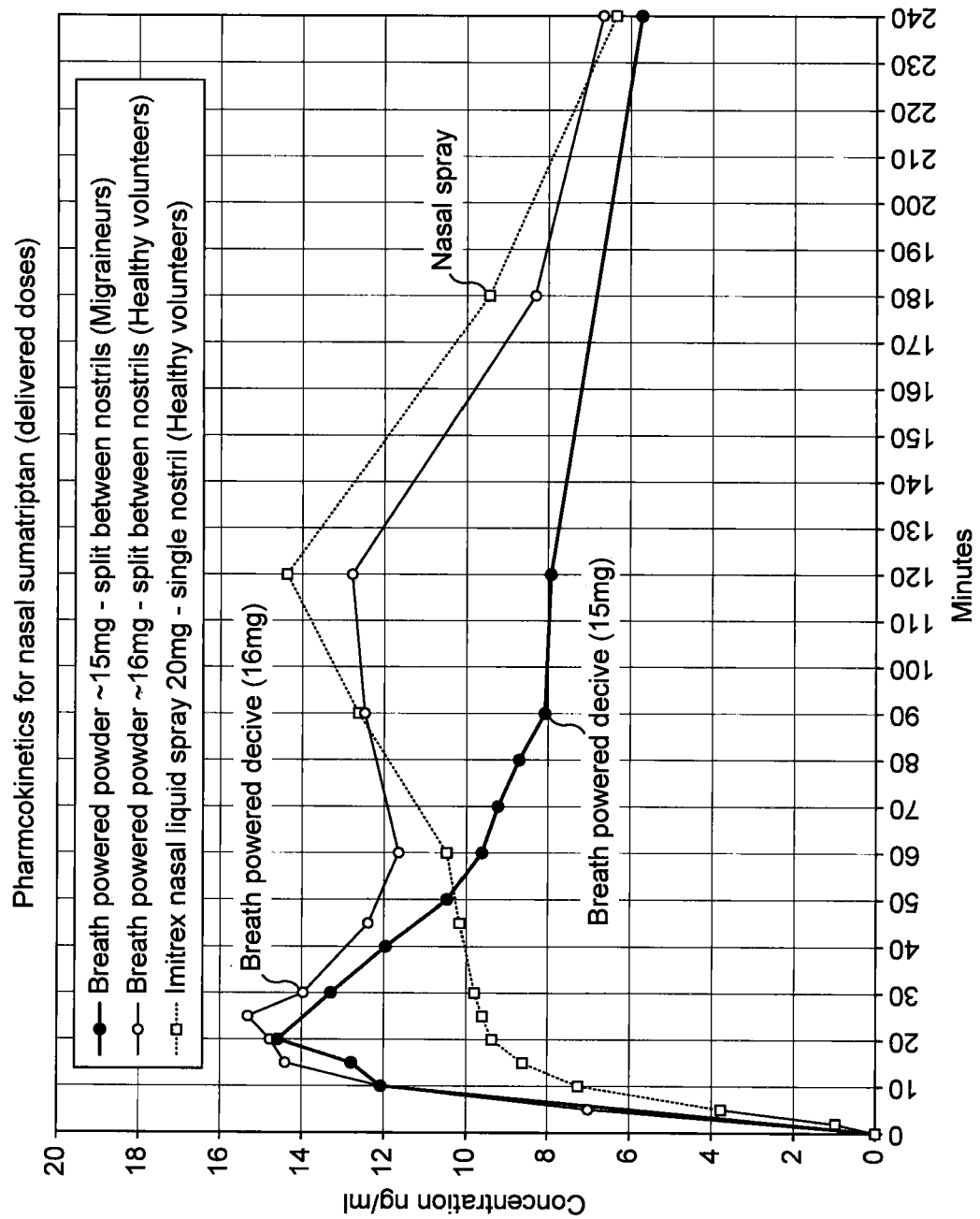
Figure 13:
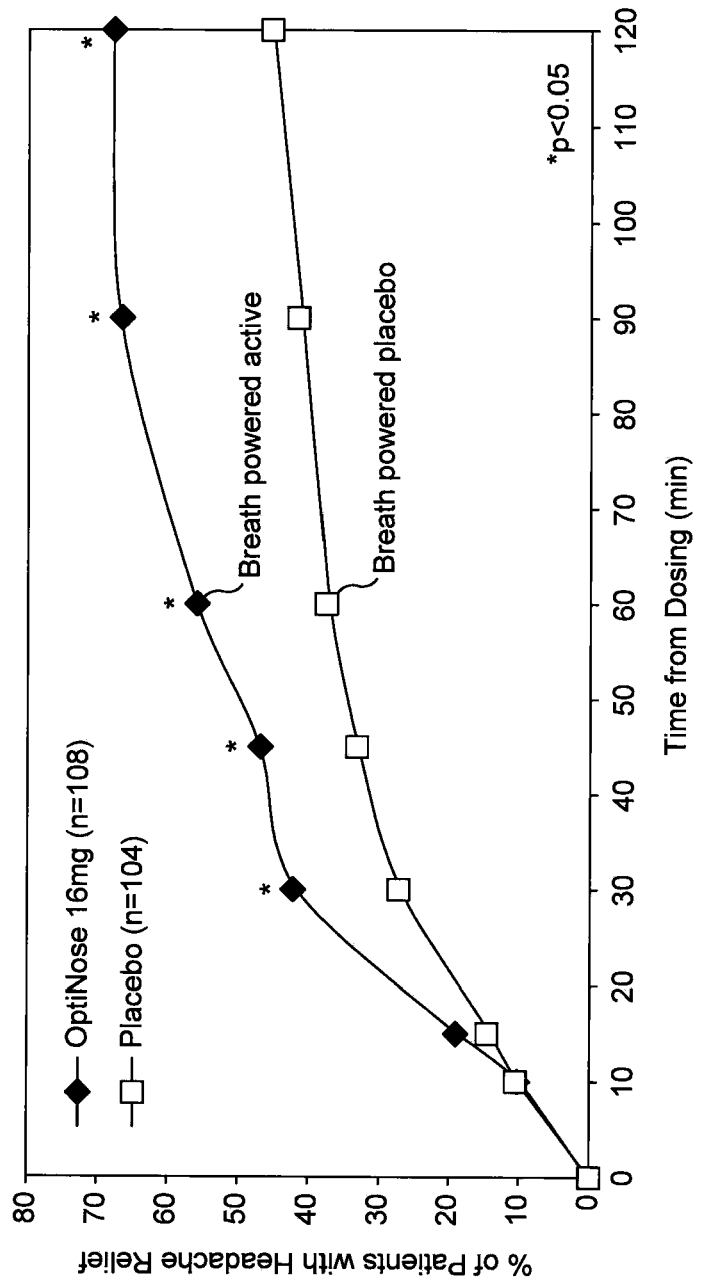
Figure 15:
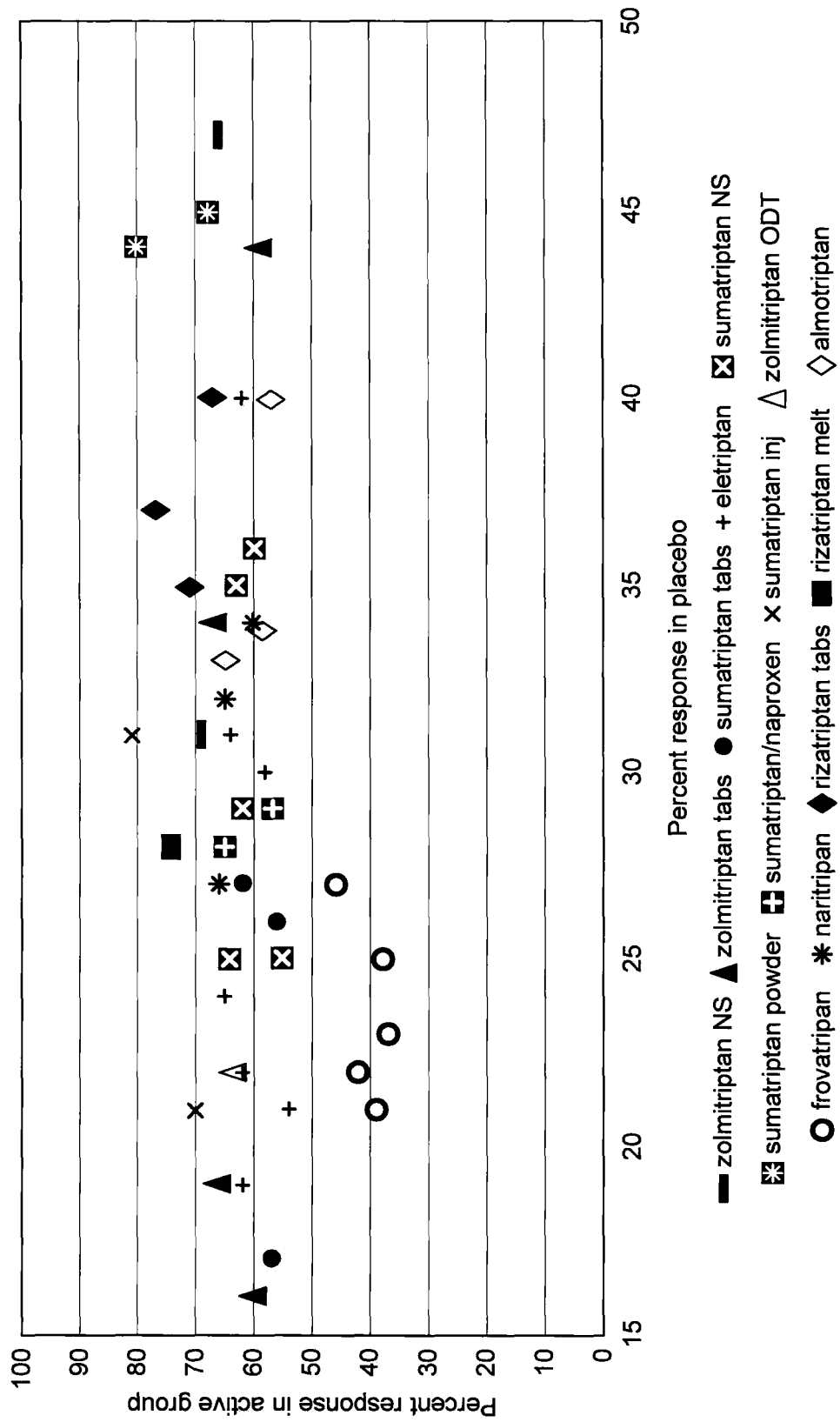
Figure 16:
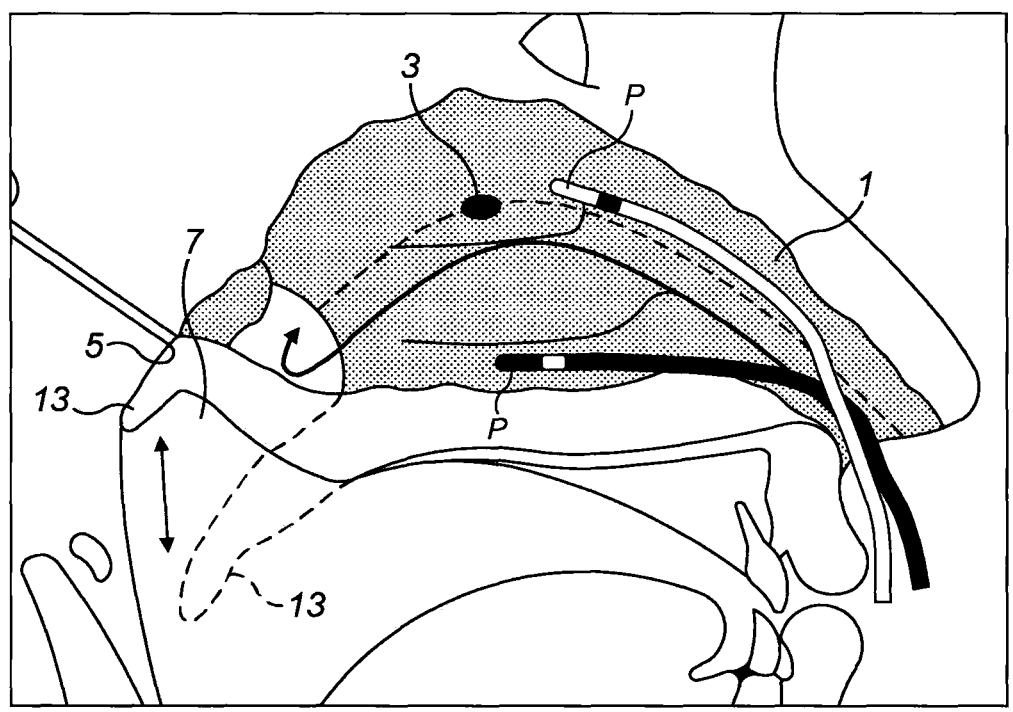
Figure 17:
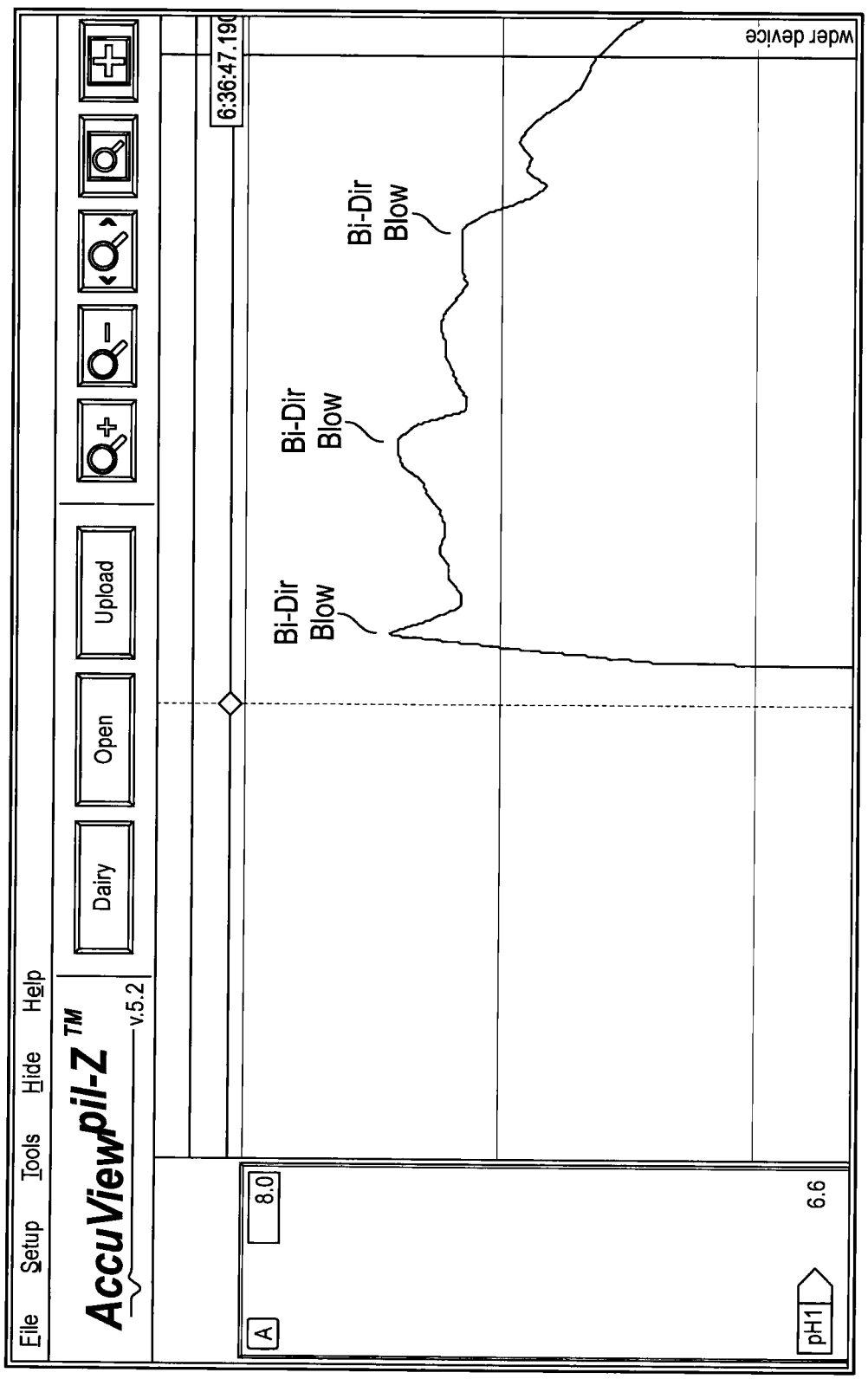
Figure 18:
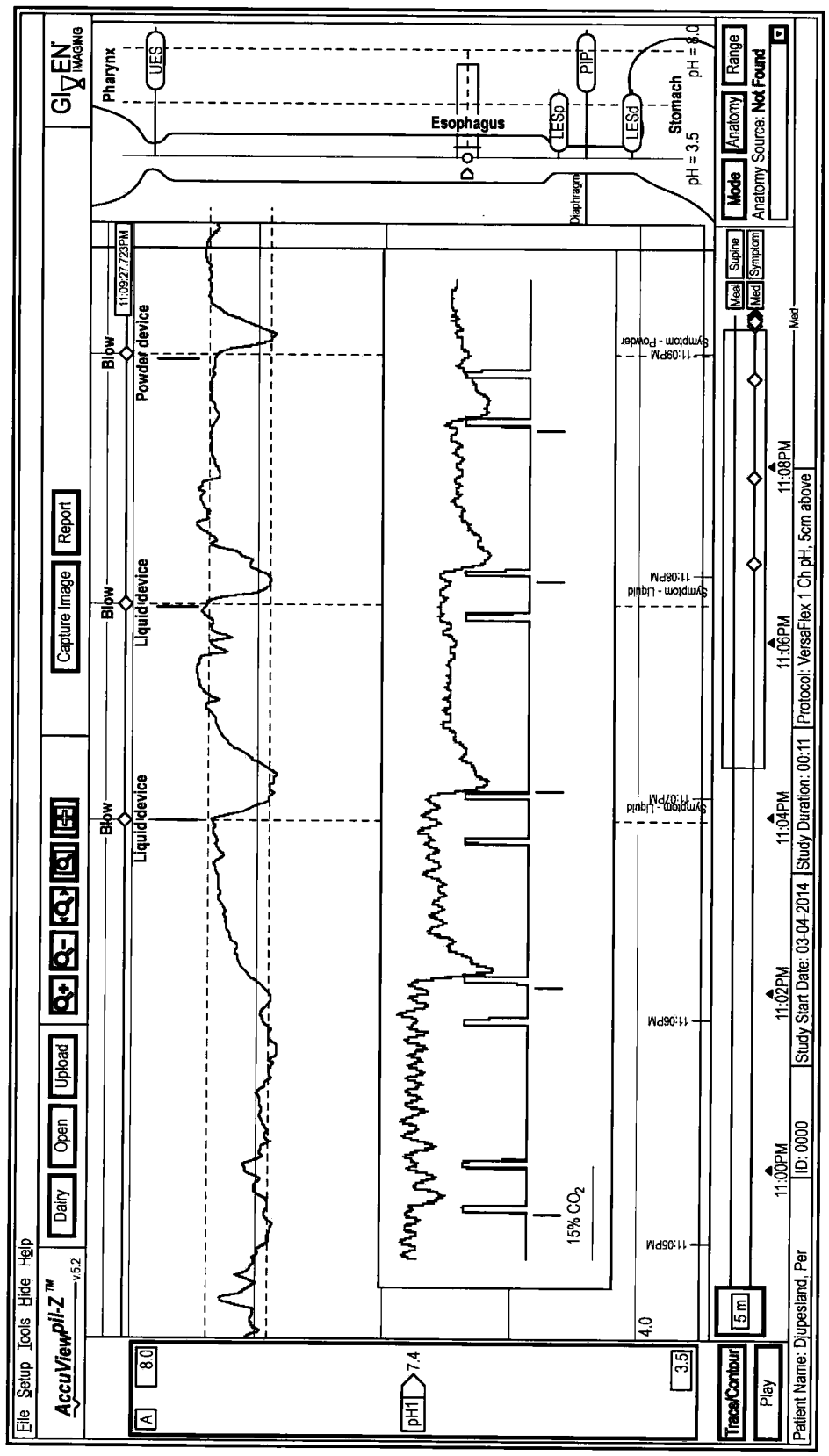
Figure 19:
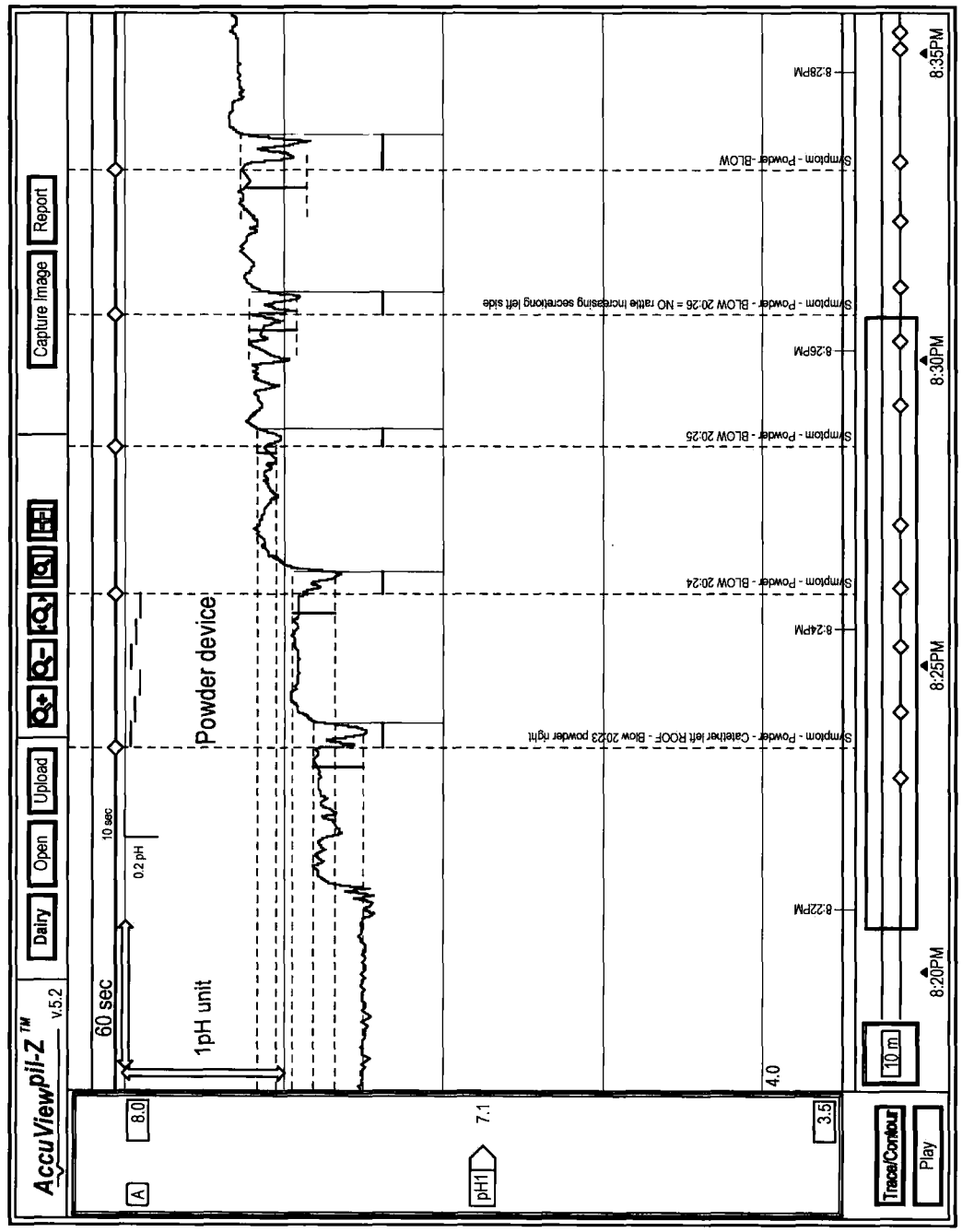
Figure 20:
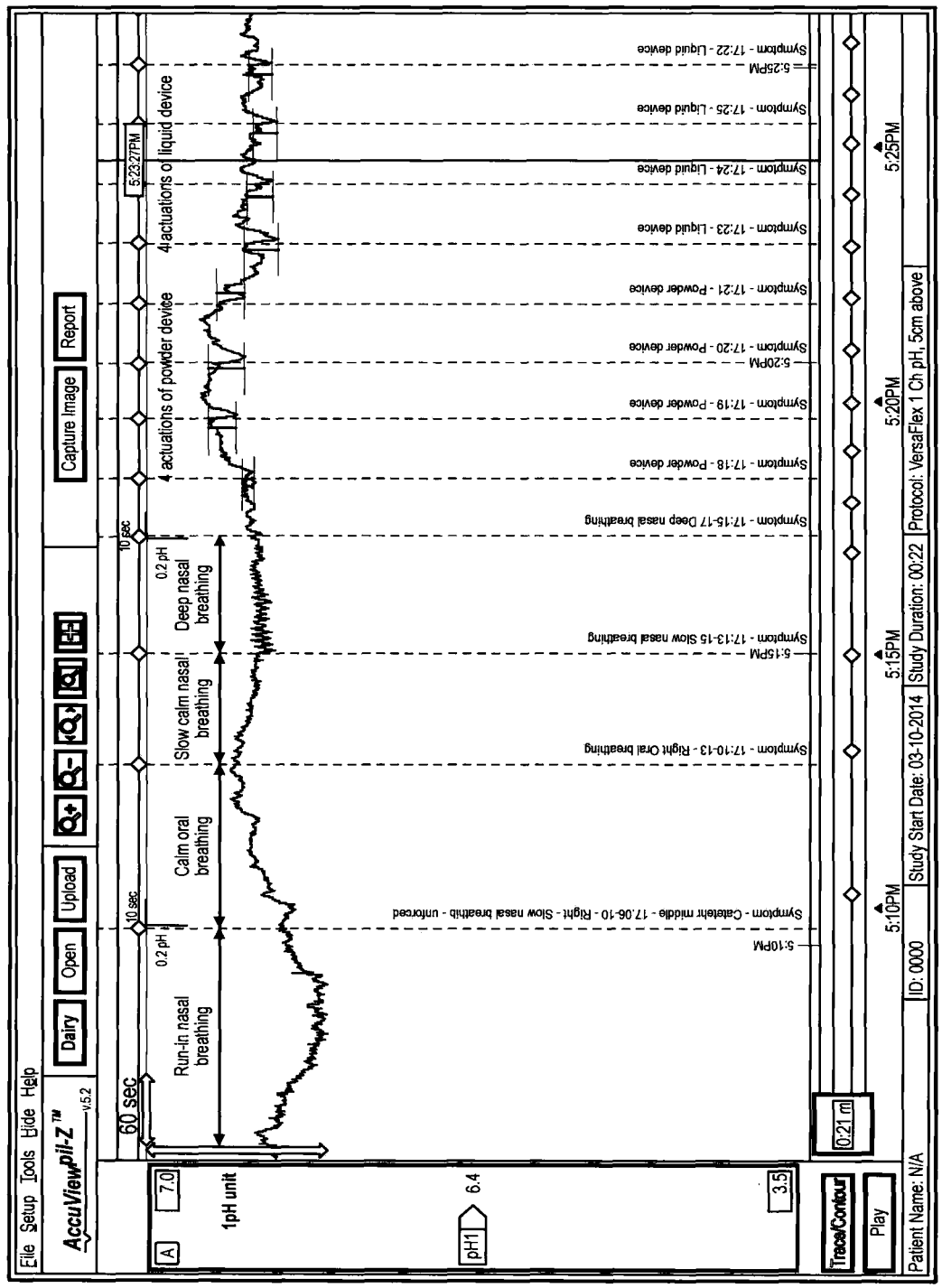
Figure 22:
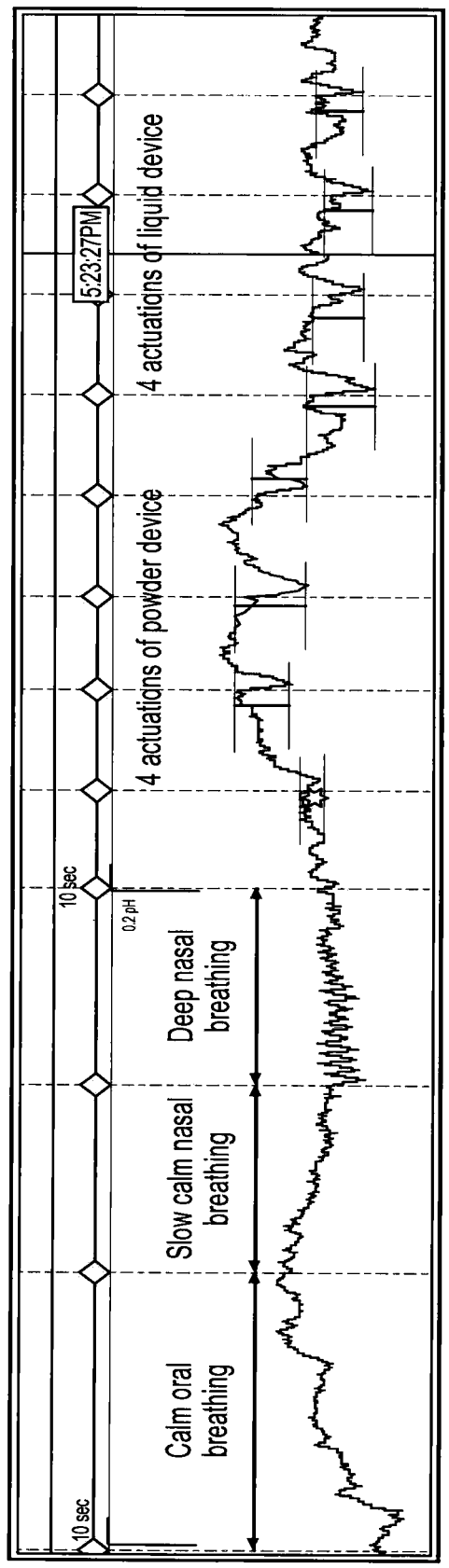
Figure 24:
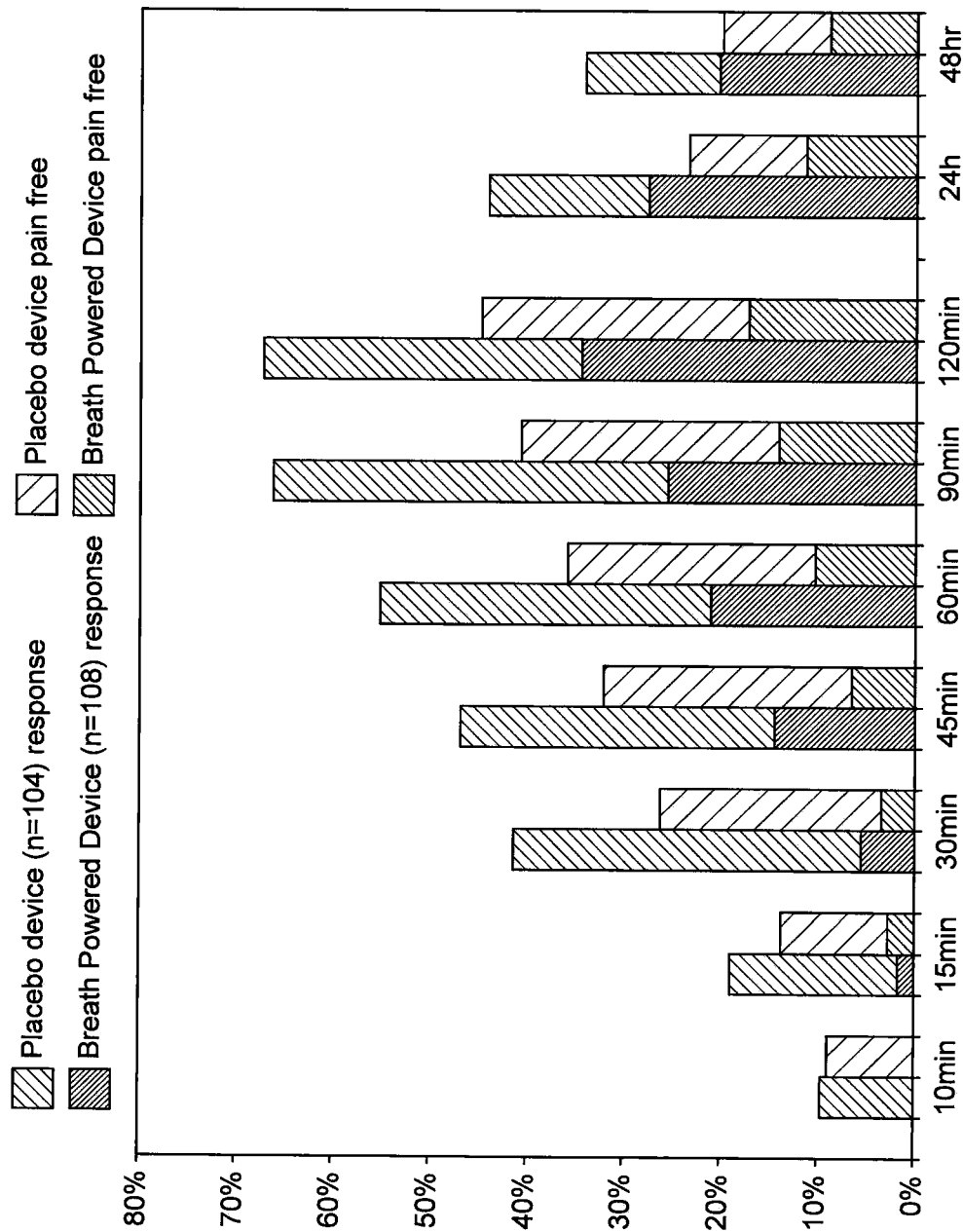
Figure 25:
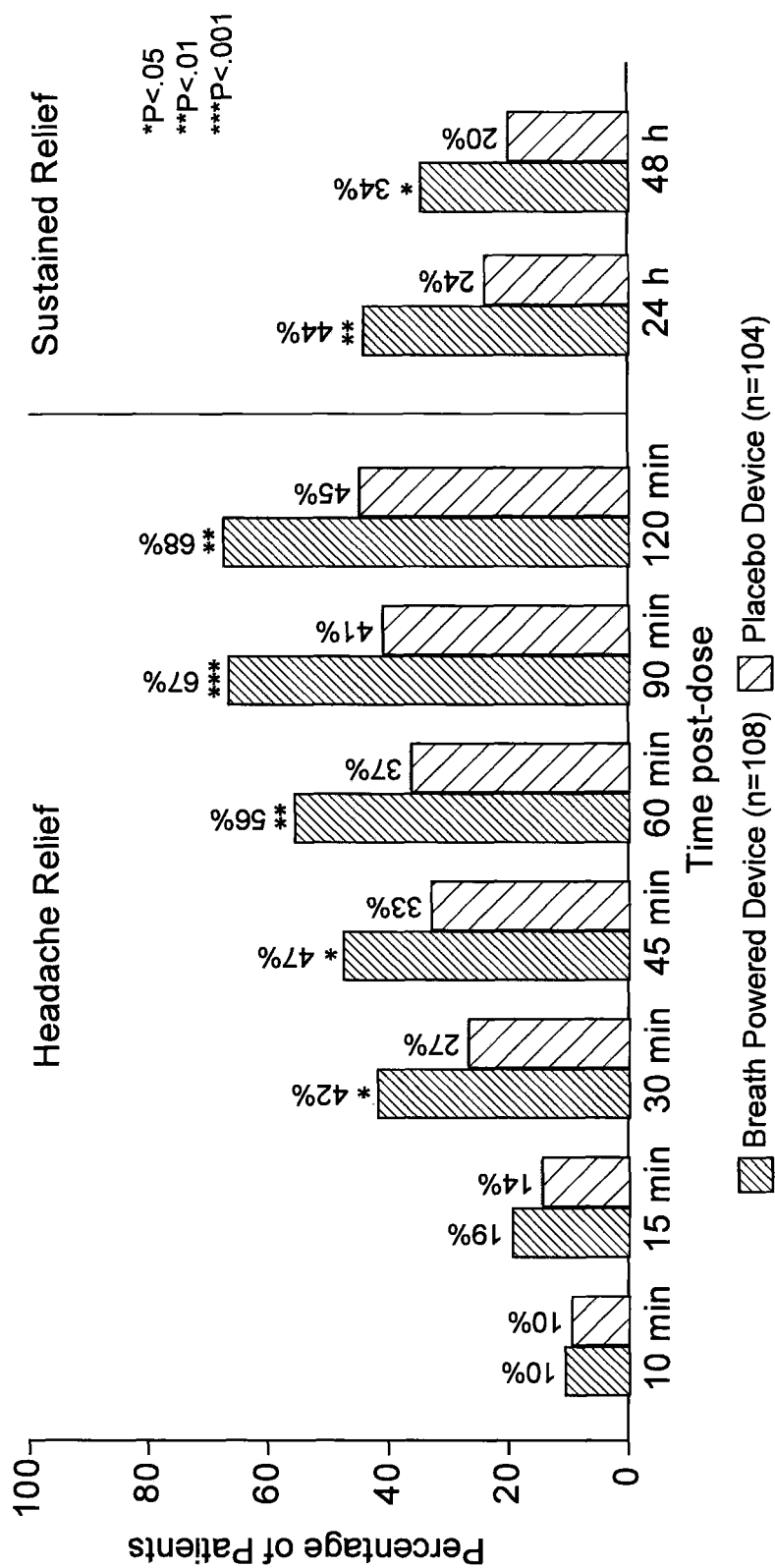
Figure 26:
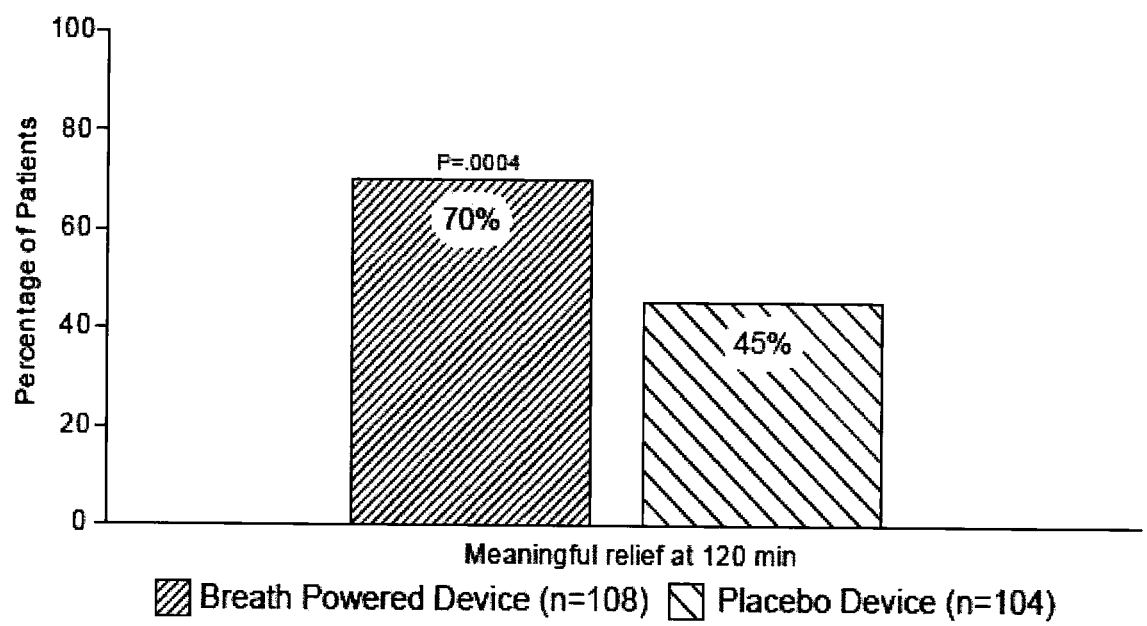
Figure 27:
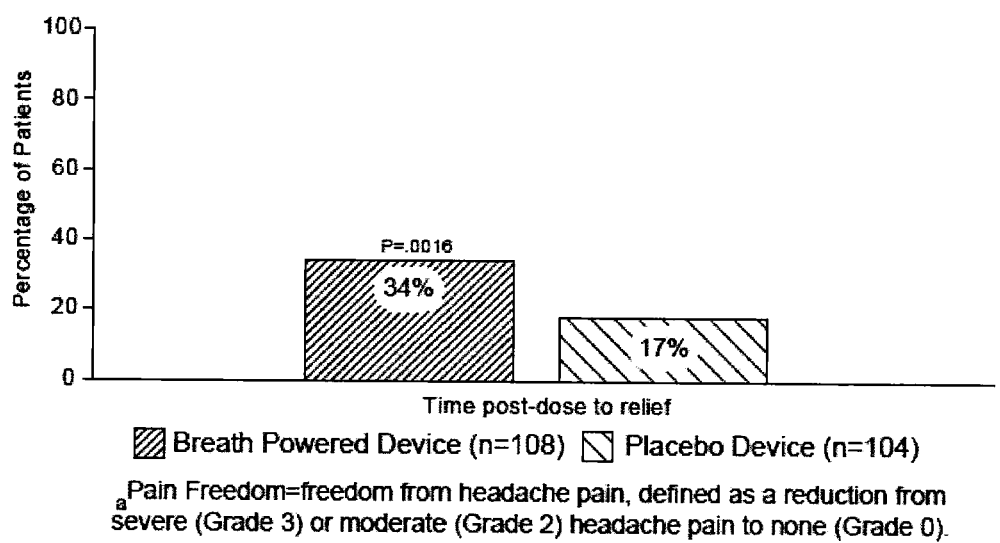
Figure 28:
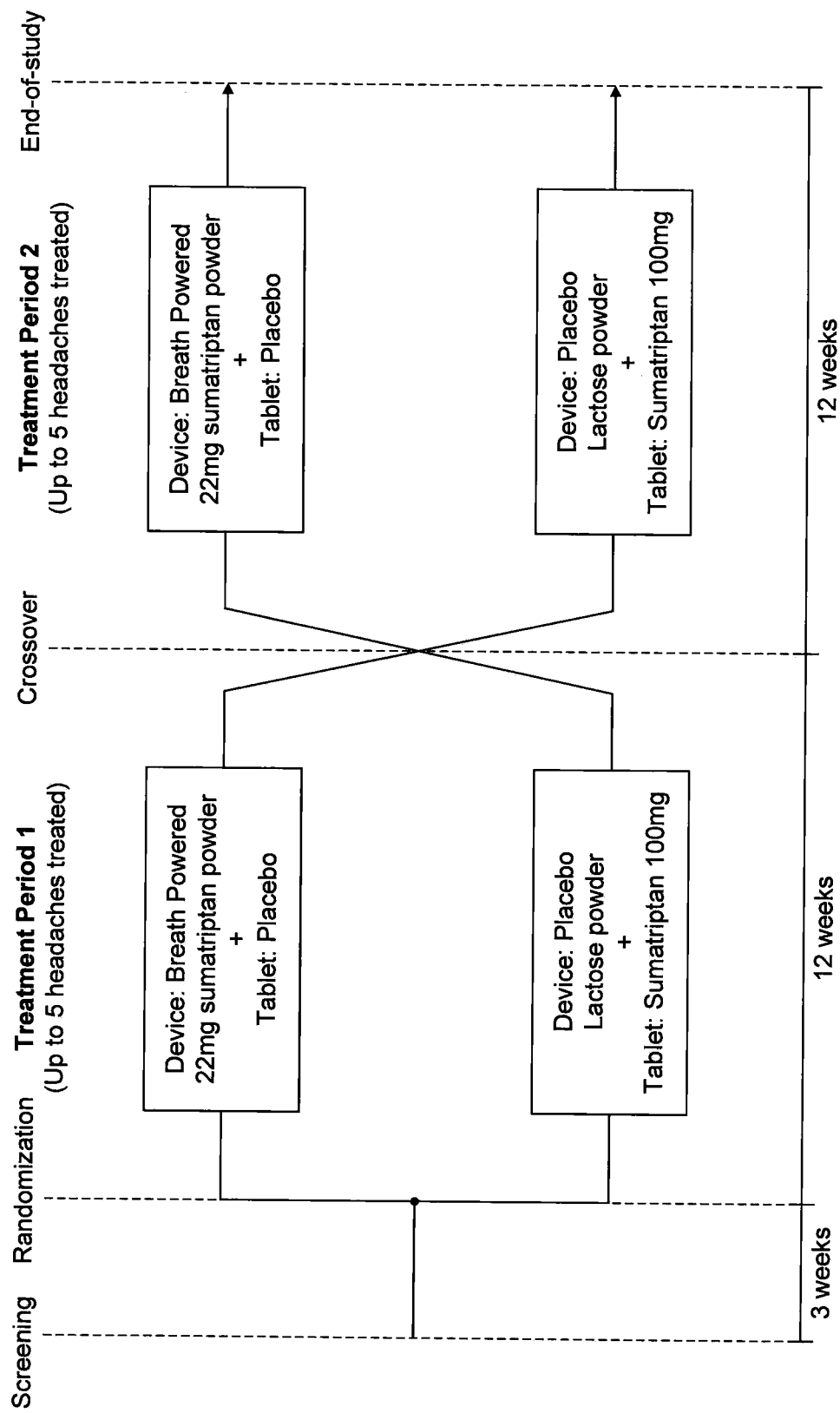
Figure 31:
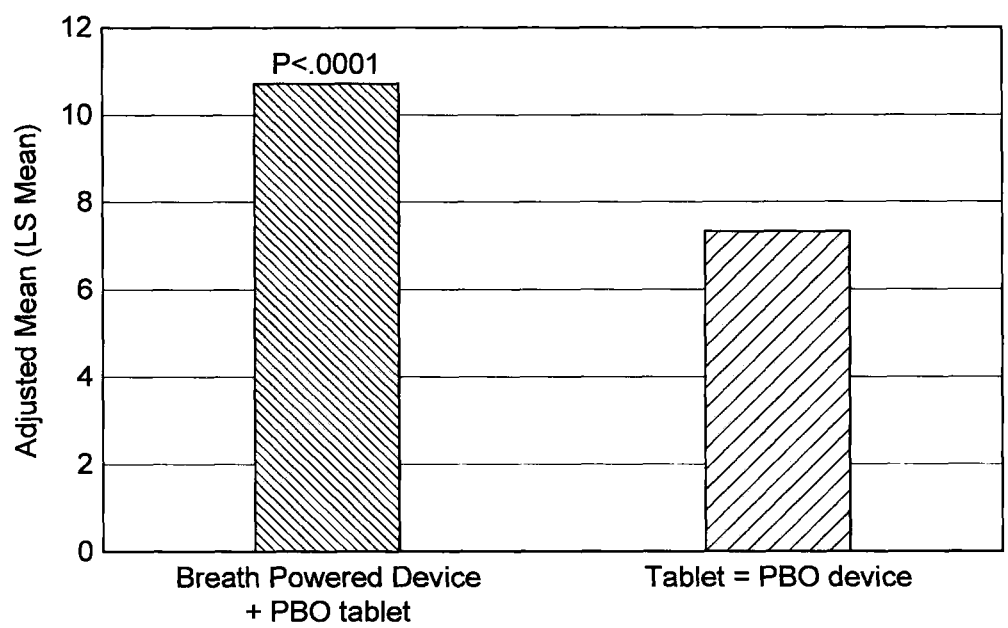
Figure 33:
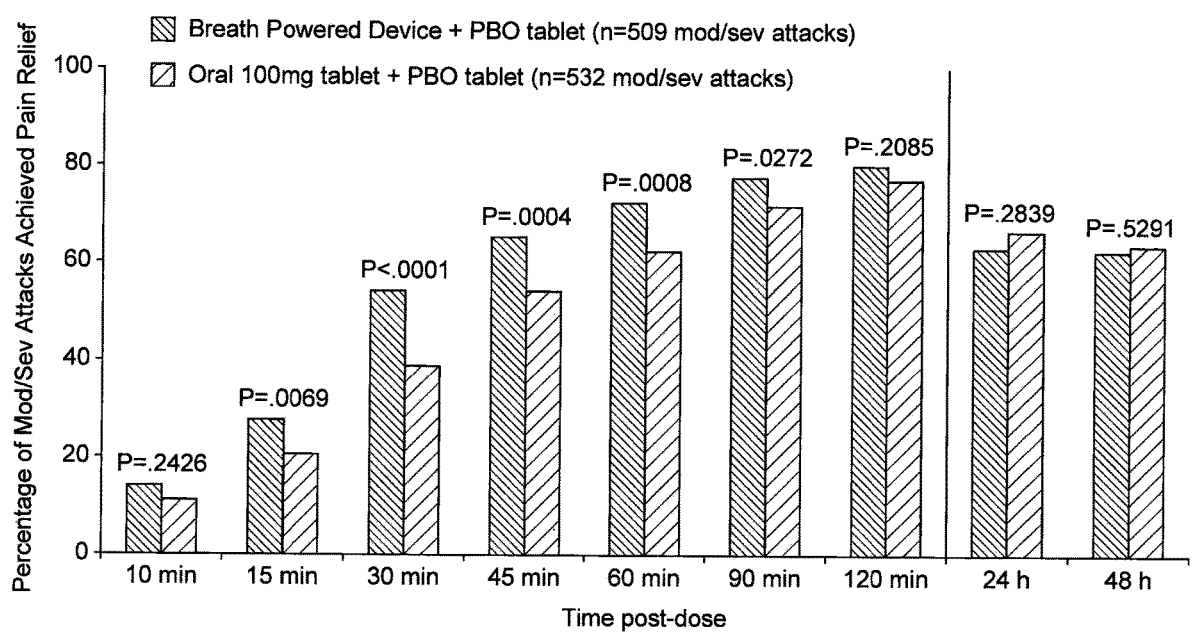
Figure 35:
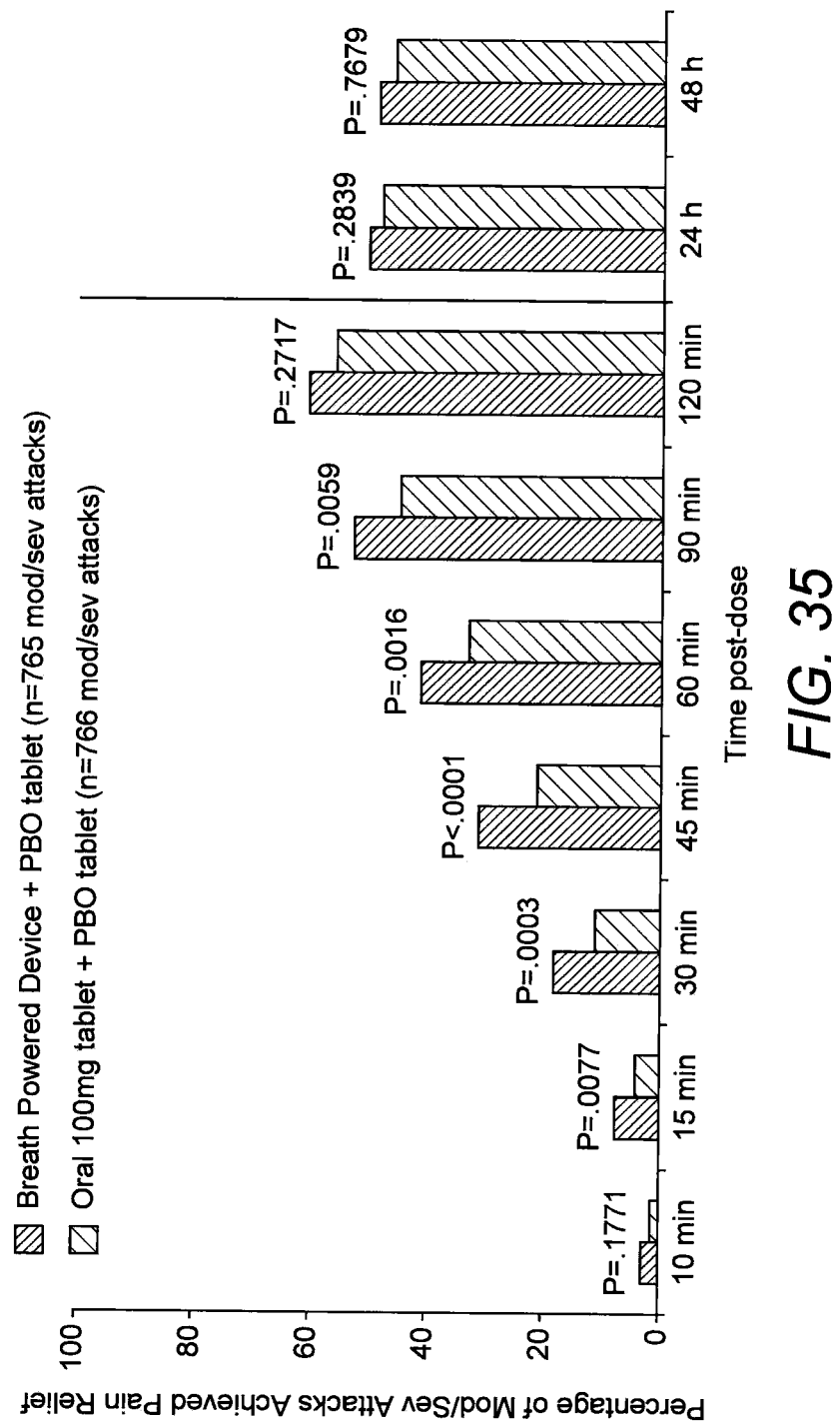

FIG. 7 illustrates sumatriptan plasma concentration-time profiles over the first 4 hrs after administration of sumatriptan powder using the Breath Powered™ device of FIGS. 2(a) and (b) as compared with the 20 mg nasal spray for the study of Example #2;

FIG. 8 illustrates sumatriptan pharmacokinetic results for intranasal delivery of sumatriptan powder using the Breath Powered™ device of FIGS. 2(a) and (b) as compared with 20 mg nasal spray, 100 mg tablet and 6 mg sub-cutaneous injection for the study of Example #2;

FIG. 9 illustrates statistical comparisons of plasma sumatriptan pharmacokinetic parameters for the study of Example #2;

FIG. 10 illustrates statistical comparisons of sumatriptan plasma pharmacokinetic parameters, including for nitroglycerin (GTN)-induced migraines and on healthy subjects, for the study of Example #3;

FIG. 11(a) shows initial regional nasal deposition (0-2 mins) using the Breath Powered™ device of FIGS. 2(a) and (b) and delivery with a traditional nasal spray pump in the study of Example #3;

FIG. 11(b) shows initial horizontal nasal distribution (0-2 mins) using the Breath Powered™ device of FIGS. 2(a) and (b) and delivery with a conventional nasal spray pump in the study of Example #3;

FIG. 12 shows pharmacokinetic (PK) profiles for nasal sumatriptan from two crossover studies using the Breath Powered™ device of FIGS. 2(a) and (b) and a conventional nasal spray (Imitrex® 6 mg Nasal Spray or approved or generic equivalent) in the study of Example #3, with one study being done in migraine patients during GTN challenge and the other study being performed in healthy volunteers;

FIG. 13 shows the proportion of patients with headache relief in the study of Example #6;

FIG. 14 shows two-hour pain relief as reported in package inserts;

FIG. 15 shows two-hour pain response rates reported in package inserts by study for active and placebo;

FIG. 16 shows positions of a pH probe located generally at upper and lower regions of a nasal passage in the study of Example #8;

FIG. 17 shows pH as a function of exhalation flow using the Breath Powered™ device of FIGS. 4(a) and (b) in the study of Example #8;

FIG. 18 shows pH as a function of exhalation flow using the Breath Powered™ devices of FIGS. 3(a) and (b) and FIGS. 4(a) and (b) in the study of Example #8;

FIG. 19 shows pH as a function of exhalation flow using the Breath Powered™ device of FIGS. 4(a) and (b) in the study of Example #8;

FIG. 20 shows pH as a function of exhalation flow using the Breath Powered™ device of FIGS. 4(a) and (b) in the study of Example #8;

FIG. 21 shows data for 3 s pulses of regular air (0%) and carbon dioxide at 15% and 45% delivered to the nose from a prior art reference (Shusterman, 2003);

FIG. 22 shows pH as a function of exhalation flow for oral breathing, calm nasal breathing and calm nasal breathing before delivery with the Breath Powered™ delivery devices of FIGS. 3(a) and (b) and FIGS. 4(a) and (b) in the study of Example #8;

FIG. 23 shows patient demographics and baseline characteristics (FAS) for the study of Example #9;

FIG. 24 shows pain response for delivery of sumatriptan using the Breath Powered™ device of FIGS. 4(a) and (b) as compared to placebo for in the study of Example #9;

FIG. 25 shows the proportion of patients with headache relief at specified time points up to 120 min post-dose and with sustained relief at 24 and 48 h (FAS) using the Breath Powered™ device of FIGS. 4(a) and (b) as compared to placebo in the study of Example #9;

FIG. 26 shows a proportion of patients with meaningful relief at 120 min post-dose (FAS) using the Breath Powered™ device of FIGS. 4(a) and (b) as compared to placebo in the study of Example #9;

FIG. 27 shows proportion of patients who achieved pain freedom at 120 min post-dose (FAS) using the Breath Powered™ device of FIGS. 4(a) and (b) as compared to placebo in the study of Example #9;

FIG. 28 represents the design of the study of Example #10;

FIG. 29 shows patient demographics and baseline characteristics in the safety assessment sample (SAS) for the study of Example #10;

FIGS. 30 and 31 show the primary endpoint for pain relief at 30 min post-dose (SPID-30) for the delivery of sumatriptan powder using the Breath Powered™ device of FIGS. 4(a) and (b) as compared to an oral sumatriptan tablet (Imitrex® 100 mg Tablet or approved or generic equivalent) in the study of Example #10;

FIGS. 32 and 33 show the proportion of patients with pain relief at specified time periods post-dose for the delivery of sumatriptan powder using the Breath Powered™ device of FIGS. 4(a) and (b) as compared to an oral sumatriptan tablet (Imitrex® 100 mg Tablet or approved or generic equivalent) in the study of Example #10;

FIGS. 34 and 35 show the proportion of patients with pain freedom at specified time periods post-dose for the delivery of sumatriptan powder using the Breath Powered™ device of FIGS. 4(a) and (b) as compared to an oral sumatriptan tablet (Imitrex® 100 mg Tablet or approved or generic equivalent) in the study of Example #10;

FIG. 36 shows the proportion of patients with pain reduction at specified time periods post-dose for the delivery of sumatriptan powder using the Breath Powered™ device of FIGS. 4(a) and (b) as compared to an oral sumatriptan tablet (Imitrex® 100 mg Tablet or approved or generic equivalent) in the study of Example #10;

FIG. 37 shows the proportion of patients who remained pain free at 24 and 48 hr post-dose for the delivery of sumatriptan powder using the Breath Powered™ device of FIGS. 4(a) and (b) as compared to an oral sumatriptan tablet (Imitrex® 100 mg Tablet or approved or generic equivalent) in the study of Example #10; and FIG. 38 shows the proportion of patients with atypical triptan sensations within 120 min post-dose for the delivery of sumatriptan powder using the Breath Powered™ device of FIGS. 4(a) and (b) as compared to an oral sumatriptan tablet (Imitrex® 100 mg Tablet or approved or generic equivalent) in the study of Example #10.

DESCRIPTION OF EMBODIMENTS

Reference will now be made in detail to the exemplary embodiments of the disclosure, examples of which are illustrated in the accompanying drawings. Wherever possible, the same reference numbers will be used throughout the drawings to refer to the same or like parts.

Exemplary Delivery Devices

Device #1

FIGS. 2(a) and (b) illustrate a first Breath Powered™ Bi-Directional™ powder delivery device which is operative to deliver a powder aerosol, according to one embodiment.

This delivery device comprises a housing 15, a capsule-receiving unit 16 for receiving a capsule C, a nosepiece unit 17 for fitting to a nasal cavity of a subject, a mouthpiece 18 through which the subject exhales, and a capsule-piercing mechanism 20, which is operable to pierce a capsule C as contained by the capsule-receiving unit 16 and thereby prime the delivery device for operation.

The housing 15 includes a first, nosepiece aperture 21, in this embodiment at the upper end of the housing 15, which receives the nosepiece unit 17, and a second, lateral aperture 22, in this embodiment in an end wall of the housing 15, through which extends an actuator button 81 of the capsule-piercing mechanism 20, as will be described in more detail hereinbelow.

The capsule-receiving unit 16 comprises a capsule-receiving member 23, in this embodiment an elongate, upstanding chamber which is disposed opposite the nosepiece aperture 21 in the housing 15, for receiving a capsule C, in this embodiment as contained within a capsule-containing member 49 of the nosepiece unit 17, as will be described in more detail hereinbelow.

In this embodiment the capsule-receiving member 23 includes an inlet 24 and an outlet 25 for providing for an air flow therethrough, with the outlet 25, as defined by an upper, downstream end of the capsule-receiving member 23, being adapted to receive the capsule-containing member 49 of the nosepiece unit 17, such that the capsule-containing member 49 is a sealing fit within the capsule-receiving member 23.

The nosepiece unit 17 comprises a main body member 45 which is configured to fit in the nosepiece aperture 21 of the housing 15, a nosepiece 47 which extends outwardly of the main body member 45 for fitting to the nostril of the subject, and a capsule-containing member 49 which extends inwardly of the main body member 45 and contains a capsule C, the contents of which are to be delivered to the nasal cavity of the subject. In one embodiment the capsule C is a hydroxypropyl methylcellulose (HPMC) capsule which contains a particulate substance, such as a powdered substance, and typically a pharmaceutical substance. In other embodiments the capsule C could be formed substantially of another cellulose derivative, such as hydroxypropylcellulose, methylcellulose, ethylcellulose and carboxymethylcellulose. In an alternative embodiment the capsule C can be formed from a gelatin derivative. In one embodiment the capsule C can be coated with a hydrophobic material, such as parylene.

In this embodiment the nosepiece 47 has a substantially frusto-conical outer section 53 for guiding the nosepiece unit 17 into a nasal passage of the subject and providing a fluid-tight seal with the nares of the nostril, and includes an inner channel 55, here of substantially cylindrical section, through which substance is delivered to a posterior region of the nasal passage of the subject, in this embodiment an upper posterior region as bounded by a vertical plane which is located posterior of the anterior nasal spine AnS at a position corresponding to one-quarter of the distance between the anterior and posterior nasal spines AnS, PnS and a horizontal plane which is located above the nasal floor at a height one-third of the distance between the nasal floor and the cribiform plate. As discussed hereinabove, the present inventors have recognized that an increased delivery of powdered substance to the upper posterior region of the nasal passage surprisingly provides for a very rapid onset of action as compared to the conventional nasal administration of substances, for example, a conventional liquid nasal spray.

In this embodiment the nosepiece 47 is configured to deliver a significant fraction of substance to the upper posterior region of the nasal passage, here an initial deposition of greater than 30% of the delivered dose.

In this embodiment the nosepiece 47, in providing a fluid-tight seal with the nostril of the subject, provides for bi-directional delivery through the nasal airway of the subject, as disclosed in the applicant's earlier WO-A-2000/051672, which is incorporated by reference in its entirety. In another embodiment, however, the nosepiece 47 need not provide a sealing fit, thus encompassing delivery to the nasal cavity, but not necessarily bi-directional delivery.

In this embodiment the nosepiece 47 includes a trap element 57, typically a perforated or mesh element, for preventing any foreign matter, such as a part of the capsule C, which is above a predetermined size from passing through the nosepiece 47 and into the nasal cavity of the subject.

The capsule-containing member 49 includes an elongate flow passage 63, in this embodiment cylindrical in shape, in which the capsule C is oriented axially therealong such as to be rotatable therewithin when an air flow is delivered therethrough, and an inlet aperture 65 in fluid communication with one, the downstream, end of the flow passage 63, which inlet aperture 65 provides a flow restriction to an air flow as delivered therethrough and acts as a seat for one, the lower, end of the capsule C prior to the delivery of an air flow through the flow passage 63.

The capsule-containing member 49 further includes a plurality of, in this embodiment first and second piercing apertures 71, 73 in a lateral wall thereof for enabling the capsule C to be pierced at locations spaced along the axial length thereof. In one embodiment the first, lower aperture 71 could be located such that the capsule C is pierced at a location above the height of the dose of substance as contained thereby when the lower end of the capsule C is seated in the inlet aperture 65 of the flow passage 63. In this way, the dose of substance as contained by the capsule C is not released into the flow passage 63 until an air flow is delivered through the flow passage 63.

In this embodiment the nosepiece unit 17 is provided as a replaceable unit which is replaced following each operation of the delivery device. In this embodiment the nosepiece unit 17 can be packaged in air-tight packaging, for example, an aluminum foil package.

The mouthpiece unit 18 comprises a mouthpiece 77, in this embodiment as gripped in the lips of the subject, through which the subject exhales to deliver an entraining air flow through the capsule-receiving unit 16, and an air chamber 78, in this embodiment an elongate tubular section, which fluidly connects the mouthpiece 77 and the capsule-receiving unit 16.

In this embodiment the air chamber 78 has a greater volume than the capsule-receiving member 23 of the capsule-receiving unit 16, and in one embodiment has a volume at least twice that of the capsule-receiving member 23.

In one embodiment the air chamber 78 incorporates a temperature regulator 79, here formed as a condenser for cooling the exhaled air flow, at least at the upstream end thereof. With this configuration, the exhaled air flow is cooled during exhalation.

In this embodiment the temperature regulator 79 comprises a labyrinthine structure. In another embodiment the temperature regulator 79 could be provided by a filter element, which could also act as a microbiological filter.

In one embodiment the temperature regulator 79 could include means for drying the condensate as collected therein when the delivery device is not in use.

In one embodiment the air chamber 78 is removable, such as to allow for cleaning or replacement.

This arrangement has been found to provide for reliable operation of the delivery device, in delivering substance from the capsule C. The present inventors have established that the provision of moist exhaled air directly to the capsule C can sometimes prevent the required rotation of the capsule C, and thereby prevent proper release of the substance as contained thereby. By providing a volume of cooler air, and arranging for that volume of cooler air to be delivered initially in a burst, the required rotation of the capsule C is seen repeatedly.

The capsule-piercing mechanism 20 comprises an actuator button 81 which extends through the lateral aperture 22 in the housing 15 such as to allow for operation by the subject, a plurality of, in this embodiment first and second piercing elements 83, 85 which are supported by the actuator button 81 and extend forwardly thereof, such that, on depression of the actuator button 81 from a retracted position to an extended position, the piercing elements 83, 85 are driven through respective ones of the piercing apertures 71, 73 in the lateral wall of the capsule-containing member 49 to pierce the capsule C.

In this embodiment the capsule-piercing mechanism 20 includes a resilient element 87 which acts to bias the actuator button 81 outwardly towards the retracted position, such that, following depression of the actuator button 81 to pierce the capsule C, the actuator button 81 is returned to the retracted position. In this embodiment the resilient element 87 is formed as an integral part of the actuator button 81, but in other embodiments could be provided by a separate element, such as a compression spring.

Exemplary operation of this delivery device will now be described hereinbelow.

Firstly, taking the delivery device in hand, and with a nosepiece unit 17 inserted in the housing 15, the subject depresses the actuator button 81 of the capsule-piercing mechanism 20 such as to pierce the capsule C as contained in the capsule-containing member 49.

By depressing the actuator button 81, the capsule C is pierced by the piercing elements 83, 85 at two locations spaced along the axial length thereof.

The actuator button 81 is then released, which causes the actuator button 81 to be returned to the retracted position under the bias of the biasing element 87. In this way, the delivery device is primed and ready for use.

The subject then inserts the nosepiece 47 into one of his/her nasal passages until the nosepiece 47 abuts the nares of the nostril such as to establish a fluid-tight seal therewith, at which point the distal end of the nosepiece 47 extends about 2 cm into the nasal passage of the subject, and grips the mouthpiece 77 in his or her lips.

The subject then begins to exhale through the mouthpiece 77, which exhalation acts to close the oropharyngeal velum of the subject and drive an air flow through the nasal airway of the subject, with the air flow passing into the one nasal passage, around the posterior margin of the nasal septum and out of the other nasal passage, thereby achieving a bi-directional air flow through the nasal airway of the subject.

When the subject exhales with sufficient force, the capsule C is lifted from the seat as defined by the inlet aperture 65 of the capsule-containing member 49 and the capsule C is rotated, which rotation acts to release the substance from within the capsule C which is entrained by the exhaled air flow and delivered to the posterior region of the nasal cavity of the subject. With continued exhalation, the capsule C continues to rotate.

Further, in this device, the capsule C is configured to vibrate, and through the sound transmission path as provided by the nosepiece unit 17 being inserted into the nostril, this vibration acts to promote ventilation of the nasal airway, particularly in the posterior region of the nasal cavity. It is postulated that this vibration contributes to efficacy, as outlined in the studies described below.

This operation of the delivery device is then repeated with a new capsule C, with the device being fitted to the other, second nostril. In this embodiment the entire nosepiece unit 17 is replaced, but in other embodiments either the capsule-containing member 49 or just the capsule C could be replaced.

The gas may be delivered at a pressure of 2, 3, 4, 5, 6, 7, 8, 9 or 10 kPa.

Device #2

FIGS. 3(*a*) and (*b*) illustrate a Breath Powered™ Bi-Directional™ liquid delivery device which can operate to deliver a liquid aerosol.

The delivery device comprises a housing 115, a nosepiece 117 for fitting in a nasal cavity of a subject, a mouthpiece 118 into which the subject in use exhales, such as to enable delivery of an air flow into and through the nasal airway of the subject on exhalation by the subject through the mouthpiece 118, and a substance supply unit 120, which is manually actuatable to deliver substance to the nasal cavity of the subject.

The housing 115 comprises a body member 121, in this embodiment of substantially elongate, tubular section, which includes an aperture 123 at one end thereof, through which projects an actuating part of the substance supply unit 120, in this embodiment as defined by the base of a substance-containing chamber 151.

The housing 115 further comprises a valve assembly 125 which is fluidly connected to the nosepiece 117 and the mouthpiece 118, and operable between closed and open configurations, as illustrated in FIGS. 3(a) and (b), such as to provide for an air flow, in this embodiment in the form of a burst of air, through the nosepiece 117 simultaneously with actuation of the substance supply unit 120, as will be described in more detail hereinbelow.

The valve assembly 125 comprises a main, body element 127 and a valve element 129 which is slideably disposed to the body element 127 between closed and open positions, as illustrated in FIGS. 3(a) and (b).

The body element 127 comprises a valve section 131, in this embodiment a tubular section, in which the valve element 129 is slideably disposed, and an inwardly flaring forward section 133, in this embodiment having an inwardly tapering section, which is downstream of the valve section 131 and fluidly connected to the nosepiece 117.

The valve section 131 of the body element 127 and the valve element 129 each include a valve aperture 137, 139, which are fluidly isolated when the valve element 129 is in the closed position, and in fluid communication when the valve element 129 is in the open position.

The nosepiece 117 comprises a body member 141 which defines an outer sealing surface 143 for providing a sealing fit between the nosepiece 117 and a nasal cavity of the subject, and an inner delivery channel 145, which is in selective fluid communication with the mouthpiece 119 such that an air flow is selectively delivered into and through the nasal airway of the subject on exhalation by the subject through the mouthpiece 119, and an outlet unit 147 for delivering substance into the nasal airway of the subject, which is disposed within the delivery channel 145.

In this embodiment the outlet unit 147 comprises a nozzle 149 for delivering substance to the nasal airway of the subject. In this embodiment the nozzle 149 is disposed in the delivery channel 145 co-axially with the same.

In one embodiment the distal end of the outlet unit 147 can be configured to extend at least about 2 cm, at least about 3 cm, or from about 2 cm to about 3 cm, into the nasal cavity of the subject.

In this embodiment the substance supply unit 120 is a pump unit, which comprises a substance-containing chamber 151 which contains substance and extends from the aperture 123 in the housing 115 as the actuating part of the substance supply unit 120, and a mechanical delivery pump 153 which is actuatable, here by depression of the substance-containing chamber 151, typically by a finger or thumb of the subject, to deliver a metered dose of substance from the substance-containing chamber 151 to the outlet unit 147 and from the nozzle outlet 149 thereof, here as an aerosol spray.

In this embodiment the substance-containing chamber 151 is coupled to the valve element 129 of the valve assembly 125, such as to be moved therewith and simultaneously provide for actuation of the substance supply unit 120 and opening of the valve assembly 125, whereby substance, here in the form of a spray, and an air flow, here as a burst of air, are simultaneously delivered to the nasal cavity of the subject.

In this embodiment the mechanical delivery pump 153 is a liquid delivery pump for delivering a metered dose of substance, but in an alternative embodiment the mechanical delivery pump 153 could be a powder delivery pump, which delivers metered doses of a powdered substance on actuation thereof.

In this embodiment the substance supply unit 120 is a multi-dose unit for delivering a plurality of metered doses of substance in successive delivery operations.

Device #3

FIGS. 4(a) and (b) illustrate a second Breath Powered™ Bi-Directional™ powder delivery device which is operative to deliver a powder aerosol, according to another embodiment.

This delivery device comprises a housing 215, a capsule-receiving unit 216 for receiving a capsule C, a nosepiece unit 217 for fitting to a nasal cavity of a subject, a mouthpiece 218 through which the subject exhales, a flexible coupling 219 which couples the mouthpiece 218 to the housing 215, and a capsule-piercing mechanism 220, which is operable to pierce a capsule C as contained by the capsule-receiving unit 216 and thereby prime the delivery device for operation.

The housing 215 includes a first, nosepiece aperture 221, in this embodiment at the upper end of the housing 215, which receives the nosepiece unit 217, and a second, lateral aperture 222, in this embodiment in an end wall of the housing 215, through which extends an actuator button 281 of the capsule-piercing mechanism 220, as will be described in more detail herein.

The capsule-receiving unit 216 comprises a capsule-receiving member 223, in this embodiment an elongate, upstanding chamber which is disposed opposite the nosepiece aperture 221 in the housing 215, for receiving a capsule C, in this embodiment as contained within a capsule-containing member 249 of the nosepiece unit 217, as will be described in more detail herein.

In this embodiment the capsule-receiving member 223 includes an inlet 224 and an outlet 225 for providing for an air flow therethrough, with the outlet 225, as defined by an upper, downstream end of the capsule-receiving member 223, being adapted to receive the capsule-containing member 249 of the nosepiece unit 217, such that the capsule-containing member 249 is a sealing fit within the capsule-receiving member 223.

The nosepiece unit 217 comprises a main body member 245 which is configured to fit in the nosepiece aperture 221 of the housing 215, a nosepiece 247 which extends outwardly of the main body member 245 for fitting to the nostril of the subject, and a capsule-containing member 249 which extends inwardly of the main body member 245 and contains a capsule C, the contents of which are to be delivered to the nasal cavity of the subject. In this embodiment the capsule C is formed from gelatin. In one embodiment the capsule C can be coated with a hydrophobic material, such as parylene.

In this embodiment the nosepiece 247 has a substantially frusto-conical outer section 253 for guiding the nosepiece unit 217 into a nasal passage of the subject and providing a fluid-tight seal with the nares of the nostril, and includes an inner channel 255, here of substantially cylindrical section, through which substance is delivered to a posterior region of the nasal passage of the subject, in this embodiment an upper posterior region as bounded by a vertical plane which is located posterior of the anterior nasal spine AnS at a position corresponding to one-quarter of the distance between the anterior and posterior nasal spines AnS, PnS and a horizontal plane which is located above the nasal floor at a height one-third of the distance between the nasal floor and the cribiform plate. As discussed hereinabove, the present inventors have recognized that an increased delivery of powdered substance to the upper posterior region of the nasal passage surprisingly provides for a very rapid onset of action as compared to the conventional nasal administration of substances, for example, a conventional liquid nasal spray.

In this embodiment the nosepiece 247 is configured to deliver a significant fraction of substance to the upper posterior region of the nasal passage, here an initial deposition of greater than 30% of the delivered dose.

In this embodiment the nosepiece 247, in providing a fluid-tight seal with the nostril of the subject, provides for bi-directional delivery through the nasal airway of the subject, as disclosed in the applicant's earlier WO-A-2000/051672, which is incorporated by reference in its entirety. In another embodiment, however, the nosepiece 247 need not provide a sealing fit, thus encompassing delivery to the nasal cavity, but not necessarily bi-directional delivery.

The capsule-containing member 249 includes an elongate flow passage 263, in this embodiment cylindrical in shape, in which the capsule C is oriented axially therealong such as to be rotatable therewithin when an air flow is delivered therethrough, and an inlet aperture 265 in fluid communication with one, the downstream, end of the flow passage 263, which inlet aperture 265 provides a flow restriction to an air flow as delivered therethrough and acts as a seat for one, the lower, end of the capsule C prior to the delivery of an air flow through the flow passage 263.

The capsule-containing member 249 further includes a plurality of, in this embodiment first and second piercing apertures 271, 273 in a lateral wall thereof for enabling the capsule C to be pierced at locations spaced along the axial length thereof.

In this embodiment the nosepiece unit 217 is provided as a replaceable unit which is replaced following each operation of the delivery device. In this embodiment the nosepiece unit 217 can be packaged in air-tight packaging, for example, an aluminum foil package.

The mouthpiece 218, in this embodiment as gripped in the lips of the subject and through which the subject exhales to deliver an entraining air flow through the capsule-receiving unit 216, comprises a tubular section 275, in this embodiment of a rigid or semi-rigid material.

The flexible coupling 220 is a resilient element which allows for movement of the mouthpiece 218 relative to the nosepiece 247, in this embodiment an asymmetric translation of the mouthpiece 218 relative to the nosepiece 247.

The present inventors have determined that the provision of asymmetric translation of the mouthpiece 218 relative to the nosepiece 247 when the mouthpiece 218 is moved, and specifically in a manner which provides for greater movement in a direction along the axis of the nosepiece 247 than in a direction laterally to the nosepiece 247, provides an arrangement which allows for improved patient compliance and efficacy.

In this embodiment the distal end D of the mouthpiece 218 is configured to move a distance Y at least 1.5 times greater in a direction parallel to the axis of the nosepiece 247 than in a direction X orthogonally to the axis of the nosepiece 247. More preferably, the distal end D of the mouthpiece 218 is configured to move a distance at least 1.75 times or at least 2 times greater in a direction Y parallel to the axis of the nosepiece 247 than in a direction X orthogonally to the axis of the nosepiece 247.

In this embodiment the flexible coupling 220 comprises an annular coupling member 277 which is attached in one part to the housing 215 and another part to the tubular section 275 of the mouthpiece 218, such that exhalation through the mouthpiece 218 delivers an air flow into the capsule-receiving unit 216.

In this embodiment the coupling member 277 is configured to provide a hinge section 279, here, to one, upper side thereof, proximate the nosepiece 247, about which the mouthpiece 218 is preferentially hinged when biased upwardly or downwardly by the application of a biasing force F.

In this embodiment the coupling member 277 has a shorter dimension to the one, upper side, thereby ensuring that the mouthpiece 218 is hinged about the one, upper side, and a progressively-increasing dimension to the other, lower side, distal the nosepiece 247.

In this embodiment the coupling member 277 has an arcuate, bowed profile 280 which becomes larger towards the other lower side, and allows for stretching in the event of the mouthpiece 218 being biased upwardly, and compression in the event of the mouthpiece 218 being biased downwardly.

In this embodiment the profile section 280 is bowed such that the biasing force required to bias the mouthpiece 218 upwardly is less than the biasing force required to bias the mouthpiece 218 downwardly.

In this embodiment the coupling member 277 is configured to provide the axis of the mouthpiece 218 at an angle of about 50 degrees relative to the axis of the nosepiece 247, and allow for the mouthpiece 218 to be moved upwardly through an angle of about 12 degrees to enclose an angle of about 38 degrees relative to the axis of the nosepiece 247 and downwardly through an angle of about 7 degrees to enclose an angle of about 57 degrees relative to the axis of the nosepiece 247.

In an alternative embodiment the coupling member 277, instead or in addition to having a bowed profile section 280, can be formed of graded material, such that the material of the coupling member 277 is less resilient at the one, upper side than the other, lower side.

In this embodiment the coupling member 277 is formed of a thermoplastic elastomer (TPE), preferably having a durometer of 50.

The capsule-piercing mechanism 220 comprises an actuator button 281 which extends through the lateral aperture 222 in the housing 215 such as to allow for operation by the subject, a plurality of, in this embodiment first and second piercing elements 283, 285 which are supported by the actuator button 281 and extend forwardly thereof, such that, on depression of the actuator button 281 from a retracted position to an extended position, the piercing elements 283, 285 are driven through respective ones of the piercing apertures 271, 273 in the lateral wall of the capsule-containing member 249 to pierce the capsule C.

In this embodiment the capsule-piercing mechanism 220 includes a resilient element 287 which acts to bias the actuator button 281 outwardly towards the retracted position, such that, following depression of the actuator button 281 to pierce the capsule C, the actuator button 281 is returned to the retracted position. In this embodiment the resilient element 287 is formed as an integral part of the actuator button 281, but in other embodiments could be provided by a separate element, such as a compression spring.

Exemplary operation of this delivery device will now be described hereinbelow.

Firstly, taking the delivery device in hand, and with a nosepiece unit 217 inserted in the housing 215, the subject depresses the actuator button 281 of the capsule-piercing mechanism 220 such as to pierce the capsule C as contained in the capsule-containing member 249.

By depressing the actuator button 281, the capsule C is pierced by the piercing elements 283, 285 at two locations spaced along the axial length thereof.

The actuator button 281 is then released, which causes the actuator button 281 to be returned to the retracted position under the bias of the biasing element 287. In this way, the delivery device is primed and ready for use.

The subject then inserts the nosepiece 247 into one of his/her nasal passages until the nosepiece 247 abuts the nares of the nostril such as to establish a fluid-tight seal therewith, at which point the distal end of the nosepiece 247 extends about 2 cm into the nasal passage of the subject, and grips the mouthpiece 277 in his or her lips.

The subject then begins to exhale through the mouthpiece 218, which exhalation acts to close the oropharyngeal velum of the subject and drive an air flow through the nasal airway of the subject, with the air flow passing into the one nasal passage, around the posterior margin of the nasal septum and out of the other nasal passage, thereby achieving a bi-directional air flow through the nasal airway of the subject.

When the subject exhales with sufficient force, the capsule C is lifted from the seat as defined by the inlet aperture 265 of the capsule-containing member 249 and the capsule C is rotated, which rotation acts to release the substance from within the capsule C which is entrained by the exhaled air flow and delivered to the posterior region of the nasal cavity of the subject. With continued exhalation, the capsule C continues to rotate.

Further, in this device, the capsule C is configured to vibrate, and through the sound transmission path as provided by the nosepiece unit 217 being inserted into the nostril, this vibration acts to promote ventilation of the nasal airway, particularly in the posterior region of the nasal cavity. It is postulated that this vibration contributes to efficacy, as outlined in the studies described hereinbelow.

This operation of the delivery device is then repeated with a new nosepiece unit 217, with the device being fitted to the other, second nasal passage. In this embodiment the entire nosepiece unit 217 is replaced, but in other embodiments either the capsule-containing member 249 or just the capsule C could be replaced.

The gas may be delivered at a pressure of 2, 3, 4, 5, 6, 7, 8, 9 or 10 kPa.

The present disclosure will now be described herein with reference to the following non-limiting Examples.

Example #1

The primary purpose of this study was to study the onset of headache relief following a dose of sumatriptan. This study also evaluated the efficacy and safety and tolerability following sumatriptan treatment. Headache relief is defined as a reduction from moderate (Grade 2) or severe (Grade 3) to none (Grade 0) or mild (grade 1) pain on the International Classification of Headache Disorders ($2^{nd}$ Edition) criteria.

The study sample included 436 subjects. Study treatments included (i) 16 mg of sumatriptan powder administered to the nasal passage intranasally with the Breath Powered™ delivery device of FIGS. 2(*a*) and (*b*) together with an oral tablet placebo, and (ii) administration of a 100 mg oral sumatriptan tablet (Imitrex® 100 mg Tablet or approved or generic equivalent), in which 100 mg of sumatriptan was administered orally, in conjunction with use of the Breath Powered™ administration system but containing no active substance.

Figure 2B:
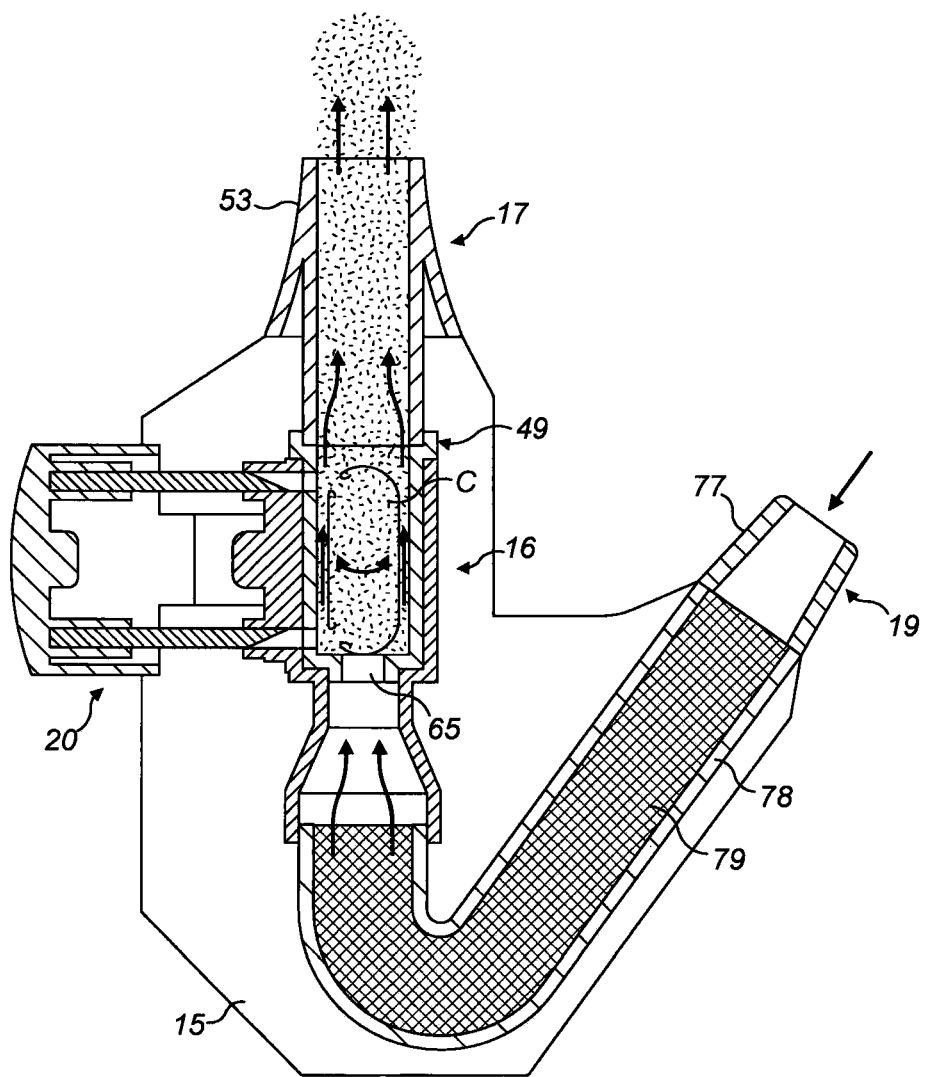

The study compared headache relief at 30 mins following intranasal administration of a delivered dose of 16 mg of sumatriptan using the Breath Powered™ delivery device of FIGS. 2(*a*) and (*b*) with the oral administration of 100 mg of sumatriptan in the acute treatment of single migraine attack.

FIG. 5 summarizes the response rates in this study at 30 mins and 120 mins following administration. As can be seen, the combination of the oral administration of 100 mg of sumatriptan and the placebo device provided a response rate of 39% at 30 mins. The combination of the administration of 16 mg of sumatriptan using the Breath Powered™ device of FIGS. 2(*a*) and (*b*) and an oral tablet placebo provided a response rate of 67% at 30 mins.

A potential mechanism for the earlier onset of action of sumatriptan may be attributed to the fact that carbon dioxide may inhibit the sensory nerve activation and calcitonin gene-related peptide (CGRP) release, and the flow pattern of the carbon dioxide and drug may also play a role. A higher air pressure of from 3 to 7 kPa is delivered through the devices of the present device, which may allow the drug and carbon dioxide to reach the posterior region of the nasal cavity, and in particular target the trigeminal nerve V1. The combination of the carbon dioxide exposure and the mucosal pressure may be advantageous. Carbon dioxide may counteract the NO effect and promote CGRP release. The pH of the nasal mucosa may also change when exposed to a higher pressure and concentration of carbon dioxide.

Example #2

This study included a randomized, open-label, single-dose, crossover comparative bioavailability study in healthy subjects.

The study sample included 20 male and female subjects, 18-55 years of age, who were judged healthy by the investigator, with no clinically relevant abnormalities as determined by medical history, physical examination, blood chemistry, hematology (including complete blood count), urinalysis, vital signs, and electrocardiogram (ECG). Eligible subjects had a body mass index (BMI) of 18-32 kg/m$^2$ and a body weight of not less than 50 kg. Prior to inclusion, subjects agreed to abstain from alcohol intake from 48 hrs before each administration of study medication and during the period of confinement, and to limit caffeine/methylxanthine intake to less than 300 mg/day for 7 days prior to and for the duration of the study, with no intake from 24 hrs before dosing and throughout confinement. Subjects also agreed not to consume food or beverages containing grapefruit, Seville oranges, or quinine (e.g. tonic water) 72 hrs prior to study day −1 until after the last pharmacokinetic sample had been collected, and not to consume food containing poppy seeds during the study. Subjects had verified air flow through both nostrils, an ability to close the soft palate (e.g., ability to inflate a balloon) and were able to use the Breath Powered™ device of FIGS. 2(*a*) and (*b*) correctly.

Subjects with a history of migraines, a history of hypersensitivity or allergies to any drug, including sumatriptan or any of its components, or sulphonamides were excluded. Subjects were ineligible if they had a hemoglobin level below the lower limit of normal at screening, had donated blood or experienced significant blood loss (>500 mL)

within 3 months prior to screening, or were planning to donate blood within 2 months of completing the study. Use of drug metabolizing enzyme (CYP-450) inducers within 28 days prior to dosing or inhibitors within 14 days prior to dosing, use of any monoamine oxidase inhibitors within 28 days prior to dosing, use of any prescription medications/products, except hormonal contraceptives in female subjects of childbearing potential, and use of any over-the-counter non-prescription preparations (except ibuprofen and acetaminophen used at recommended doses) within 14 days of study entry, all resulted in exclusion. Pregnant and lactating females were excluded. The presence of respiratory diseases or known nasal obstruction, including allergic rhinitis, nasal septum deviation, polyposis, severe mucosal swelling, nasal ulcers, nasal trauma, or for any other reason, a history of chronic nose bleeds, current nasopharyngeal illness, and known velum insufficiency also resulted in exclusion.

The study consisted of six visits. At the first visit, subjects were screened for eligibility. Following a physical examination, subjects were instructed on the use of the Breath Powered™ delivery device of FIGS. 2(a) and (b). Once the subject demonstrated an ability to appropriately use the device, the remaining screening procedures (vital signs, ECG recording, blood and urine sampling for clinical laboratory tests, alcohol and drugs of abuse tests, serum pregnancy test [women only]), were performed.

Eligible subjects attended the clinic for four additional visits (visits 2-5). At each visit, subjects checked-in to the study site the evening before dosing and remained there until after the last blood sample for determining sumatriptan concentration had been drawn. Randomization was generated by Celerion Bioanalysis Laboratory (Lincoln, Nebr., USA). Subjects were randomly assigned to treatment sequence using a 4-by-4 Latin square design at the first treatment visit (visit 2). The study treatments were (i) 20 mg of sumatriptan powder administered intranasally with the Breath Powered™ device of FIGS. 2(a) and (b), yielding a delivered dose of 16 mg; (ii) 20 mg sumatriptan nasal spray (Imitrex® 20 mg Nasal Spray or approved or generic equivalent); (iii) 100 mg oral tablet (Imitrex® 100 mg Tablet or approved or generic equivalent); and (iv) 6 mg subcutaneous injection (Imitrex® 6 mg SC or approved or generic equivalent). Each subject received each of the four treatments on the four separate periods at approximately the same time at each visit, with a 7-day washout between treatments. The subjects fasted for at least 8 hrs before dosing and up to 4 hrs post-dose.

For dosing of sumatriptan powder with the Breath Powered™ device of FIGS. 2(a) and (b), subjects first self-administered a first dose of substance from a first nosepiece unit 17 (the capsule C containing 11 mg of free base of sumatriptan, with 7-8 mg being the average delivered dose) into one nostril and then self-administered a second dose of substance from a second nosepiece unit 17 (again the capsule C containing 11 mg of free base of sumatriptan, with 8 mg being the average delivered dose) into the other, second nostril. For dosing with the nasal spray, subjects were first instructed on appropriate administration and then subjects self-administered a single dose of 20 mg sumatriptan to one nostril. The oral tablet was taken by subjects with 240 mL water. For the sub-cutaneous injection, the investigator or designee made the injection of the 6 mg dose of sumatriptan in the subject's abdomen.

Subjects returned at a final visit (visit 6) for follow-up evaluations between 3 and 10 days after the last blood draw for sumatriptan concentration determination. Safety evaluations were based on reports of adverse events (AEs), physical examination, clinical laboratory tests, vital signs and ECG measurements.

Blood samples (5 mL) were collected in tubes containing K2EDTA at pre-dose (time 0) and 2, 5, 10, 15, 20, 25, 30, 45 mins, 1, 1.5, 2, 3, 4, 6, 8, 10, 12 and 14 hrs post-dose. The plasma fraction was separated by placing the collection tube into a refrigerated centrifuge (2-8° C.) for 10 mins at 1,500×g. All plasma samples were stored frozen at −20° C. until shipped to the bioanalytical facility. Plasma samples were analyzed for sumatriptan at the Celerion Bioanalysis Laboratory (Lincoln, Nebr., USA) using a validated LC-MS/MS method. The lower limit of quantitation (LLOQ) was 0.1 ng/mL, and all concentrations below the LLOQ were treated as 0 for the calculations of descriptive statistics and the PK parameters. All PK parameters were calculated using a non-compartmental approach in WinNonlin Professional® Version 5.2 (Mountain View, Calif., USA) and SAS® (Release Version 9.1.3, SAS Institute Inc., Cary, N.C., USA). The PK parameters calculated are listed below.

| | |
|---|---|
| $C_{max}$ | maximum observed drug concentration |
| $t_{max}$ | time to reach $C_{max}$ |
| $AUC_{0-t}$ | area under the drug concentration-time curve from time zero to time t, where t is the time of the last measurable concentration $[C_p]$, calculated using the linear trapezoidal rule |
| $AUC_{0-\infty}$ | area under the drug concentration-time curve from time zero to infinity, calculated as $AUC_{0-\infty} = AUC_{0-t} + C_p/\lambda_z$ |
| $AUC_{0-15\ min}$ | area under the drug concentration-time curve from time zero to 15 mins |
| $AUC_{0-30\ min}$ | area under the drug concentration-time curve from time zero to 30 mins |
| $t^{1/2}$ | terminal elimination half-life, calculated as $\ln(2)/\lambda_z$ where $\lambda_Z$ is the apparent first-order terminal elimination rate constant calculated from a semi-log plot of the concentration vs time curve by linear least-squares repression analysis |
| $\lambda_Z$ | terminal elimination rate constant |
| AUC | percentage of $AUC_{0-\infty}$ extrapolated from $C_p$ to infinity, calculates as $100 \times [1 - (AUC_{0-t}/AUC_{0-\infty}]$ |

The sample size was based on practical considerations rather than statistical power. A sample size of 20 subjects provided at least 5 replications within each sequence using a 4-by-Latin square design and was judged to provide a robust evaluation of PK parameters.

The plasma concentrations and PK parameter values were imported into SAS® which was used to calculate all descriptive statistics. An analysis of variance (ANOVA) on the In-transformed PK parameters $AUC_{0-\infty}$, $AUC_{0-t}$, $AUC_{0-30}$, and Cmax of sumatriptan was used to compare treatments. The ANOVA model included sequence, treatment, and period as fixed effects and subject nested within sequence as a random effect. Sequence effect was tested using subject (sequence) as the error term at a 5% level of significance. Each ANOVA included calculation of least-squares (LS) means, the difference between treatment LS means, the standard error, and 90% confidence intervals (CI) associated with this difference. The LS means, difference between LS means, and 90% CI of each difference were exponentiated to the original scale. Two treatments are considered bioequivalent only if the 90% CI of the treatment difference is fully contained within the accepted bounds of 80-125%.

The plasma concentration-time profile of sumatriptan was well characterized for each of the four treatments (FIG. 6). Overall exposure from both of the intranasally administered sumatriptan treatments was considerably lower than sumatriptan delivered by either the oral or sub-cutaneous route. The mean plasma concentration-time profiles up to 4 hrs post-dose for the two intranasal treatments demonstrate a clearly differentiated profile following delivery by the Breath Powered™ device of FIGS. 2(a) and (b) (FIG. 7): in the first 30 mins following dosing, sumatriptan powder from the Breath Powered™ device of FIGS. 2(a) and (b) produced a faster rise in plasma sumatriptan concentration and a substantially greater exposure as compared with the conventional liquid sumatriptan nasal spray.

A summary of the PK parameters for the four treatments is presented in FIG. 8. There were no first point $t_{max}$ values and the mean residual area (defined as $AUC_{\%\ extrap}$) was approximately 5% or less for all treatments. Intranasal administration of sumatriptan powder using the Breath Powered™ device of FIGS. 2(a) and (b) resulted in a 27% higher peak exposure ($C_{max}$), and a 75% higher early exposure ($AUC_{0-15}$) relative to the sumatriptan nasal spray, despite a 20% lower delivered dose. On a dose-adjusted basis, this represents a 59% higher peak exposure and 119% higher early exposure. The extent of systemic exposure as measured by $AUC_{0-t}$ and $AUC_{0-\infty}$ over 14 hrs was similar for the Breath Powered™ device of FIGS. 2(a) and (b) and the nasal spray liquid sumatriptan. In contrast, the sumatriptan powder delivered with the Breath Powered™ device of FIGS. 2(a) and (b) produced a substantially lower peak and overall systemic exposure relative to both the 100 mg oral sumatriptan tablet and the 6 mg sub-cutaneous sumatriptan injection. Although the absorption profile curve for both intranasal products was characterized by bi-modal peaks consistent with a combination of early nasal absorption followed by late gastrointestinal absorption, these products did not show the same pattern (FIG. 7). The early peak was higher using the Breath Powered™ delivery device of FIGS. 2(a) and (b), while the later peak was higher with nasal spray delivery.

The apparent terminal elimination half-life, at approximately 3 to 4 hrs, was comparable following the two intranasal treatments and the oral tablet, but was shorter for the sub-cutaneous injection at approximately 2 hrs.

Statistical comparisons of the plasma sumatriptan PK parameters using geometric means are summarized in FIG. 9. Although the overall extent of systemic exposure (not dose adjusted) was similar for delivery of sumatriptan powder using the Breath Powered™ delivery device of FIGS. 2(a) and (b) and the conventional liquid nasal spray, the peak exposure and cumulative exposure in the first 30 mins post-dose was approximately 20% and 52%, respectively, higher for sumatriptan powder delivered using the Breath Powered™ delivery device of FIGS. 2(a) and (b), suggesting that more sumatriptan reaches the systemic circulation early after dosing despite the delivery of an approximately 20% lower dose (16 mg vs 20 mg). Relative to both oral tablet and sub-cutaneous injection, the peak and overall exposure following sumatriptan powder delivered intranasally by the Breath Powered™ device of FIGS. 2(a) and (b) was substantially lower.

Quantitative measurement of residuals in used Breath Powered™ devices of FIGS. 2(a) and (b) demonstrated that the devices delivered 8±0.9 mg (mean±SD) of sumatriptan powder in each nostril (providing an average total delivered dose of 16 mg). Although the extent of systemic exposure over 14 hrs was similar following delivery of 16 mg of sumatriptan powder using the Breath Powered™ delivery device of FIGS. 2(a) and (b) and 20 mg of liquid sumatriptan using the sumatriptan nasal spray ($AUC_{0-\infty}$ 64.9 ng*hr/mL vs 61.1 ng*hr/mL), the present delivery of sumatriptan powder, despite being a 20% lower dose, produced 27% higher peak exposure ($C_{max}$ 20.8 ng/mL vs 16.4 ng/mL) and 61% higher exposure in the first 30 mins compared to the conventional liquid nasal spray ($AUC_{0-30}$ min 5.8 ng*hr/mL vs 3.6 ng*hr/mL). The magnitude of difference is larger on a per-milligram basis, allowing equivalent doses to be delivered with reduced risk or the delivery of a reduced dose at significantly reduced risk. The absorption profile following standard nasal spray demonstrated bi-modal peaks, consistent with lower early followed by higher later absorptions. In contrast, the profile following delivery using the Breath Powered™ delivery device of FIGS. 2(a) and (b) showed higher early and lower late absorptions.

Relative to the 100 mg oral tablet ($C_{max}$, 70.2 ng/mL, $AUC_{0-\infty}$, 308.8 ng*hr/mL) and 6 mg injection ($C_{max}$ 111.6 ng/mL, $AUC_{0-\infty}$, 128.2 ng*hr/mL), the peak and overall exposure following intranasal delivery of sumatriptan powder using the Breath Powered™ delivery device of FIGS. 2(a) and (b) was substantially lower.

The PK characteristics of the delivery of sumatriptan powder using the Breath Powered™ delivery device of FIGS. 2(a) and (b) in the present study show that the initial rate of rise in plasma concentration was faster using the Breath Powered™ delivery device of FIGS. 2(a) and (b) than following either the delivery of 20 mg of sumatriptan in a nasal spray or the delivery of 100 mg of sumatriptan in an oral tablet.

Comparison of various oral and parenteral formulations of sumatriptan indicate that the rate of increase in plasma concentration during the initial period of absorption gives a good indication of efficacy, and may in part explain the similar clinical efficacy of 20 mg of sumatriptan delivered in a conventional nasal spray to that of 100 mg of sumatriptan administered as an oral tablet despite significant differences in plasma levels. It may also explain the efficacy at 60 mins observed with the delivery of sumatriptan powder using the Breath Powered™ delivery device of FIGS. 2(a) and (b) in migraine patients.

Evaluation of the mean absorption profile for the two forms of intranasal administration reveals some key differences. Unlike the range of currently available sumatriptan injection products, which are bioequivalent, PK profiles demonstrate that the Breath Powered™ delivery device of FIGS. 2(a) and (b) and the conventional liquid nasal spray are not bioequivalent. With the liquid nasal spray, there is a pronounced hybrid absorption pattern with a dual peak, suggesting proportionately lower intranasal absorption followed by a higher degree of what is most likely gastrointestinal absorption, consistent with a large portion of the delivered dose being swallowed. In contrast, the early peak is more pronounced after delivery of sumatriptan powder using the Breath Powered™ delivery device of FIGS. 2(a) and (b), suggesting a larger proportion of the delivered dose is intranasally absorbed. As presented in FIG. 8, differences between the delivery of sumatriptan powder using the Breath Powered™ delivery device of FIGS. 2(a) and (b) and the standard liquid nasal spray, respectively, are also evident in several metrics characterizing the absorption profiles even before performing dose adjustment for delivered dose, including $C_{max}$ (20.8 vs 16.4 ng/mL), $AUC_{0-30}$ (5.8 ng*hr/mL vs 3.6 ng*hr/mL) and $AUC_{0-15}$ (2.1 ng*hr/mL vs 1.2 ng*hr/mL). The delay in time to maximum concentration associated with the conventional nasal spray relative to the delivery of sumatriptan powder using the Breath Powered™ delivery device of FIGS. 2(a) and (b) (median $t_{max}$, 1.5 hr vs. 0.75 hr, respectively) is also consistent with the Breath Powered™ delivery device producing a higher proportion of early nasal absorption. However, median $t_{max}$ values should be interpreted with caution in the context of bi-modal absorption profiles.

It is worth noting that the sumatriptan powder was administered to two nostrils while the nasal spray was administered to a single nostril. The impact of administering liquid sumatriptan nasal spray in divided doses between both nostrils on the pharmacokinetic profile has been previously investigated and found not to impact either the rate or extent of absorption over administration to a single nostril. Therefore, it is unlikely that this difference in administration procedure explains the findings of the current study.

The dose of sumatriptan powder loaded into the pair of drug capsules delivered using the Breath Powered™ delivery device of FIGS. 2(a) and (b) was approximately 20 mg. However, the measured mean delivered dose was 16 mg, which is 20% lower than the 20 mg of sumatriptan delivered with the conventional nasal spray. This smaller delivered dose accentuates the differences in both the rate and extent of absorption observed between the two different intranasal delivery approaches.

Sumatriptan liquid nasal spray has not been widely used. This may in part be reflective of a lack of motivation due to few significant perceived benefits associated with the nasal spray, which is limited by the inherent inadequacies of nasal spray delivery. Given that in many subjects a large portion of drug is absorbed from the gastrointestinal tract, the difference between intranasal delivery and oral delivery may not be observable in many patients. The Breath Powered™ delivery device of the present study avoids many of the delivery inadequacies of a typical spray by distributing powder to the area beyond the nasal valve, producing an absorption profile consistent with proportionately more intranasal and less gastrointestinal absorption. The resulting large difference in speed and extent of absorption at the earliest time points after treatment is likely due to a more extensive absorption from the nasal cavity. This study evaluated healthy volunteers; however, a shift towards proportionately greater nasal absorption may be especially important in the clinical context of a migraineur, where the differences between oral dosing and dosing using the Breath Powered™ delivery device of FIGS. 2(a) and (b) may be more pronounced than in healthy volunteers. Multiple studies have shown delayed gastric emptying in patients with migraine headache, suggesting risks to reliability and speed of medication absorption after oral dosing and a "rightward shift" of the oral PK curve in such patients. Because a rapid rate of increase in sumatriptan blood levels has been hypothesized to produce a faster speed of onset or higher magnitude of treatment efficacy, it is important to note that use of the Breath Powered™ delivery device of the present study was associated with a more rapid initial rate of increase than either oral administration or administration by nasal spray. Additional theoretical benefits associated with achieving true intranasal deposition augmented by the positive pressure generated by exhaled breath include delivery of drug and carbon dioxide to the first branch of the trigeminal nerve and the parasympathetic sphenopalatine ganglion, and possible associated stimulation of the same.

Tolerability or safety concerns are sometimes associated with use of injected and oral triptans. This study found there was significantly lower peak and overall systemic exposure following use of the Breath Powered™ delivery device of the present study as compared with either the tablet or the injection. Reduced exposure translate into a better safety and tolerability profile, that is, having lower associated risk for a given dose. This study found use of the Breath Powered™ delivery device of FIGS. 2(a) and (b) in delivering sumatriptan powder to be safe and well tolerated by healthy subjects, with no systemic adverse events and only a single subject reporting dysguesia. In contrast, 4 subjects experienced flushing following the sub-cutaneous injection, and 3 subjects each reported nausea following the tablet and the injection.

It is concluded that the delivery of sumatriptan powder using the Breath Powered™ intranasal delivery device of FIGS. 2(a) and (b) produced a faster and more efficient absorption profile when compared with nasal spray and a substantially lower level of exposure than either the tablet or injection.

Example #3

This study investigated the delivery of sumatriptan using the Breath Powered™ delivery device of FIGS. 2(a) and (b) and a conventional nasal spray (Imitrex® 20 mg Nasal Spray or approved or generic equivalent)) in subjects having nitroglycerin (GTN) induced migraines as compared to healthy subjects.

Figure 11:
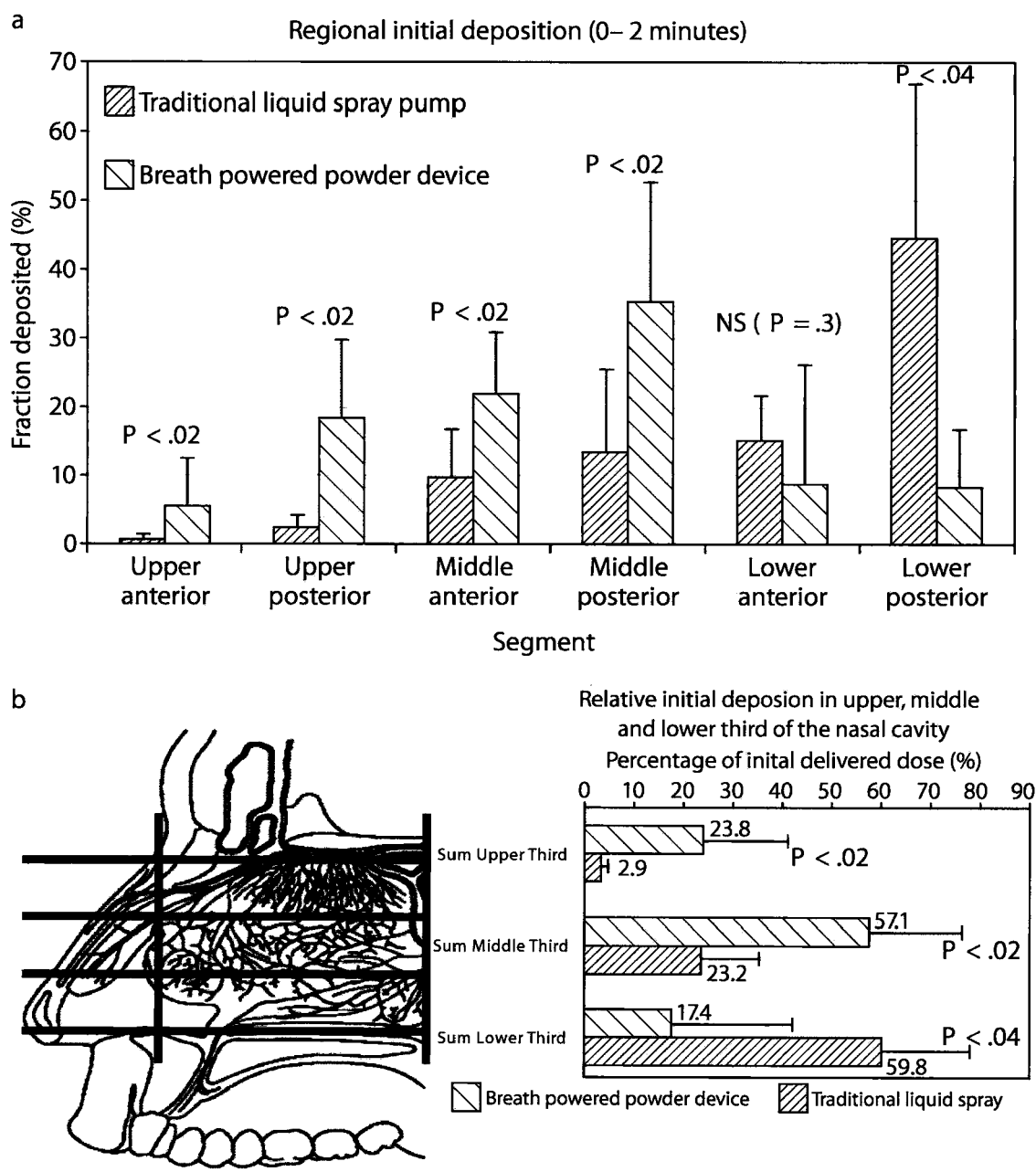

FIGS. 10 to 12 illustrate sumatriptan PK parameters for nitroglycerin (GTN)-induced migraines as compared to sumatriptan PK parameters for healthy subjects obtained using both the Breath Powered™ delivery device of FIGS. 2(a) and (b) and the 20 mg nasal spray.

It is believed that autonomic changes could provide better absorption and effects by unilateral delivery to the side of the migraine. Unilateral activation of the trigeminal nerve could modify the nasal mucosa to offer increased nasal absorption and delayed gastrointestinal absorption. Autonomic activation of the trigeminal nerve could also make the administration of carbon dioxide more efficient and furthermore the mucosa could become more susceptible to pressure. As can be seen from FIG. 10, 7.5 mg of sumatriptan delivered using the Breath Powered™ delivery device of FIGS. 2(a) and (b) to the side of the migraine during a GNT attack in migraineurs resulted in a bioavailability of 27%. The $C_{max}$ for the administration to the side of the migraine is 11, whereas it is only 9.7 for the nasal spray. Administration of 7.5 mg of sumatriptan using the Breath Powered™ delivery device of FIGS. 2(a) and (b) to each of the nostrils does not appear to provide a higher bioavailability.

The delivery of sumatriptan using the Breath Powered™ delivery device of FIGS. 2(a) and (b) is a more efficient form of drug delivery, producing a higher peak and earlier exposure with a lower delivered dose than conventional liquid nasal sprays and provides a faster absorption than either conventional nasal sprays or oral administration. It also produces a significantly lower peak and total systemic exposure than oral tablet or sub-cutaneous injection.

Example #4

This study is a double-blind study comparing the delivery of a nominal dose of 20 mg of sumatriptan bi-laterally using the Breath Powered™ delivery device of FIGS. 2(a) and (b) and a 100 mg oral sumatriptan tablet (Imitrex® 100 mg Tablet or approved or generic equivalent).

The study is a cross-over design where each patient enrolled will treat headaches with each of the treatments. Specifically, patients will treat up to five headaches with a treatment and then cross over to treat up to five headaches with the other. With each headache, the patient uses the Breath Powered™ delivery device of FIGS. 2(a) and (b) and takes a tablet, only one of which will contain the active drug substance sumatriptan.

From unblinded data on over 400 headaches, the results obtained at the 30 min timepoint (headache relief 30 mins after taking medication) for moderate or severe headaches is 54%.

The literature suggests that the response at 30 min from a 100 mg oral tablet of sumatriptan should be around 9-14%. This indicates that the observed response rate with the placebo device is much higher than previously observed with oral tablets alone.

Example #5

Intranasal formulations of dihydroergotamine mesylate (DHE), sumatriptan, zolmitriptan, butorphanol, civamide and lidocaine have all been used/investigated for the treatment of migraine and/or cluster headache. Civamide and lidocaine have been administered via a nasal dropper to interrupt nerve transmission, and, although there has been some evidence of clinical efficacy, neither has received US Food and Drug Administration approval for the treatment of headache. Furthermore, nerve stimulation of the SPG has shown promising results in aborting cluster headache, strongly supporting the potential of local treatment to nerves that may be accessed from the nasal cavity.

DHE, sumatriptan, zolmitriptan, and butorphanol have obtained regulatory approval for the treatment migraine and can be administered in the form of a conventional nasal spray by the patient. DHE is known to be a highly effective medication when administered intravenously. Unfortunately, it is less than 1% bioavailable when given orally. However, when administered intranasally, it has a bioavailability of ~40%, allowing for use of this medication in the outpatient setting. In addition to the intranasal formulations, sumatriptan is available as a sub-cutaneous injection, an oral tablet, suppositories, and a rapid dissolving tablet (outside the United States). In addition to the intranasal formulation, zolmitriptan is available as an oral tablet and fast melt formulation. For both drugs, the intranasal formulations were introduced as alternatives to the oral formulations to overcome the issues of slow onset, reduced GI absorption during headache from slowed motility, as well as the aversion of patients to take oral medications in the presence of nausea.

Both intranasal sumatriptan and intranasal zolmitriptan have demonstrated superiority against placebo in providing relief of migraine symptoms, and intranasal zolmitriptan has been demonstrated to provide earlier relief than the same dose of zolmitriptan oral tablets. Each provides a more rapid absorption than the respective orally administered tablet. However, neither has resulted in a marked increase in total bioavailability relative to oral.

These triptan conventional nasal sprays display a bimodal absorption pattern with a fairly small early peak attributed predominantly to absorption across the nasal mucosa, followed by a later more distinct peak representing GI absorption of the significant amount of drug swallowed after bypassing the nose. For zolmitriptan, the nasal fraction has been quantified in a study and found to account for approximately 30% of the total absorption. A similar study has not been conducted with sumatriptan nasal spray, though sumatriptan liquid nasal spray pharmacokinetics have been studied. It is important to note that the approved dose of zolmitriptan delivered nasally is the same as the highest dose for tablets (5 mg), whereas the range of approved conventional sumatriptan nasal spray doses (5, 10, and 20 mg) is fivefold lower than the approved oral doses (25, 50, and 100 mg). Consequently, the systemic exposure is significantly lower for the range of sumatriptan nasal spray doses compared with the oral formulation, whereas it is similar or even slightly higher with nasal zolmitriptan. The opportunity to deliver a lower dose highlights a potential advantage of delivering sumatriptan nasally (vs zolmitriptan) as the risk for systemic and GI-related side effects relative to the oral formulation may be reduced by lowering the systemic exposure.

Despite the theoretical advantages of intranasal drug administration, there have been impediments to broad adoption for the treatment of migraine headache. For patients, the consequences of the inadequate deposition to the target mucosa achieved with traditional nasal sprays is likely a factor contributing to a lack of perceived clinical benefits over oral treatment. Prospective studies have demonstrated that a driver for patients preferring a nasal spray is speed of onset. In addition, alternative formulations that offer the potential of faster absorption may be preferable over simply increasing the dose of an oral formulation. Enhanced tolerability or safety relative to oral formulations would simply add to patient preference should they accompany a core efficacy benefit like improved speed of onset.

Traditional spray pumps used with nasal sprays result in limited drug deposition to the target sites beyond the narrow triangular-shaped constriction called the nasal valve, which is located approximately 2 cm from the entrance of the nostril. The purpose of the narrow nasal valve, in concert with the complex convoluted nasal passageways, is to filter and condition the inspired air, enhance olfaction, and optimize gas exchange and fluid retention during exhalation. These important functional features of the nose impose important limitations on efficient nasal drug delivery that are too often ignored.

For example, the expanding convex spray plume and high particle speed emitted from a spray bottle will largely impact on the walls of the nasal vestibule. Increasing the propulsive force of the nasal delivery does not alter the fundamental anatomic constraints, as the plume impacts on the first surfaces it reaches, while "sniffing" exacerbates the problem as described later. The anterior segment of the nasal cavity, the nasal vestibule, is lined primarily with nonciliated squamous epithelium, which is less efficient for medication absorption than the ciliated respiratory epithelium beyond the nasal valve. Because of this mismatch between the geometry of the anterior region of the nose and the spray plume, only a small fraction of the spray penetrates beyond the nasal valve, and a large portion of the spray volume remains in the vestibule.

The large volume of liquid in the vestibule of the nose may drip out or be wiped off. Sniffing during delivery further narrows the nasal valve, and reflexive sniffing after delivery to avoid drip-out will not only further narrow the nasal valve, which is already particularly narrow superiorly, but also shrink the already slit-like deeper nasal passages. This tends to impair both the intended targeting to a broad nasal surface area and any potential benefits of higher deposition, and tends to direct whatever medication penetrates the nasal valve along the nasal floor to be swallowed. Taste buds sensing bitter taste located at the base of the tongue are quickly exposed to the concentrated liquid that contributes to the intense bitter taste often reported with these nasal sprays. It is only the smaller proportion of the spray that reaches the highly vascularized respiratory mucosa that accounts for most of the early nasal absorption. Such a significant portion of the medication delivered by conventional nasal sprays is swallowed, rather than being nasally absorbed, which the GI tract contributes more to the amount of drug absorbed than does the nose. This phenomenon is observed with sumatriptan where a bimodal absorption profile is produced following conventional nasal spray administration: a lower early peak, likely related to intranasal absorption, is produced after 20 mins and is followed by a higher absorption peak consistent with GI absorption around 90 mins.

The predominance of oral absorption following conventional nasal spray delivery reduces the intended advantages of nasal delivery. Thus, the lack of significant differentiation from oral tablets results in only marginally faster onset of action in some patients and likely contributes to the limited uptake in the market place observed with nasal sprays.

Notably, both the sensory and parasympathetic branches of the trigeminal nerve involved in the pathophysiology of migraine and other headaches innervate the mucosal surfaces beyond the nasal valve, which is also where the SPG resides. To the extent that these structures are involved in headache pathophysiology, the posterior and superior portion of the nasal cavity presents a target for therapeutic intervention with current or future drugs; however, they cannot be effectively reached with a standard nasal spray.

A comprehensive review on deposition patterns associated with nasal drops and spray pumps concluded that traditional delivery devices are suboptimal for delivery to the respiratory mucosa beyond the nasal valve. Several approaches attempting to improve the drug delivery of traditional spray pumps have been suggested and tested over the years, but are generally either impractical, suboptimal, or have yet to be proven in replicated human intranasal deposition studies. Efforts to optimize conventional nasal sprays by improving the method of use have been similarly unrewarding: a study tested 7 different head and body positions using traditional nasal sprays and concluded that there is "no best method."

The Breath Powered™ Bi-Directional™ delivery mechanism described herein can be implemented in simple devices without electromechanical cost or complexity, and overcomes many deficiencies of traditional nasal delivery. Both liquid and powder drugs can be delivered using such devices. This nasal delivery concept consists of devices with a flexible mouthpiece and a shaped, sealing nosepiece. It is designed to exploit unique aspects of the nasal anatomy and physiology to improve the extent and reproducibility of drug delivery to target sites in the nose beyond the nasal valve while avoiding the risk of lung inhalation.

In one operation, the user slides the shaped nosepiece into one nostril to create a seal with the nasal tissue, inserts the mouthpiece between the open lips, takes a deep breath, closes the lips around the mouthpiece, and then exhales forcefully into the mouthpiece. The oral exhalation into the device creates a positive pressure in the oropharynx, naturally elevating and sealing the soft palate and completely separating the nasal and oral cavities. Because of the sealing nosepiece, the airflow and dynamic positive pressure is transferred by the device into the nasal cavity where it expands the nasal valve and narrow slit-like passages. The intranasal pressure, which is slightly reduced compared with the intraoral driving pressure due to the resistance of the device and the nasal passage, balances the pressure across the soft palate to generally avoid over elevation of the soft palate. This generally maintains patency of the communication pathway between the two nostrils that is located deep in the nasal cavity posterior to the nasal septum, permitting the exhaled breath to escape from the contralateral nostril while relieving the nasal cavity of excess pressure.

A dedicated multiuse Breath Powered™ powder device with a reusable device body and a disposable nosepiece was developed for use in patients with migraine headache. An 11-mg dose of sumatriptan powder is filled into a standard respiratory capsule and provided to the patient in a capsule chamber of a disposable nosepiece. There can be a small entrance for airflow at the bottom of the chamber and a larger opening at the top. Prior to use of the device, a fresh nosepiece can be snapped into the top of the device, and the capsule may be pierced by depressing a button on the device body. Upon exhalation into the device, the pierced capsule can vibrate and/or rotate with the exhaled breath, releasing the powder into the airflow. Drug particles are carried posteriorly by the expanding flow of physiologically warmed air into one nostril, beyond the nasal valve, and can be deposited broadly throughout the deep nasal cavity before the air reverses course and escapes anteriorly through the other nostril, providing bi-directional delivery.

Multiple studies evaluating anthropometric differences between individuals were conducted in order to develop the appropriate design of the device in order to accommodate differences in individual nostril size and distances and angles between the mouth and nose. The current design has been found in usability testing as well as clinical trials to be well accepted in terms of comfort and ease of use.

The scintigraphic techniques used in the last decades to study in vivo nasal deposition of liquid and powder formulations are relatively crude and did not allow for reliable absolute or relative quantification of regional nasal deposition and clearance patterns. An improved system allowing reliable quantification of the regional nasal deposition of radiolabeled particles in human subjects has been introduced and used in clinical deposition trials comparing conventional nasal spray devices to Breath Powered™ devices for both liquid and powder drugs.

In the most recent study, Tc99m-labeled lactose powder was delivered with the Breath Powered™ powder device. A capsule fill and particle size profile similar to sumatriptan powder was used. For measuring differences in deposition, the nose was divided into 3 horizontal segments, and a vertical dividing line was positioned at the head of the inferior turbinate, and radiation counts within each segment were quantified after administration.

The Breath Powered™ powder device demonstrated a broader deposition on the regions where nasal mucosa is lined by ciliated respiratory epithelium (especially upper and middle posterior regions, but also the upper anterior and middle anterior regions) with less deposition in the nonciliated nasal vestibule and significantly greater initial deposition to the upper posterior regions beyond the nasal valve compared with the conventional spray delivery (~54% vs 16%) (FIG. 11a). In contrast, liquid sprays deposited most of the dose (~60% vs ~17%) in limited regions in the lower parts of the nose (FIGS. 11a, b).

The regional analyses of deposition and clearance clearly demonstrate that the Breath Powered™ powder device provides broader exposure to the highly vascularized respiratory mucosa beyond the nasal valve, and particularly improves delivery to the middle and upper regions of the nasal cavity. This should reasonably be expected to translate into more rapid and more extensive drug absorption of suitable medications than is achieved with standard nasal spray delivery. This difference should be possible to measure objectively, as it should be reflected in improved PK and ultimately in improved efficacy. Such studies have now been performed assessing the consequences of delivering sumatriptan in this fashion.

Two studies have evaluated the PK of Sumatriptan delivered with the Breath Powered™ device. One was a crossover study in 12 migraine patients pretreated with either sub-cutaneous (SC) injection sumatriptan, or sumatriptan powder delivered with a Breath Powered™ device, prior to a challenge with nitroglycerine known to induce migraine (GTN-challenge). 40 The larger second study was a 4-way crossover study in healthy volunteers comparing sumatriptan powder delivered with a Breath Powered™ device (15 mg delivered dose split between nostrils) to 20 mg sumatriptan nasal spray (1 nostril), 100 mg sumatriptan tablet, and 6 mg sumatriptan SC injection. In both studies, there was a bimodal absorption pattern representing an initial nasal absorption followed by a GI absorption with Breath Powered™ delivery (FIG. 12). The initial peak observed in both studies was more pronounced than the peak observed with the standard nasal spray (as measured in the second study), indicative along with other PK parameters of a more efficient and faster systemic absorption with the Breath Powered™ device (FIG. 12). Absorption also occurred earlier than with tablet delivery but with a significantly lower peak and total systemic exposure than either the oral tablet or sub-cutaneous injection.

The nasal peak for sumatriptan powder is very similar in the two PK studies, one in migraineurs and one in healthy volunteers, occurring early in both populations. However, the later peak, assumed to represent predominantly GI absorption, is substantially smaller in the study performed in migraineurs during GTN-challenge (FIG. 12). This likely reflects the delayed and decreased GI absorption because of autonomic dysfunction observed in migraineurs that is further accentuated during an attack.

It should be noted that sumatriptan powder was split between the two nostrils while the nasal spray was administered to a single nostril. The impact on the PK profile of dividing the liquid spray dose between nostrils has been previously investigated and found not to improve either the rate or extent of absorption over administration to a single nostril. Therefore, it seems unlikely that this difference in administration procedure explains the findings in the PK study in healthy subjects.

It is important to recall when reviewing the pharmacokinetic data that the total delivered Sumatriptan dose with the Breath Powered™ delivery device is 20-25% lower than the sumatriptan 20 mg liquid spray. A shift to greater nasal absorption with Breath Powered™ delivery reduces the fraction of Sumatriptan bypassing the nose compared with sumatriptan spray, and the dose is split between the two nostrils (FIG. 12). The lower delivered dose, broader nasal distribution, and significantly altered clearance pattern (note, the soft palate is usually substantially closed at the time of delivery) following Breath Powered™ delivery further reduce the amount and concentration of drug reaching the taste buds at the base of the tongue, which is likely to mitigate the intensity of the bitter taste sensation. The results show that the enhanced nasal deposition produced by the Breath Powered™ device is indeed associated with pharmacokinetic advantages.

It is reasonable to hypothesize that the increased early absorption may offer advantages in terms of improved efficacy and in particular more rapid onset of pain relief, and that the low dose may enhance tolerability or safety. The ability to prevent migraine attacks in the study with GTN-challenge combined with the similar electroencephalography findings following SC and Breath Powered™ powder delivery, despite much lower blood levels, also suggest potential clinically relevant advantages. These findings provided the rationale to proceed to a randomized placebo-controlled trial with a Breath Powered™ sumatriptan delivery device.

In the first placebo-controlled, parallel group, 3-arm trial in acute migraine (117 total patients), two doses of sumatriptan powder were delivered with the Breath Powered™ device and compared with a "placebo" control group using dummy devices. Fast onset of pain relief was observed for both active doses with early pain relief rates similar to historical data for SC injection despite much lower systemic exposure. Significant benefits were also observed for pain relief at 120 mins for both doses, and the higher dose was selected for further development. The higher dose produced a response of 80% vs 44% with placebo (P<0.01) at 2 hrs, and high early response rates at 60 mins (74% vs 38%, P<0.01) and at 30 mins (54% vs 31%; NS).

A phase III, placebo-controlled, parallel group, 2-arm study in 212 patients was recently conducted with sumatriptan powder being delivered with the Breath Powered™ device. As discussed and shown below, at 2 hrs post-dose, a significant proportion of patients experienced pain relief compared with placebo (68% vs 45%, P<0.01), a high value for triptan therapy. However, again, the most striking result was the fast onset of pain relief, with a remarkably high response rate at 30 mins (42% vs 27%, P<0.05). This is particularly notable in light of the extremely low dose of a triptan medication. The reported adverse events were primarily mild and transient and generally limited to the site of administration. It was concluded that use of the Breath Powered™ delivery device for intranasal delivery of sumatriptan powder is effective, safe, and well tolerated and can offer fast onset of pain relief in adults with acute migraine headache.

Example #6

The objective of this study was to compare the efficacy and safety of delivering sumatriptan powder using the Breath-Powered™ delivery device of FIGS. 2(a) and (b) to a counterpart placebo device in the treatment of patients with moderate to severe migraine headache.

Patients taking oral triptans commonly cite slow onset of action, inadequate pain relief, and adverse effects as reasons for dissatisfaction; nausea or vomiting can also be a barrier to use. Adverse effects (AEs) known as 'triptan effects' are most often associated with formulations and doses that produce higher plasma levels.

In a small trial, a low dose sumatriptan powder delivered with the Breath Powered™ delivery device of FIGS. 2(a) and (b) produced a headache relief rate approaching that previously reported by injection of sumatriptan without the attendant side effects. These results supported conduct of a larger trial.

This study is a single-dose, multicenter, randomized, double-blind, placebo-controlled, parallel-group study. Patients had history of migraine for >1 yr prior to entry and reported >1 headache, but <15 headache days, per month. Patients were randomized to the Breath Powered™ delivery device of FIGS. 2(a) and (b), with first and second doses being delivered to the respective nasal passages using first and second nosepiece units 17 (each including a capsule C containing either 11 mg of sumatriptan powder (yielding an average 7.5 mg emitted dose) or placebo), providing a total average delivered dose of 15 mg. Patients treated an attack reaching moderate or severe intensity and recorded symptoms at scheduled times.

The results are shown generally in FIG. 13. Specifically, 212 patients received treatment (108 using the Breath Powered™ delivery device of FIGS. 2(a) and (b) to deliver sumatriptan powder and 104 using the Breath Powered™ delivery device of FIGS. 2(a) and (b) to deliver placebo). The mean age was 42 yrs.; 85% were women.

For the primary outcome, 68% of patients who received the sumatriptan powder using the Breath Powered™ delivery device of FIGS. 2(a) and (b) reported pain relief at 120 min vs. 45% who received placebo using the Breath Powered™ delivery device of FIGS. 2(a) and (b) ($p<0.01$). Pain relief curves diverged early, reaching statistical significance at 30 min (42% vs. 27%; $p<0.05$), with the Breath Powered™ delivery device of FIGS. 2(a) and (b) providing for a fast onset of pain relief, with a remarkably high response rate at 30 min. At 120 min, 37% of patients receiving sumatriptan powder using the Breath Powered™ delivery device of FIGS. 2(a) and (b) had reported complete relief as compared with 17% who received placebo using the Breath Powered™ delivery device of FIGS. 2(a) and (b) ($p<0.01$), while 70% vs. 45% reported meaningful relief ($p<0.001$).

Among patients with pain relief at 120 min, 65% of patients who received sumatriptan powder using the Breath Powered™ delivery device of FIGS. 2(a) and (b) and 53% who received placebo using the Breath Powered™ delivery device of FIGS. 2(a) and (b) (ns) had continued pain relief at 24 h.

Large reductions in nausea, phonophobia, and photophobia were reported in both groups; between-group differences were not statistically significant. No systemic adverse events were reported in more than one patient. Only one patient reported mild and transient tingling in the hands and head. The most common (>5%) AEs reported were product taste (22%), nasal discomfort (13%), and rhinitis (6%); all transient and generally mild.

This study replicates the previous finding that the delivery of a low dose of sumatriptan powder using the Breath Powered™ device of FIGS. 2(a) and (b) produces early headache relief in a high percentage of patients compared to placebo and to historical rates with oral treatment, and a high rate of headache relief. Treatment was also well tolerated, with few systemic adverse effects.

Comparison of these results with published data suggests that the speed of onset of pain relief with the delivery of sumatriptan powder using the Breath Powered™ delivery device of FIGS. 2(a) and (b) is much faster than oral treatment and approaches that achieved with SC injection, but with substantially lower systemic exposure and therefore the attendant risk of adverse events.

In clinical trials with the Breath Powered™ delivery device of FIGS. 2(a) and (b), an interestingly high placebo response rate has been observed. In these trials, control patients did not receive "no treatment" but used the identical Breath Powered™ delivery device of FIGS. 2(a) and (b) with placebo. Although the high response among these "placebo" patients may be due to chance, secular trends, or other factors, there are potential explanations directly relating to the use of the Breath Powered™ delivery device of FIGS. 2(a) and (b).

During normal respiration, there is minimal exchange of air in the upper narrow part of the nose. The particular aerodynamics of the Breath Powered™ delivery device of FIGS. 2(a) and (b), through which a large amount of exhaled air is blown with about 5-6% carbon dioxide at a flow rate of about 30 L/min or more and lasting for about 2 to about 3 s, which penetrates the upper narrow segments of the nose, could provide therapeutic effects, in part similar to those reported with the delivery of 100% carbon dioxide, albeit that this carbon dioxide delivery was done for short duration and done at low flow (10 mL/s) and low volume. In the present Breath Powered™ delivery device of the present study, it is postulated that the oscillating capsule and air flow may significantly enhance exchange of air in upper narrow parts of the nose, as in part observed in response to humming and pulsating nebulizers. In addition, there are reasons to hypothesize that potential positive effects mediated by the positive air pressure, rapid vibrations produced by the rattling capsule, and the removal of NO may all play a role in alleviating migraine headache. One or more of these, or other, device-related mechanisms may contribute to the high response rate in the placebo groups when using the Breath Powered™ delivery device of the present study.

The deep nasal cavity deposition associated with the Breath Powered™ delivery device of FIGS. 2(a) and (b) enables the potential for medications to be delivered more broadly to mucosal tissue innervated by the trigeminal nerve and to the SPG, which is likely to prove beneficial in the treatment of a range of disorders which are mediated at least in part by the trigeminal nerve or SPG, where stimulation can cause parasympathetic effects. The aerodynamic properties of the Breath Powered™ device itself may offer alternative mechanisms of action and/or synergetic effects.

In addition to possibilities in preemption or prevention of migraine, cluster headache and trigeminal neuralgia represent target indications for possible delivery of numerous new or current drugs alone or in combination, including for example triptans, DHE, lidocaine, nonsteroidal anti-inflammatory drugs (NSAIDs), locally acting corticosteroids, and potentially CGRP-antagonists. There is great unmet need, and it is possible to modify the current device to optimize delivery for treatments intended to particularly target the region closest to the SPG for optimal efficacy. Other potential indications include chronic migraine, where delivery of a very small daily dose of a triptan or other drugs in this manner may offer sufficient receptor blockage to reduce the number of acute attacks. Even topical steroids may prove valuable alone or as an adjuvant therapy in cluster headache or in sinus headache.

Nasal drug delivery has long been a route of administration known to be useful in the treatment of headache and other disorders. However, the typical methods of intranasal delivery are relatively ineffective in their delivery of medication broadly and to the posterior/superior areas of the nasal cavity where rapid and efficient drug absorption and other benefits can effectively accrue. Therefore, the promise of intranasal drug delivery has not been fully realized. Human gamma-deposition studies in vivo with Breath Powered™ delivery device of the present disclosure have proven that this novel device mechanism is capable of producing a significantly improved nasal drug deposition pattern.

Pharmacokinetic studies to assess the consequences of this improved deposition were performed following the delivery of a low dose of sumatriptan powder, and show that this improved delivery is associated with enhanced speed and efficiency of absorption across the nasal mucosa with a reduced proportion of GI absorption relative to standard nasal spray. In replicated clinical trials, use of the Breath Powered™ delivery device of FIGS. 2(a) and (b) for the delivery of low doses to targets mediated at least in part by the trigeminal nerve and/or SPG, has now been shown to produce substantial response rates, with early pain relief more similar to SC injection than to other forms of delivery, but with much lower exposure than with oral or SC treatment. This new form of nasal delivery may offer a number of interesting therapeutic options for the treatment of a range of disorders in the future.

Example #7

This purpose of this study is to compare the delivery of sumatriptan powder using the Breath Powered™ delivery device of FIGS. 2(a) and (b) to the delivery of liquid sumatriptan in a conventional nasal spray.

In this study, 20 mg of sumatriptan dry powder was delivered using the Breath Powered™ delivery device of FIGS. 2(a) and (b), with the delivery being done in two doses using first and second nosepiece units 17 (each containing a nominal dose of 10 mg of free base of sumatriptan, and providing an average delivered dose of 8 mg), yielding a total delivered dose of 16 mg in the nose.

This means that the total exposure to sumatriptan with the Breath Powered™ delivery device of the present study is a lower total milligram dose than tablet, nasal spray or injection. However, directly comparative pharmacokinetic studies show that the delivery of 16 mg of sumatriptan powder using the Breath Powered™ device of FIGS. 2(a) and (b) produces higher peak concentration ($C_{max}$ ng/mL) than a 20 mg conventional liquid sumatriptan nasal spray (Imitrex® 20 mg Nasal Spray or approved or generic equivalent) (20.8 mg vs 16.4 mg, unadjusted for dose). Both intranasal formulations produce a substantially lower peak concentration ($C_{max}$, ng/mL) than either the sumatriptan tablet (Imitrex® 100 mg Tablet or approved or generic equivalent) (100 mg tablet=70.2, 6 ng/ml or the sub-cutaneous injection (Imitrex® 6 mg SC or approved or generic equivalent) (6 mg injection=111.6 ng/ml). Similarly, total drug exposure as measured by area under the curve ($AUC_{0-28}$ ng·hr/mL) is much lower with the intranasal formulations (Breath Powered™ delivery device of the present study=64.9 ng·hr/mL, conventional 20 mg sumatriptan liquid nasal spray=61.1 ng·hr/mL, unadjusted for dose) than with the 100 mg tablet (308.8 ng·hr/mL) or the 6 mg injection (128.2 ng·hr/mL). The sumatriptan powder delivered with the Breath Powered™ delivery device of the present study is not bioequivalent to any tested sumatriptan product. Of particular note, the pharmacokinetics of the sumatriptan delivered with the Breath Powered™ delivery device of FIGS. 2(a) and (b) show a pattern of faster and more efficient absorption than the conventional liquid nasal spray, yielding >60% higher early plasma exposure with an $AUC_{0-15}$ mins of 2.1 for the Breath Powered™ delivery device of the present study vs 1.2 for liquid sumatriptan nasal spray and an $AUC_{0-30}$ mins of 5.8 for the Breath Powered™ delivery device of the present study vs 3.6 for the conventional spray, despite the delivery of 20% less drug.

The Phase 2 randomized controlled trial on BPPSIT published in 2010 included 117 adult subjects with episodic migraine. There were 3 arms, a sumatriptan powder nominal 10 mg arm, a sumatriptan powder nominal 20 mg arm, and placebo. All treatment groups, including placebo, used Breath Powered™ delivery devices. As in the Phase 3 trial discussed later, subjects were instructed to treat when migraine was moderate or severe. The Phase 3 trial used only the 20 mg nominal dose, which as noted delivers 16 mg in the nose, so only those data are reviewed.

In the Phase 2 trial, two-hour pain freedom occurred in 57% of the 20 mg subjects and 25% of the placebo subjects (P<0.05). Two-hour headache relief, defined as headache moving from moderate to severe down to zero or mild, was quite high and statistically significant at 80% for 20 mg, and 44% for placebo. Both doses statistically separated from placebo for headache relief by 60 mins. The most frequent treatment-related adverse event was a metallic taste, occurring in 13% of the 20 mg subjects.

In the Phase 3 regulatory pivotal study on the BPPSIT 20 mg, the TARGET study, there were 223 subjects randomized who received treatment (112 BPPSIT and 111 device loaded with placebo). The primary outcome measure was two-hour headache relief, which occurred in 67.6% of subjects in the BPPSIT group vs 45.2% in the placebo group (P<0.01). For headache relief, BPPSIT reached statistically significant separation from placebo earlier than in the Phase 2 trial, this time at 30 mins (41.7% vs 26.9%; P<0.05). Pain freedom at 2 hrs occurred with 34% of BPPSIT subjects compared with 17% for placebo (P<0.01).

Adverse events occurring >5% included abnormal taste (22%), nasal discomfort (13%), and rhinitis (6%). No serious adverse events occurred in the pivotal trial.

There are a number of issues worth exploring with the BPPSIT data. These include the difference in efficacy between the Phase 2 and Phase 3 studies, overall efficacy, early response, and the placebo response and therapeutic gain (TG). The data from Phase 2 were dramatic with about an 80% headache relief mark at 2 hrs, but in Phase 3, the 2 hr number was not as high, coming in closer to the high end of the conventional triptan range at around 67%, with the 30 min number at 42%, notably higher than has been reported with oral treatment and in the range of injectable triptans. This can probably be accounted for simply by the number of subjects, with more than double the number in Phase 3 than Phase 2. There are numerous instances of clinicians revising their evaluation of a medication from Phase 2 to 3 because of differences in outcomes becoming apparent with a greater number of subjects (N). With smaller numbers of subjects, results are more at the mercy of random variation.

However, it is possible that the response rate is indeed higher with BPPSIT, and one possibility is that the device is the reason. That is, perhaps a higher response accrues when sumatriptan is delivered high up in the nose, close to the lateral margins which abut the pterygopalatine canal containing the sphenopalatine ganglion and the maxillary division of the trigeminal nerve. The possibility of a direct triptan effect on these pivotal structures for migraine and cluster might merit further exploration.

Although headache relief at 2 hrs has been the standard primary outcome variable for most Phase 3 migraine trials, because it is a single time point it does not provide information on the early effects that are considered by patients to be clinically important. For BPPSIT, the response at 30 mins ranged between 42% and 49%. This is a high rate of response for this early time point. Data from randomized controlled regulatory trials included in the Food and Drug Administration-approved prescribing information for nearly all approved triptans provide graphics of pooled efficacy data describing headache response. Review of these graphics reveals that for sumatriptan injection the headache response at 30 mins is in the range of 50%, while 30 mins pain relief is 10-20% for oral formulations, and between 20 and 30% for conventional nasal spray formulations. These data suggest that BPPSIT early response rates may be closer to those observed with injection than has been reported with other non-parenteral delivery forms.

It is interesting that such a low actual dose of 16 mg could have efficacy approaching injection early on, and comparable efficacy at 2 hrs to tablets of 6 times the dose.

Generally, exposure to lower doses with comparable efficacy is attractive when contemplating the potential for adverse events.

Further inspecting the BPPSIT Phase 3 trial, the placebo rate seems quite high, at 45.2% for two-hour headache relief; it was also high at 44% in the Phase 2 trial. In contrast, in Ryan and colleagues' paper summarizing the 2 Phase 3 trials for the conventional sumatriptan liquid nasal spray, the placebo rates for two-hour headache relief were 29 and 35%. There has been a trend for placebo rates to creep up over time in triptan randomized controlled trials. For example, in the trial used to approve sumatriptan oral tablets, the placebo response rate was 17%. There have been numerous hypotheses to explain the rising placebo response rate, including the absence of triptan naïve patients with accompanying rising patient expectations for triptans, and changing study populations as the background pool of patients is influenced by wide availability of triptans.

In the case of BPPSIT, the device itself may be a cause for the high placebo response rate. Many investigators have noted higher placebo rates in the setting of device trials. As one set of investigators noted, "The placebo/nocebo response to sham therapy with a device is similar to that previously reported for prolonged drug treatment. "One possibility for the high placebo response rate in the Phase 3 trial was the novelty and use of the device itself.

A technical reason for the high placebo response may be that this Phase 3 trial had a notably low proportion of severe headaches at baseline at 17%, where previous triptan studies typically have shown a higher proportion of severe headaches. Fewer severe relative to moderate baseline scores would be expected to result in higher placebo response given standard scoring scale and analysis methods.

It is possible that the placebo arm was providing active treatment. The placebo for the BPPSIT trials was treatment with the Breath Powered™ device (pressure with carbon dioxide and lactose powder). While one would think that this was a clear sham treatment, in fact there is a literature on the beneficial effects of carbon dioxide on migraine. Spierings and colleagues found in a preliminary trial available only in abstract form that continuous carbon dioxide infusion for acute treatment of episodic migraine resulted in two-hour pain free responses that were highly statistically significant compared with placebo (25.0% vs 4.8%) (P=0.006).

It turns out that carbon dioxide is probably part of the pain regulatory system. Vause and colleagues wrote about their findings in cultured rat trigeminal ganglion cells in 2007, "Incubation of primary trigeminal ganglia cultures at pH 6.0 or 5.5 was shown to significantly stimulate calcitonin gene-related peptide (CGRP) release . . . carbon dioxide treatment of cultures under isohydric conditions . . . significantly repressed the stimulatory effects of KCl, capsaicin, and nitric oxide on CGRP secretion. carbon dioxide treatment under isohydric conditions resulted in a decrease in . . . capsaicin-mediated increases in intracellular calcium [providing] the first evidence of a unique regulatory mechanism by which carbon dioxide inhibits sensory nerve activation, and subsequent neuropeptide release. Furthermore, the observed inhibitory effect of carbon dioxide on CGRP secretion likely involves modulation of calcium channel activity and changes in intracellular pH.".

Thus, it is possible the carbon dioxide "sham" of the BPPSIT may have been delivering partial treatment and is thus not a real placebo response. The fact that both Phase 2 and Phase 3 studies showed high placebo response rates of 44-45% suggest this possibility. However, there is precedent for high placebo rates in novel triptan delivery trials. In the first rizatriptan orally dissolvable tablet trial, the placebo rate was 47%. We do not know the concentrations of carbon dioxide in the Spierings device to compare with the BPPSIT, and this further limits our opportunity currently to explore this possibility.

Another issue to consider with the BPPSIT Phase 3 data is that of TG, defined as the difference obtained when placebo response is subtracted from active response. The TG in Phase 2 for two-hour headache relief for 20 mg was 36; in Phase 3, it was 22. This second TG at first seems to be on the low end for a triptan. If one were to choose to use TG across studies (and more on that later), in fact, the 2 BPPSIT TGs would appear comparable to those for sumatriptan liquid nasal spray. The TGs in the 5 trials of conventional Sumatriptan liquid nasal spray were 25, 25, 29, 35, and 36.

Sheftell and colleagues evaluated whether transformation of triptan efficacy data into TG is useful. The intent of TG is to tease out the true drug effect in the face of placebo variation. To our surprise, it turned out that TG correlated more strongly with placebo response than active response. We stated that TG should not be used to compare triptans, and cautioned that migraine therapies can only be compared using well-designed head-to-head studies and not by meta-analysis.

For analysis purposes, this issue was revisited and compared two-hour headache relief reported in package inserts by study for active and placebo responses (see FIGS. 14 and 15). The theory of TG is that the active to placebo response rates should be positively correlated, better than an active-to-active correlation. The response observed with active treatment must rise and fall commensurately with the observed placebo response rate in order for TG to be a useful concept in interpretation of migraine trials.

However, perhaps unlike other applications of the TG concept, it is clear that placebo response rate is widely variable but has little or no impact on the active response rate. Data across the class of triptans show that there is large variability in placebo response between studies of a given drug, seen in FIG. 15 on the X axis. There is much less variability in the active response rate for a given active treatment between studies, seen as a relatively flat line on the Y axis in FIG. 15 across the placebo rates. There is no observable correlation between the response observed in placebo and active groups. For the studies pulled, the active:placebo R2=0.02.

Active response rates are a superior reflection of true treatment effect than TG, which appears to not be a useful concept in migraine, but as stated in 2001, well-designed head-to-head studies remain the standard for comparison. As noted earlier, it may be fair to say that the headache relief rates for the BPPSIT appear in line with other triptan therapy historically at 2 hrs, and possibly approaching historically reported response rates with injectable sumatriptan at 30 mins. This fast onset may be important to patients, particularly those with a need for rapid onset as discussed earlier. And to repeat, it is notable that this response is achieved with such a low delivered dose at 16 mg. Again, this suggests the potential for desirable safety or tolerability compared with higher dose treatment, but also underscores interesting questions about the possible contributions to efficacy of a unique activity of the device or drug in the nasal cavity.

The acute treatment of migraine requires matching individual patient need to drug and formulation. In particular, nausea and vomiting, quick time to peak intensity, and indeed the common gastroparesis of migraineurs, all call for a variety of non-oral formulations for treatment of attacks. As generic triptans become available, attempts to use them in new formulations progress. A novel BPPSIT offers an improvement, at the very least in pharmacokinetics, over conventional liquid nasal sumatriptan spray.

The Breath Powered™ device used in this study for intranasal delivery of sumatriptan uses natural nose anatomy to close the soft palate and propel the low dose powder sumatriptan high up in the nasal cavity on one side. This approach may reduce adverse events and improve efficacy.

It is certainly a worthwhile endeavor to create new delivery systems for known effective migraine medications. The clinical role for a fast acting non-oral nasal formulation will be, as noted, in those for whom tablets are bound to fail, that is, in the setting of nausea and vomiting or when the time to central sensitization, allodynia, and disabling migraine is too short for the patient to respond to a tablet, given the unpredictable and slower absorption profile of oral medications. Further studies should elucidate whether this novel system affords the predicted benefits clinically in speed of onset and effectiveness, with reduced adverse events compared with earlier non-oral formulations.

Example #8

In this study, nasal pH measurements using the Breath Powered™ delivery device of FIGS. 4(a) and (b) were analyzed. In some aspects, this data could be considered realistic and provides accessible methods to verify "device effects" in vivo. However, measurements of NO and carbon dioxide levels in the nose are not typically feasible as they require constant suction of air from the nose that would change the flow patterns.

Blinded data from head-to-head (H2H) results, using the Breath Powered™ delivery device of FIGS. 4(a) and (b) to deliver 15-16 mg of sumatriptan in powder form and an oral sumatriptan tablet (Imitrex® 100 mg Tablet or approved or generic equivalent), generally has shown a high response rate, i.e., a reduction from severe/moderate migraine to mild or none, and potential scenarios after un-blinding at 30 mins suggest one or more "device effects.".

Assuming that the highest active response rate at 30 mins for 100 mg oral sumatriptan tablets (Imitrex® 100 mg Tablet or approved or generic equivalent) (13%) is added to the highest placebo rate at 30 mins for the delivery of 15-16 mg of sumatriptan powder (31%), this sums to become 44% at 30 mins. This data suggests a response rate for the delivery of 15-16 mg of sumatriptan powder with a placebo tablet of 70% at 30 mins, which is very high. For 174 severe attacks, 95% were improved at 30 mins. Again this is a very high response rate with both treatment options (minimum 90% response).

For the blinded data, there were 1556 attacks. Of these attacks, response data at 30 mins shows: 713 Attacks were mild when treated, 669 attacks were moderate when treated, and 174 attacks were severe when treated. For the mild attacks, 117 (16.4%) went to none at 30 min. For the moderate attacks, 288 (43%) went to mild and 101 (15.1%) went to none. For the severe attacks 77 (44.3%) went to moderate, 65 (37.4%) went to mild, and 22 (12.6%) went to none. For all attacks, the 1 point improvement was 43% and pain freedom was 15.4%. For moderate/severe attacks (n=843), 57% went to mild/none and 14.6% achieved pain freedom.

Certain physiological aspects of bi-directional flow patterns were reviewed. Generally such flow patterns provide exhaled carbon dioxide exposure to nasal mucosa ranging from about 5 to about 6% carbon dioxide. In addition, pH may change locally in nasal mucosa (Djupesland 2014).

Removal of NO from upper part of the nose (Djupesland 1999) may also occur, and positive pressure may be applied to nasal mucosa (Valsalva and pain relief). Furthermore, vibrating airflow may enhance gas exchange from narrow slit-like passages and sinuses. Humming and other publications describe nasal NO, vibrating mesh, and pulsed nebulizers.

There are several possible explanations for the potential device effects described above. Evidence of such effects comes from high placebo rates observed in Phase 2 and Phase 3 trails even at early time points. The blinded H2H data also suggests additional "device effects."

One hypothesis is that bi-directional delivery of exhaled air with about 5-6% carbon dioxide offers similar exposure of carbon dioxide to the nasal mucosa as low flow delivery of 100% carbon dioxide at very low flow rates or 15-45% carbon dioxide at low flows (see Shusterman, 2003).

In a Phase 2 migraine trial (Spierings, 2008—Capnia), carbon dioxide was passively delivered at 10 ml/sec for 90 s (900 mL) or 5×15 (1050 mL) with 45 s pauses and up to seven dosing cycles during first 2 hrs with minimum 3.5 mins resting for migraine. This was about equal to 10 ml of carbon dioxide per second. Considerable dilution of the carbon dioxide is expected due to open nose and possible nasal inhalations or exhalation during delivery.

In a Phase 2 acute rhinitis (AR) trial (Casale, 2008—Capnia), carbon dioxide was passively delivered intranasally twice for 60 s at a rate of 10 mL/s, for a total dose of approximately 1200 mL. The doses were separated by an interval of less than 5 mins and were administered to alternate nostrils. The subjects avoided excessive inhalation of the gas by breathing through the mouth, allowing the gas to flow in one nostril, pass through the nose and sinus cavities, and pass out through the other nostril. Again, flow rate was 10 ml carbon dioxide per second. Considerable dilution of the carbon dioxide is expected due to open nose and possible nasal inhalation or exhalation during delivery.

The Shusterman, 2003 article also describes, synchronized with inhalation, the delivery of carbon dioxide at 5 L/min 15%×3 s. This equates to 250 mL×0.15, giving 37.5 ml carbon dioxide, or 12.5 ml per second. By comparison, the Breath Powered™ delivery device of FIGS. 4(a) and (b) (Djupesland 2014), provides 30 L/min for 3 s of 5% carbon dioxide, giving 500 mL/s with about 5-6% carbon dioxide, in turning giving 25-30 mL/s or 75-90 mL in 3 s of carbon dioxide.

Carbon dioxide has shown effects in migraine allergic rhinitis, and carbon dioxide is believed to act on local, for example, trigeminal, nerve structures via reduced local pH in mucosa, triggering intercellular events desensitizing the nerve. Also, carbon dioxide delivered to nose can cause pH change in nasal mucosa (Shusterman, 2003).

Carbon dioxide works in migraine and AR at least in part by changing pH. A recent publication describes the release of CGRP from the trigeminal sensory fibers upon irritant stimuli, such as carbon dioxide, which inhibits the odor response of olfactory receptor neurons. Papers by Vause and Spierings state that "[r]esults from this study provide the first evidence of a unique regulatory mechanism by which carbon dioxide inhibits sensory nerve activation, and subsequent neuropeptide release. Furthermore, the observed inhibitory effect of carbon dioxide on CGRP secretion likely involves modulation of calcium channel activity and changes in intracellular pH.".

It appears that it is the intracellular pH changes that mediate the effects and that the extracellular pH changes to a large extent are buffered by nasal mucus secretion. In a recent study as well as the studies by Shusterman, 2003 small changes in the nasal pH have been measured by probes inserted into the nasal passage with a diameter between 1.5 and 2 mm. These probes have been used to measure pH in the esophagus and ventricle, and can be coupled directly to software that provides detailed curves (see example below).

From these studies, it appears that a carbon dioxide concentration >15 vol % is required to see a change in the nasal pH. However, as will be discussed in more detail hereinbelow, the present study has established that using the Breath Powered™ delivery device, a change in nasal pH can be achieved at carbon dioxide concentrations of 5-6 vol %.

Previous literature describes rats having hypersensitive olfactory receptors that can sense or smell carbon dioxide concentrations of the order of 1-3% and even lower. This high-sensitivity mode of carbon dioxide detection depends on the activity of carbonic anhydrase which catalyzes the synthesis of carbonic acid et al. The resulting acidification induces activity in a small subset of olfactory receptor neurons which are located in the most dorsal recesses of the olfactory epithelium.

In humans, there is no such high-sensitive carbon dioxide detection, and carbon dioxide has no odor for us. At higher carbon dioxide concentrations, however, trigeminal fibers are activated, again through acidification. Importantly, the protons that induce trigeminal activity are not those released in the olfactory mucus or in the interstitial fluid, but those released within the axoplasm of the trigeminal fibers. Studies of TRPA1-channel gating in trigeminal ganglion neurons have recently revealed that the channels are opened by intracellular acidification (Wang et al., 2010).

As carbon dioxide can readily diffuse across plasma membranes, the carbonic anhydrase reaction inside the sensory endings can trigger a drop in intra-fiber pH. The precise extent of this intracellular acidification has not to date been measured, and the intra-fiber concentration of carbonic anhydrases is not known. However, considering the small accessible volume within the fibers, acidification would be expected to be more pronounced within the fibers than in the surrounding fluid with its much larger volume.

In human subjects, Shusterman, 2003 measured the acidification of nasal mucosal pH with extracellular pH electrodes during carbon dioxide stimuli similar to the ones used in the present study (5 L/min, 3 s duration, 20% carbon dioxide). The extracellular pH decreased from basal levels of ~7.4 by only 0.05-0.1 pH units, and the effect of carbon dioxide is during each carbon dioxide pulse. These minute decrements in extracellular pH reflect efficient pH buffering of the extracellular medium. The advantage of carbon dioxide detection by intracellular acidification is that larger pH changes can be triggered by carbon dioxide inside the axoplasm. With respect to the extracellular medium, the trigeminal fibers appear not to act as pH electrodes but rather as carbon dioxide electrodes, independent of volume and pH buffer capacity of the surrounding fluid.

Even if humans do not have the high-sensitivity to carbon dioxide, recent study suggests that humans may distinguish carbon dioxide levels of about 5-6% $CO_2$. Moreover, the nasal mucosa may be more sensitive in the anterior part of the nose.

One or more factors may affect the response data described above that result from using the Breath Powered™ delivery devices of FIGS. 2(a) and (b), FIGS. 3(a) and (b) and FIGS. 4(a) and (b). One hypothesis is that by utilizing the Breath Powered™ delivery technique, the particular air flow and pressure characteristics achieved offer separate advantages which may at least in part explain the high placebo effects observed in previous studies and the high response at 30 mins when a placebo Breath Powered™ delivery device is combined with an oral sumatriptan tablet. We predict that one or more factors may have an impact and these factors are likely to include gas pressure, removing NO from the nose, or exposure to exhaled carbon dioxide. Of these factors, the carbon dioxide may have the most significant impact.

As noted above, carbon dioxide is known to have an effect on migraine and in allergic rhinitis. It is likely that is mediated through small changes in the local pH. A prior study shows that exposure of 5 L/min carbon dioxide in concentrations of 15% and 45% both create dips in mucosal pH of 0.1-0.2 pH units. The study speculated that such small pH changes may have an impact on the trigeminal nerve and change trigeminal sensitivity and conductivity. Other studies have suggested that it may have an impact on the release of CGRP, and thus on migraine pain.

In the present study, measuring pH in a nose when using the Breath Powered™ delivery devices of FIGS. 3(a) and (b) and FIGS. 4(a) and (b), but without delivery of active substance, yielded unexpected results. Exhaling through these Breath Powered™ devices without any release of substance caused a repeated and generally reproducible (subject to small, unavoidable variation in the sensor position) dip in pH by 0.1-0.2 pH units. This data is similar to that observed with a 3 s burst of 15% and 45% carbon dioxide. In this study, the sensor was placed both at the floor of the nose and close to the roof of the nose. In many instances, larger "dips" are observed when the sensor is placed towards the roof of the nose compared to the floor.

As hypothesized above, and based in part on previous measurements of NO, with the very low flow rates of carbon dioxide, it takes time to achieve and increase carbon dioxide concentration in the upper part of the nose when carbon dioxide is delivered to the floor of the nose. Even with high concentrations of about 45% to about 100% as employed in previous studies, it may take more time than the 10 s pulses to achieve a concentration of approximately 6% which is achieved instantly with use of the Breath Powered™ devices as described above. This could explain the "device effects" observed when using these Breath Powered™ devices.

It is noteworthy that we are able to detect dips in pH in direct response to use of the Breath Powered™ devices as described above. This data provides a scientific and logical explanation for the high placebo effects and the very high response rates.

Data described herein provides support to the hypothesis of device effects. Measurements with both the Breath Powered™ device of FIGS. 3(a) and (b) for the delivery of liquid and the Breath Powered™ device of FIGS. 4(a) and (b) for the delivery of powder result in similar data. Thus, it is the underlying Bi-Directional™ methodology, rather that the specific device, that appears to have a significant effect. It is noteworthy that carbon dioxide also has an effect in allergic rhinitis.

In this study, nasal pH measurements were made using a Digitrapper pH 1.6 mm pH sensor and AccuView software, as provided by WinMed in Norway. In embodiments one or more probes P are located as shown generally in FIG. 16, and may be located in either nasal passage.

Data showing pH as a function of exhalation flow, with a sensor probe P located on same side towards nasal roof, using the Breath Powered™ device of FIGS. 4(a) and (b), is shown in FIG. 17. Data showing pH as a function of exhalation flow using the Breath Powered™ device of FIGS. 3(a) and (b) and the Breath Powered™ device of FIGS. 4(a)

and (b) are shown in FIG. 18, with a pH sensor placed towards a roof of the nose approximately 4-5 cm from a nostril opening. FIG. 19 illustrates data showing pH as a function of exhalation flow associated with the Breath Powered™ delivery device of FIGS. 4(a) and (b), with a sensor located about 4-5 cm into the nose at the floor and middle part of the nose. FIG. 20 illustrates additional data showing pH as a function of exhalation flow associated with the Breath Powered™ delivery device of FIGS. 4(a) and (b), again with a sensor located about 4-5 cm into the nose at the floor and middle part of the nose.

Shusterman, 2003 delivered 3 s pulses of regular air (0%) and carbon dioxide at 15% and 45% to the nose. A pH sensor was placed along the floor of the nose. Sampling frequency was 10 per second (10 Hz). Data from this study is shown in FIG. 21.

By way of comparison, the present study compared oral breathing, calm nasal breathing and calm nasal breathing before delivery with the Breath Powered™ delivery devices of FIGS. 3(a) and (b) and FIGS. 4(a) and (b), with a sensor being located at about 4-5 cm into right nostril and the device inserted into left nostril. Data associated with the method is shown in FIG. 22.

In summary, the Breath Powered™ delivery devices offer greater physiologic activity and efficacy as compared to the delivery of 100% carbon dioxide delivered in trials showing conical effects in migraine and allergic rhinitis (Capnia—Casale 2008 and Spierings 2008). The Breath Powered™ delivery devices also show similar reductions in pH levels in direct response to exhalation through the devices, as compared to both 15% and 45% carbon dioxide delivered in 3 s pulses 1 min apart. These results suggest that the Breath Powered™ devices can produce similar carbon dioxide exposures to the nasal mucosa as delivery of 100% used previously in trials and shown to have effects in migraine and perennial allergic rhinitis. This effect associated with carbon dioxide when using the Breath Powered™ devices may, in combination with one or more other factors associated with use of the Breath Powered™ devices, including positive air pressure, a high flow rate and changed flow pattern, improved air flow penetrating the nasal airway, vibratory effect in operating the devices and removal of nitric oxide, can cause stimulatory or mediating effects on the trigeminal nerve and on mast cells.

Example #9

A Phase 2 trial with low-dose sumatriptan powder using a closed-palate Breath Powered™ device produced headache relief approaching levels previously reported by injection, but without triptan effects.

This additional study was undertaken to evaluate the efficacy and safety of this delivery regime as compared to placebo in patients with moderate-to-severe acute migraine headache.

This study was a Phase 3, multicenter, randomized, double-blind, placebo-controlled, single-dose, parallel-group study, which was conducted in patients who had experienced between 1-8 migraines/month in the 12 months prior to screening. Each patient treated a single migraine headache of moderate or severe intensity with two doses (one to each nostril) from capsules containing 11 mg sumatriptan powder (the capsules together providing a total dose of 22 mg) using the Breath Powered™ device of FIGS. 4(a) and (b) or a matching, counterpart device loaded with placebo (placebo device). In this study, the nominal dose in each capsule was 11 mg of the free base, which yielded an average delivered dose of 7.5 mg, giving a total average delivered dose of 15 mg from two capsules.

The following efficacy outcomes were measured:
Headache response (pain rated as mild or none) at 120 min (primary), and multiple time points up to 120 mins,
Completely pain-free (freedom from headache pain) at multiple time points up to 120 mins,
Time to meaningful relief (patient reported interpretation of headache pain response),
Clinical disability and migraine-associated symptoms (photophobia, phonophobia, nausea and vomiting),
Rescue medication use, and
Sustained response/sustained pain-free (headache response/completely pain-free at 120 min and no recurrence or use of rescue medication up to 24 and 48 h post-dose).

In total, 212 patients (mean age 42; 85% female) received treatment (108 sumatriptan powder; 104 placebo). Patient demographics and baseline characteristics are shown in FIG. 23.

Headache response at 120 min (primary outcome) was 68% vs. 45% ($P<0.01$). Headache response curves diverged early, reaching statistical significance at 30 min (42% vs. 27%; $P<0.05$). In general, the present delivery regime was statistically superior to placebo for completed relief and sustained response and remained at 24 and 48 hrs. Reductions were also seen in disability and migraine associated symptoms.

Results are shown in FIG. 25. Generally, complete pain free (120 mins) was 37% vs. 17% ($P<0.01$) and meaningful relief (120 mins) was 70% vs. 45% ($P<0.001$). For the sustained response, at 24 hrs, it was 44% vs. 24% ($P<0.01$) and at 48 hrs, it was 34% vs. 20% ($P=0.01$). For sustained pain free, at 24 hrs, it was 28% vs. 12% ($P=0.005$), and at 48 hrs, it was 20% vs. 9% ($P=0.02$). In addition, reductions in nausea, phonophobia, and photophobia were reported in both groups (not significant vs. placebo). Significantly more patients using placebo (52%) than the present delivery regime (37%; $P=0.02$) required rescue medication.

For the primary endpoint, 68% of patients using the present delivery regime reported headache relief at 120 min post-dose vs. 45% using placebo device ($P<0.01$; FIG. 26). Headache relief with the present delivery regime was achieved early, reaching statistical significance compared with placebo at 30 min (42% vs. 27%, $P<0.05$; FIG. 26). Headache relief is determined as a reduction from severe (Grade 3) or moderate (Grade 2) headache pain to mild (Grade 1) headache pain or no headache pain (Grade 0) on the International Classification of Headache Disorders ($2^{nd}$ Edition) criteria.

Significantly fewer patients using the present delivery regime required rescue medication compared with placebo device (37% vs. 52%, $P<0.05$).

In addition, more patients using the present delivery regime experienced maintained pain relief at 24 and 48 h vs. placebo device (FIG. 26). And, more patients using the present delivery regime (28%) maintained pain freedom at 24 h without rescue medication vs. 12% using placebo ($P<0.01$). Maintained pain relief at 24 or 48 h were calculated for those patients with headache relief and complete pain relief, respectively, at 120 min, who had no recurrence of headache and required no rescue medication for the 2-24 h and 2-48 h timeframes.

Consistent with results for the headache relief measure, significantly more patients using the present delivery regime experienced meaningful relief (FIG. 27—showing a proportion of patients with meaningful relief a following treatment with the present delivery regime or placebo device at 120 min post-dose (FAS)), and complete pain relief (FIG. 28—proportion of patients who achieved pain freedom at 120 min endpoint (FAS)) at the 120 min endpoint compared with placebo. Meaningful relief is a patient reported interpretation. Pain freedom is freedom from headache pain as determined by a reduction from severe (Grade 3) or moderate (Grade 2) headache pain to none (Grade 0).

Clinical disability score was significantly improved in patients treated with the present delivery regime compared with placebo between 45 and 120 min inclusive (P<0.05). The incidence of migraine-associated symptoms was substantially reduced at the 120 min endpoint (the present delivery regime vs. placebo device: nausea 19% vs. 21%, vomiting 2% vs. 0%, photophobia 48% vs. 60%, phonophobia 32% vs. 44%). These reductions did not reach significance between groups.

There were few systemic adverse effects (AEs) and none reported in more than one patient. Certain AEs known as triptan effects are associated with formulations and doses that produce high plasma drug concentrations. There were also minimal triptan sensations. Specifically, there were no chest pressure/tightness, and only one patient reported mild, transient paraesthesias. The most common (>5%) AEs reported were product taste (22%), nasal discomfort (13%), and rhinitis (6%).

Unlike traditional nasal sprays, the present delivery regime uses a novel Breath Powered™ device to deliver powdered sumatriptan deep within nasal structures where it can be rapidly absorbed. This deep region is also extensively innervated by the trigeminal and olfactory nerves, theoretically offering potential for direct effects or nose-to-brain transport. The Breath Powered™ device delivers carbon dioxide locally and removes nitric oxide (NO), in combination with a positive air pressure and vibration from rattling of the capsule. This effect may have contributed to both the placebo response seen in this study. The high placebo response may also be related to neurochemical effects of carbon dioxide delivery and/or removal of NO at the trigeminal nerve endings within the nasal cavity. NO is known to stimulate release of CGRP from the trigeminal neurons, a key mediator in the pathophysiology of migraine, whereas carbon dioxide inhibits CGRP release and may be beneficial in migraine modulation.

In conclusion, treatment with the present delivery regime produced fast and sustained migraine relief compared with the counterpart placebo device with minimal triptan sensations, despite the high response to the placebo device itself. This data is consistent with results from an earlier Phase 2 trial and suggest that the present delivery regime can offer an important therapeutic and practical option for acute migraine treatment.

Example #10

Example #10 follows Example #9, and represents an extension of that study, with the obtained data unblinded.

This study is a multicenter, double-dummy, active-oral-comparator, crossover study with two up-to-12-week double-blind periods, as represented in FIG. 29.

The patients were 18-65 years old with a diagnosis of migraine with or without aura according to the International Classification of Headache Disorders ($2^{nd}$ Edition) criteria for at least one year prior to screening and who experienced 2-8 migraine attacks/month for the past twelve months. A total of 275 migraineurs were randomized; and 185 (67.3%) treated 1-5 migraines in both periods, comprising the Full Analysis Set (FAS). A total of 1531 migraines were assessed during the study for patients in the FAS. On average, patients were 40.1 years of age, female (85%), and had 4.9 migraine attacks per month at baseline. The demographics of the patient sample are represented in FIG. 30.

The patients were randomized 1:1 to:
1) The Breath Powered™ administration device of FIGS. 4(a) and (b) (using two capsules each containing 11 mg of sumatriptan powder, and each delivering an average of 8 mg, giving a total nominal dose of 22 mg sumatriptan powder and an average total delivered dose of 16 mg sumatriptan powder) plus oral placebo tablet; and
2) An identical placebo device (but containing lactose powder) plus 100 mg oral sumatriptan tablet (Imitrex® 100 mg Tablet or approved or generic equivalent).

In each period (up to 12 weeks duration) of the double-blind phase, patients treated up to 5 qualifying migraines with study medication (device plus oral tablet). A qualifying migraine met International Headache Classification of Headache Disorders ($2^{nd}$ Edition) criteria of at least mild (Grade 1) intensity, and treatment was administered within 1 hr of onset of a qualifying migraine.

Immediately before dosing and at 10, 15, 30, 45, 60, 90 and 120 mins, and 24 and 48 hrs post-dose, patients recorded in an electronic diary the following:
Headache Severity score (pain intensity of 0=none, 1=mild, 2=moderate, 3=severe)
Clinical Disability score (performance of daily activities of 0=no disability, 1=mildly impaired, 2=moderately impaired, 3=severely impaired)
Presence/absence of nausea, phonophobia, photophobia, or vomiting After 120 mins, patients recorded the presence/absence and severity of atypical sensations (consisting of tingling, warm/hot sensation, burning sensation, feeling of heaviness, pressure, feeling of tightness, including tightness in the head, numbness and feeling strange).

A second dose of study drug could have been taken after all diary assessments were completed for the 120 min timepoint up to 24 hrs after the first study drug dose if there was no relief, the headache worsened, or the headache recurred. Headache severity assessments were also taken at 24 and 48 hrs.

After the second dose, rescue medication could have been taken if there was no relief, the headache worsened, or if the headache recurred at 120 mins after the second dose of the study drug.

The primary endpoint, SPID-30, assessed summed pain intensity differences (SPID) utilizing all Headache Severity scores on the International Classification of Headache Disorders ($2^{nd}$ Edition) criteria from dosing through 30 mins.

Data were analyzed by ANCOVA (treatment, period, and treatment sequence as fixed effects; subject as a random effect) using last observation carried forward (LOCF).

Secondary endpoints included an evaluation of headache relief, pain reduction, and pain freedom at each timepoint.

As illustrated in FIGS. 31 and 32, the primary endpoint (SPID-30) showed that significantly greater pain relief was achieved with intranasal delivery of sumatriptan powder using the Breath Powered™ device of FIGS. 4(a) and (b) and compared to the oral sumatriptan tablet over the initial 30 min post-dose (LS mean of 10.80 vs. 7.41, P<0.001).

As illustrated in FIGS. 33 and 34, starting at 15 min and through 90 min, statistically greater post dose rates of pain relief (P<0.05) were achieved with intranasal delivery of sumatriptan powder using the Breath Powered™ device of FIGS. 4(a) and (b). At 30 min, pain relief with intranasal delivery of sumatriptan powder using the Breath Powered™ device of FIGS. 4(*a*) and (*b*) was achieved in 54% of attacks vs 39% (P<0.001) with the oral tablet in combination with the placebo device for severe or moderate attacks. This rate of headache relief even exceeds the headache relief for 6 mg subcutaneously administered sumatriptan (Imitrex® 6 mg SC or approved or generic equivalent) at time intervals of 15, 30, 60 and 120 min, being 10, 45, 71 and 78%. Headache relief is determined as a reduction from severe (Grade 3) or moderate (Grade 2) headache pain to mild headache pain (Grade 1) or no headache pain (Grade 0).

In addition, the present delivery regime provides for a similar maintained headache relief at 24 and 48 h vs. the placebo device. This is particularly significant as equivalent maintenance of headache relief is obtained using a delivered dose of about 16 mg, as compared to 100 mg from the tablet when using the placebo device.

As illustrated in FIGS. 35 and 36, starting at 15 min and through 90 min, statistically greater post dose rates of pain freedom (P<0.01) were achieved with intranasal delivery of sumatriptan powder using the Breath Powered™ device. At 30 min, pain freedom with intranasal delivery of sumatriptan powder using the Breath Powered™ device was achieved in 18% of attacks vs 11% (P<0.001) with the oral sumatriptan tablet. Pain freedom is freedom from headache pain as determined by a reduction from severe (Grade 3), moderate (Grade 2) or mild (Grade 1) headache pain to no headache pain (Grade 0).

In addition, intranasal delivery of sumatriptan powder using the Breath Powered™ device had shorter times both to meaningful pain relief, with a $25^{th}$ percentile (95% CI) of 20 mins (16-30 min) vs 31 mins (95% CI not evaluable) and a median of 45 min (32-46 min) vs 49 min (46-61 min), and to pain freedom, with a $25^{th}$ percentile (95% CI) of 46 mins (95% CI not evaluable) vs 60 min (46-91 min) and a median of 91 min (95% CI not evaluable) vs 121 min (91-121 min).

Figure 4B:
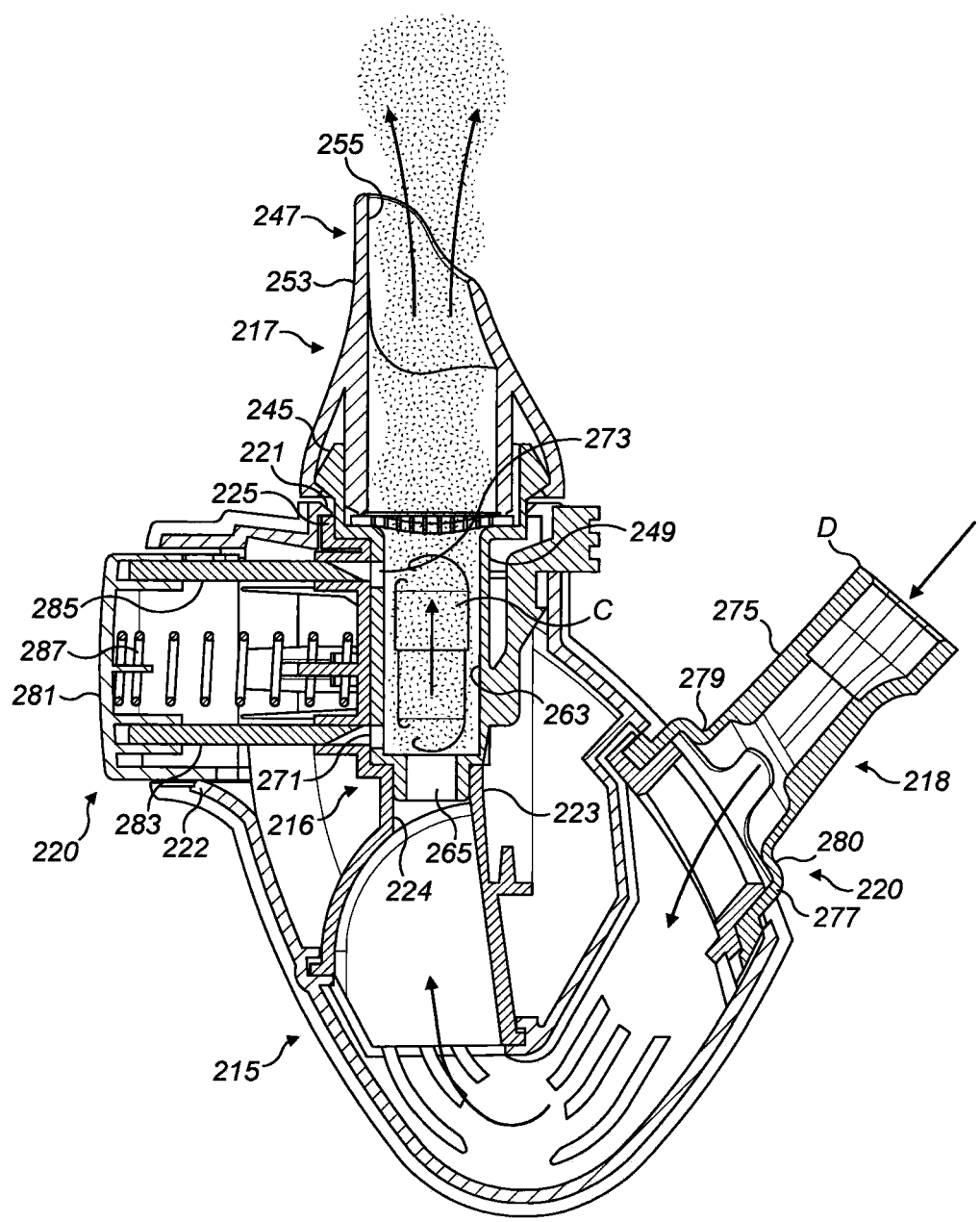

Also, as illustrated in FIG. 36, intranasal delivery of sumatriptan powder using the Breath Powered™ device of FIGS. 4(*a*) and (*b*) exhibits pain reduction in a significantly greater number of attacks. At 30 min, pain reduction with intranasal delivery of sumatriptan powder using the Breath Powered™ device of FIGS. 4(*a*) and (*b*) is 49% vs 35% (P<0.001). Pain reduction is a decrease in pain intensity of at least one point in patients with severe (Grade 3), moderate (Grade 2) or mild (Grade 1) headache pain at baseline.

Pain relief and pain freedom were comparable for intranasal delivery of sumatriptan powder using the Breath Powered™ device of FIGS. 4(*a*) and (*b*) and the oral sumatriptan tablet at 120 min and sustained through 24 and 48 h, as illustrated in FIG. 37.

Less than 2% of patients of treated patients (n=262, safety set) experienced an adverse event (AE) leading to discontinuation, and no serious AEs were reported.

Nasal discomfort and abnormal product taste were reported more commonly with administration of sumatriptan using the Breath-Powered™ device of FIGS. 4(*a*) and (*b*) and placebo tablet as compared with the 100 mg sumatriptan tablet and the placebo device (16% vs. 1% and 26% vs. 4%), but these were deemed mild in nearly 90% of cases and led to only one study discontinuation.

In addition, atypical triptan sensations, consisting of tingling, warm/hot sensation, burning sensation, feeling of heaviness, pressure, feeling of tightness, including tightness in the head, numbness and feeling strange were significantly lower among patients treated with sumatriptan powder using the Breath Powered™ device of FIGS. 4(*a*) and (*b*) (2% vs 5%, P=0.02), as illustrated in FIG. 38. Although atypical sensations were not specifically measured in the Phase 1 pharmacokinetic cross-over trial of patients (n=20) treated with sumatriptan powder using the Breath Powered™ device of FIGS. 2(*a*) and (*b*) and other sumatriptan dosage forms, rates of treatment-related flushing (the AE occurring with highest incidence) were 20% for Imitrex® 6 mg SC, but did not occur for patients treated with sumatriptan powder using the Breath Powered™ device. As compared to Imitrex® 6 mg SC, the rates are notably lower, being, for example, 14% for tingling. This low level of atypical triptan sensations in patients treated with sumatriptan powder using the Breath Powered™ device of FIGS. 4(*a*) and (*b*) is clinically relevant to patients and can be a potential advantage of intranasal delivery using the Breath Powered™ device.

It will also be noted that the rate of pain relief for the 100 mg oral sumatriptan tablet and placebo device far exceeds the labelled pain relief for the 100 mg oral sumatriptan tablet when taken conventionally without use of a nasal administration device (Imitrex® 100 mg Tablet or approved or generic equivalent) at time intervals of 30, 60 and 120 min, being 39, 63 and 77 vs 12, 35 and 60%.

Example #11

In the examples and discussion provided above, carbon dioxide has been described as providing a mechanism to provide and/or enhance a therapeutic or pharmacokinetic effect and/or adjust the pH of a region within the nasal passage. Carbon dioxide may react within the nasal passage to lower pH. As described above, the concentration of delivered carbon dioxide can range from about 5 to about 6% vol/vol. In other aspects, a therapeutic amount of carbon dioxide can include more than about 1% vol/vol carbon dioxide and less than about 10% vol/vol carbon dioxide.

A gas or fluid other than carbon dioxide could be used to provide pH adjustment, such as, for example, raising pH. It is also contemplated that one or more solid materials could be used to adjust pH within a nasal passage, with or without carbon dioxide or another gas or fluid. For example, fine particulate matter could be used to adjust the pH of an extracellular environment about tissue within the nasal passage.

In some embodiments, a pH adjusting material could include an acidic or a basic gas or buffer solution. The pH adjusting material could also form part of a formulation contained with or separate from a therapeutic agent. The pH adjusting material may adjust the pH by a known amount. The known amount may be determined based on the requirements of an individual or group of individuals, a therapeutic agent, group of agents, or expected behavior of one or more agents. The known amount may range from about 0.01 to about 0.5 pH units, or about 0.1 to about 0.2 pH units.

Various mechanisms could be used to aerosolize or otherwise create an air flow containing the pH adjusting material. For example, a powder of pH adjusting material could be combined with the therapeutic agent in a capsule or blister pack. In another embodiment, one or more separate capsules or blister packs could be located adjacent to, upstream, or downstream of the therapeutic agent to provide pH adjustment prior to, simultaneously, or after the therapeutic agent is airborne. Mechanical, electrical, or chemical vibration mechanisms could also be used to release the pH adjusting material.

Example #12

The purpose of this study was to investigate the treatment of patients with chronic rhinosinusitis (CRS) with nasal polyps using f In a three-month placebo controlled study in 109 patients with chronic rhinosinusitis (CRS) with nasal polyps, delivery of fluticasone (400 μg b.i.d.) with the Breath Powered™ delivery device of FIGS. 3(a) and (b) was reported to be well tolerated and to produce a large magnitude of reduction in both symptoms and the overall polyp score.

Particularly notable relative to expectations with standard nasal spray delivery, complete elimination of the polyps in close to 20% of the subjects was reported after three months. The proportion of subjects with improvement in summed polyp score was significantly higher with the present delivery regime as compared with placebo at 4, 8, and 12 weeks (22% vs. 7%, p=0.011, 43% vs. 7%, p<0.001, 57% vs. 9%, p<0.001).

Despite relatively lower baseline polyp scores after 12 weeks, the summed polyp score was significantly reduced from 2.8 to 1.8 in the active treatment group, whereas a minor increase in polyp score was seen in the placebo group (−0.98 vs. +0.23, p<0.001).

Peak nasal inspiratory flow (PNIF) increased progressively during treatment with the present delivery regime (p<0.001). Combined symptom score, nasal blockage, discomfort, rhinitis symptoms, and sense of smell were all significantly improved.

The highly significant progressive treatment effect of the present delivery regime was observed regardless of baseline polyp score. Previous sinus surgery had no impact on the efficacy. Coupled with the complete removal of polyps in many patients with small polyps, this suggests that improved deposition to target sites achieved with the Breath Powered™ delivery device of this study may translate into true clinical benefits and possibly reduced need for surgery.

Example #13

Using the same drug-device combination product as Example #12, a small placebo controlled study (N=20) was performed in patients with post-surgical recalcitrant CRS without polyps, producing clinically significant improvements on both objective measures and subjective symptoms.

Endoscopy score for edema showed a significant and progressive improvement [12 weeks (median scores): the present delivery regime −4.0, vs. placebo −1.0, p=0.015].

Peak nasal inspiratory flow (PNIF) increased significantly during treatment with the present delivery regime as compared to placebo (4 weeks: p=0.006; 8 weeks: p=0.03). After 12 weeks, MRI scores in the group receiving the present delivery regime improved against baseline (p=0.039), and a non-significant trend was seen vs. placebo.

The nasal RSOM-31 subscale was also significantly improved with treatment using the present delivery regime (4 weeks: p=0.009, 8 weeks: p=0.016, 12 weeks: NS). Sense of smell, nasal discomfort, and combined score were all significantly improved (p<0.05). Notably, this is a condition marked by many recent negative placebo-controlled trials. This context, in addition to comparison with historical data in similar patient samples, again suggests that use of the Breath Powered™ delivery device is capable of producing superior deep nasal deposition in clinical practice (improved targeting of the middle meatus in this case) which can translate into improved clinical response.

As described above, the present disclosure provides a method of treating a patient. The treatment can include one or more steps, wherein a first step can include administering a therapeutic agent. A second step can include delivering carbon dioxide or a pH adjusting material to one or more regions of the nasal passage, as described above. The order of the steps can be interchanged, so the second step occurs before the first. It is also contemplated that both steps, or more, may occur simultaneously.

As discussed above, it is postulated that the effect of carbon dioxide, particularly in terms of pH and the NO concentration, and increased pressure produced by the device within the nasal cavity on the trigeminal nerve and sphenopalatine ganglion results in a higher overall response rate, especially in the oral tablet group at early time-points.

Finally, it will be understood that the present disclosure has been described in various embodiments and can be modified in many different ways without departing from the scope of the disclosure as defined by the appended claims.

For example, the present disclosure has been exemplified in relation to sumatriptan, but it will be understood that the present disclosure has application to many other substances, including other triptans, such as risatriptan, naratriptan, eletriptan, frovatriptan and zolmitriptan, and other analgesics, such as ergotamines, including dihydroergotamine mesylate, ergonovine maleate and ergotamine tartarate with caffeine, fentanyl, oxycondone, hydromorphone, morphine, codeine, ketobbemidone, cocaine and opiods in general.

The present disclosure also has application to benzodiazepines, such as midazolam.

The present disclosure further has application in relation to non-steroidal anti-inflammatory drugs (NSAIDs), for example, aspirin, ibuprofen, naproxen, indomethacin, diclofenac and ketoprofen.

From the results of the referenced studies, it is apparent that the present disclosure has application in relation to the delivery of proteins and peptides, and especially hormones and derivatives and analogs thereof, in particular having a molecular weight greater than 1000 g/mol, which typically have a very low oral bio-availability, often less than 1%. Particular examples include insulin, including its analogues and derivatives, desmopressin and calcitonin. Other examples include growth hormone and its analogues and derivatives, oxytocin and its analogues and derivatives and orexin (hypocretin) and its analogues and derivatives, including Orexin-A (Hypocretin-1) and its analogues and derivatives.

The present disclosure yet still further has application in relation to powder vaccines, immunomodulators and immunostimulators.

In summary, the present disclosure has application in relation to the following broad definitions of molecules.

Small molecules (<1000) with relatively fast nasal absorption and high nasal BA, such as fentanyl, midazolam and oxycodone. The present disclosure suggests far more rapid CNS effects than compared to the prior art nasal administration systems, which could be because of differences between arterial and venous concentrations, where arterial absorption is between about 25% and 50% greater than venous absorption, possible "counter current" transport to the sinus cavernous and the carotid artery, which must pass the BBB, which has been shown to be about 25% greater in animal studies, and possible direct N2B transport along the olfactory and trigeminal nerves (Einer-Jensen, N et al, Pharmacol. Toxicol., 87(6), 2000, pages 276 to 278, Einer-Jensen, N et al, Exp. Brain Res., 130(2), 2000, pages 216 to 220, and Dale, O et al, Intranasal Midazolam: a comparison of two delivery devices in human volunteers, J. Pharmacy and Pharmacology, 58, 2006, pages 1311 to 1318). N2B transport and clinical effects via the trigeminal nerves are not, however, necessarily reflected in the traditional PK profile.

Small and medium sized molecules with relatively poor BA, such as sumatriptan and zolmitriptan. For the sumatriptan powder of the present disclosure, sumatriptan passes the BBB relatively poorly, but animal studies suggest that sumatriptan can be transported directly to the brain by direct N2B mechanisms (Gladstone, J P, Newer formulations of triptans: Advances in migraine treatment, Drugs, 63, 2003, pages 2285 to 2305). The present disclosure provides for increased absorption, which is particularly relevant where rapid absorption and a fast onset of action are desirable. The present disclosure suggests more rapid CNS effects, which could be because of possible direct N2B uptake, possible "counter current" transport to the sinus cavernous and the carotid artery, where the molecule is able to pass the BBB, and possible direct N2B transport along the olfactory and trigeminal nerves.

Larger molecules (>1000), including peptides and proteins, which have low nasal BA, typically between about 3 and 15%, and very poor oral BA, typically less than 1%, because of degradation in the GI tract. The present disclosure, in providing a powder formulation, is particularly suited to the delivery of peptides and proteins, where the powder can provide for improved nasal absorption, but also can have improved stability. For these substances, it is postulated that there may be a dedicated transport mechanism along the olfactory and trigeminal nerves directly to the cerebral structures, which is not via the CSF. As such, measurements from the CSF may not show the presence of active substance, but a substantial effect may be present in the brain and exert clinical effects, as exemplified in a recent study (Thorne, R G et al, Delivery of insulin-like growth factor-I to the rat brain and spinal cord along olfactory and trigeminal pathways following intranasal administration, Neuroscience, 127(2), 2004, pages 481 to 496).

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the disclosure is not to be considered as limited by the foregoing description.

All references cited herein are incorporated by reference in their entirety. To the extent publications and patents or patent applications incorporated by reference contradict the disclosure contained herein, the specification will supersede any contradictory material.

The term "placebo" is used herein to designate a comparative administration, which may or may not include administration of a pharmaceutical agent. However, such "placebo" treatments may be therapeutic in and of themselves due to, for example, nasal delivery of carbon dioxide, without or without the further administration of a pharmaceutical agent.

What is claimed is:

1. A method of treating nasal polyps in a patient comprising:
    placing a nosepiece into a first nostril of the patient;
    placing a mouthpiece into a mouth of the patient, the mouthpiece being fluidly connected to the nosepiece, wherein exhalation by the patient into the mouthpiece and out of the nosepiece produces a bi-directional fluid flow of exhalation air into a first nasal passageway of the patient and out of a second nasal passageway of the patient;
    administering fluticasone during exhalation by the patient through the nosepiece;
    delivering carbon dioxide during exhalation by the patient through the nosepiece, to a location at an upper posterior region of the first nasal passageway of the patient; and
    reducing a pH at the location at the upper posterior region of the first nasal passageway of the patient by an amount ranging from about 0.1 pH units to about 0.2 pH units by controlling the fluid flow to deliver the carbon dioxide at a concentration of from about 5% vol/vol to about 6% vol/vol carbon dioxide and at a fluid flow rate of at least 20 L/min for a duration of from about 2 seconds to about 3 seconds, wherein the carbon dioxide is delivered before or at the same time as the fluticasone.

2. The method of claim 1, wherein the fluticasone is fluticasone propionate.

3. The method of claim 1, wherein the fluticasone is administered as a liquid aerosol.

4. The method of claim 1, wherein the fluticasone is administered in an amount of about 400 μg b.i.d.

5. The method of claim 1, wherein the fluticasone is administered in an amount of 100 μg to 400 μg b.i.d.

6. The method of claim 1, wherein the fluticasone is administered in an amount of at least 200 μg daily.

7. The method of claim 1, wherein the fluticasone is administered in an amount of at least 400 μg daily.

8. The method of claim 1, wherein the fluticasone is administered in an amount of at least 200 μg daily delivered in two doses.

9. The method of claim 1, wherein the fluticasone is administered in an amount of at least 400 μg daily delivered in two doses.

10. The method of claim 1, wherein the fluticasone is fluticasone propionate administered as a liquid aerosol in an amount of 100 μg to 400 μg b.i.d.

11. The method of claim 1, wherein the fluticasone is fluticasone propionate administered as a liquid aerosol in an amount of at least 200 μg b.i.d.

12. A method of treating chronic rhinosinusitis with or without nasal polyps in a patient comprising:
    placing a nosepiece into a first nostril of the patient;
    placing a mouthpiece into a mouth of the patient, the mouthpiece being fluidly connected to the nosepiece, wherein exhalation by the patient into the mouthpiece and out of the nosepiece produces a bi-directional fluid flow of exhalation air into a first nasal passageway of the patient and out of a second nasal passageway of the patient;
    administering fluticasone during exhalation by the patient through the nosepiece;
    delivering carbon dioxide during exhalation by the patient through the nosepiece, to a location at an upper posterior region of the first nasal passageway of the patient; and
    reducing a pH at the location at the upper posterior region of the first nasal passageway of the patient by an amount ranging from about 0.1 pH units to about 0.2 pH units by controlling the fluid flow to deliver the carbon dioxide at a concentration of from about 5% vol/vol to about 6% vol/vol carbon dioxide and at a fluid flow rate of at least 20 L/min for a duration of from about 2 seconds to about 3 seconds, wherein the carbon dioxide is delivered before or at the same time as the fluticasone.

13. The method of claim 12, wherein the fluticasone is fluticasone propionate.

14. The method of claim 12, wherein the fluticasone propionate is administered as a liquid aerosol.

15. The method of claim 12, wherein the fluticasone propionate is administered in an amount of about 400 μg b.i.d.

16. The method of claim 13, wherein the fluticasone is administered in an amount of 100 μg to 400 μg b.i.d.

17. The method of claim 13, wherein the fluticasone is administered in an amount of at least 200 μg daily.

18. The method of claim 13, wherein the fluticasone is administered in an amount of at least 400 μg daily.

19. The method of claim 13, wherein the fluticasone is administered in an amount of at least 200 μg daily delivered in two doses.

20. The method of claim 13, wherein the fluticasone is administered in an amount of at least 400 μg daily delivered in two doses.

21. The method of claim 13, wherein the fluticasone is fluticasone propionate administered as a liquid aerosol in an amount of 100 μg to 400 μg b.i.d.

22. The method of claim 13, wherein the fluticasone is fluticasone propionate administered as a liquid aerosol in an amount of at least 200 μg b.i.d.

* * * * *